United States Patent
Haga et al.

(10) Patent No.: US 9,770,713 B2
(45) Date of Patent: Sep. 26, 2017

(54) NUCLEIC ACID ANALYSIS DEVICE

(71) Applicant: Hitachi High-Technologies Corporation, Tokyo (JP)

(72) Inventors: Takanobu Haga, Tokyo (JP);
Yoshitaka Kodama, Tokyo (JP);
Tomohiro Shoji, Tokyo (JP);
Takamichi Muramatsu, Tokyo (JP);
Shuhei Yamamoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 114 days.

(21) Appl. No.: 14/421,239

(22) PCT Filed: Jul. 8, 2013

(86) PCT No.: PCT/JP2013/068588
§ 371 (c)(1),
(2) Date: Feb. 12, 2015

(87) PCT Pub. No.: WO2014/034275
PCT Pub. Date: Mar. 6, 2014

(65) Prior Publication Data
US 2015/0202618 A1    Jul. 23, 2015

(30) Foreign Application Priority Data

Aug. 30, 2012   (JP) .................... 2012-189423

(51) Int. Cl.
C12Q 1/68 (2006.01)
B01L 3/00 (2006.01)
G01N 21/64 (2006.01)
B01L 99/00 (2010.01)

(52) U.S. Cl.
CPC ............ B01L 3/50 (2013.01); B01L 99/00 (2013.01); C12Q 1/6869 (2013.01); G01N 21/6428 (2013.01); B01L 3/5027 (2013.01); B01L 2300/0636 (2013.01); C12Q 2535/122 (2013.01)

(58) Field of Classification Search
None
See application file for complete search history.

(56) References Cited

U.S. PATENT DOCUMENTS

| | | | | |
|---|---|---|---|---|
| 7,981,604 B2* | 7/2011 | Quake | ............ | C12Q 1/6869 435/6.12 |
| 2002/0168678 A1* | 11/2002 | Williams | ............ | C07H 19/10 435/6.12 |
| 2003/0186255 A1* | 10/2003 | Williams | ............ | C07H 19/10 506/16 |
| 2007/0219367 A1* | 9/2007 | Shchepinov | ....... | G01N 21/6428 536/25.32 |
| 2008/0293071 A1* | 11/2008 | Gelfand | ............ | C12Q 1/6869 435/6.12 |
| 2010/0010749 A1 | 1/2010 | Isaacs | | |
| 2010/0035253 A1* | 2/2010 | Gordon | ............ | C12Q 1/6825 435/6.11 |
| 2010/0111768 A1* | 5/2010 | Banerjee | ............ | G01N 21/6456 422/82.08 |
| 2011/0065607 A1* | 3/2011 | Kersey | ............ | C12Q 1/6806 506/16 |
| 2011/0072914 A1* | 3/2011 | Lebl | ............ | B01L 3/50273 73/864.11 |
| 2012/0316086 A1* | 12/2012 | Lin | ............ | G01N 27/447 506/26 |

FOREIGN PATENT DOCUMENTS

JP      2009-514518    4/2009
WO      2012/111366    8/2012

OTHER PUBLICATIONS

D.R. Bentley et al., Accurate whole human genome sequencing using reversible terminator chemistry, Nature, vol. 456, Nov. 2008, pp. 53-59.
Marcel Margulies et al., Genome sequencing in microfabricated high-density picolitre reactors, Nature, vol. 437, Sep. 2005, pp. 376-380.
Atsushi Toyota, et al., Genome sequencing by Next-Generation Sequencers and Future Trends, Experimental Medicine, vol. 27, No. 12, 2009, pp. 113 (1929) to 119 (1935).
Chao Sun et al., De novo sequencing and analysis of the American ginseng root transcriptome using a GS FLX Titanium platform to discover putative genes involved in ginsenoside biosynthesis, BMC Genomics, vol. 11, 262, 2010, pp. 1-12.
Jongsik Chun et al., The analysis of oral microbial communities of wild-type and toll-like receptor 2-deficient mice using a 454 GS FLX Titanium pyrosequencer, BMC Microbiology, 2010, vol. 10, 101, pp. 1-8.

(Continued)

Primary Examiner — Aaron Priest
(74) Attorney, Agent, or Firm — Mattingly & Malur, PC

(57) ABSTRACT

A nucleic acid analysis device which can determine a DNA sequence has a flowcell in which two or more DNA fragment clusters of two or more DNA fragments having identical nucleotide sequences are immobilized. At least a part of the flowcell is made of a transparent material. An irradiation unit irradiates a part in which the DNA fragment clusters are immobilized. The device has a lens for collecting fluorescence, and a light-detection element. A solution containing only dATP having a fluorescently modified phosphate terminal among four bases, a solution containing only dCTP having a fluorescently modified phosphate terminal among the four bases, a solution containing only dGTP having a fluorescently modified phosphate terminal among the four bases, a solution containing only dTTP having a fluorescently modified phosphate terminal among the four bases, and a buffer solution are sent sequentially to where the DNA fragment clusters are immobilized.

16 Claims, 43 Drawing Sheets

(56) References Cited

OTHER PUBLICATIONS

John Eid et al., Real-Time DNA Sequencing from Single Polymerase Molecules, Science, 2009, vol. 323, pp. 133-138.
Ben Tran et al., Cancer Genomics: Technology, Discovery, and Translation, J Clin Oncol., 2012, 02, vol. 30, No. 6, pp. 647-660.
David A. Rasko et al., Origins of the *E. coli* Strain Causing an Outbreak of Hemolytic-Uremic Syndrome in Germany, N. Engl J Med., 2011, vol. 365, No. 8, pp. 709-717.
Sharong Liu et al., Optimization of High-Speed DNA Sequencing on Microfabricated Capillary Electrophoresis Channels, Anal Chem., 1999, vol. 71, No. 3, pp. 566-573.
International Search Report in PCT/JP2013/068588 dated, Sep. 10, 2013.

* cited by examiner

[FIG. 1]
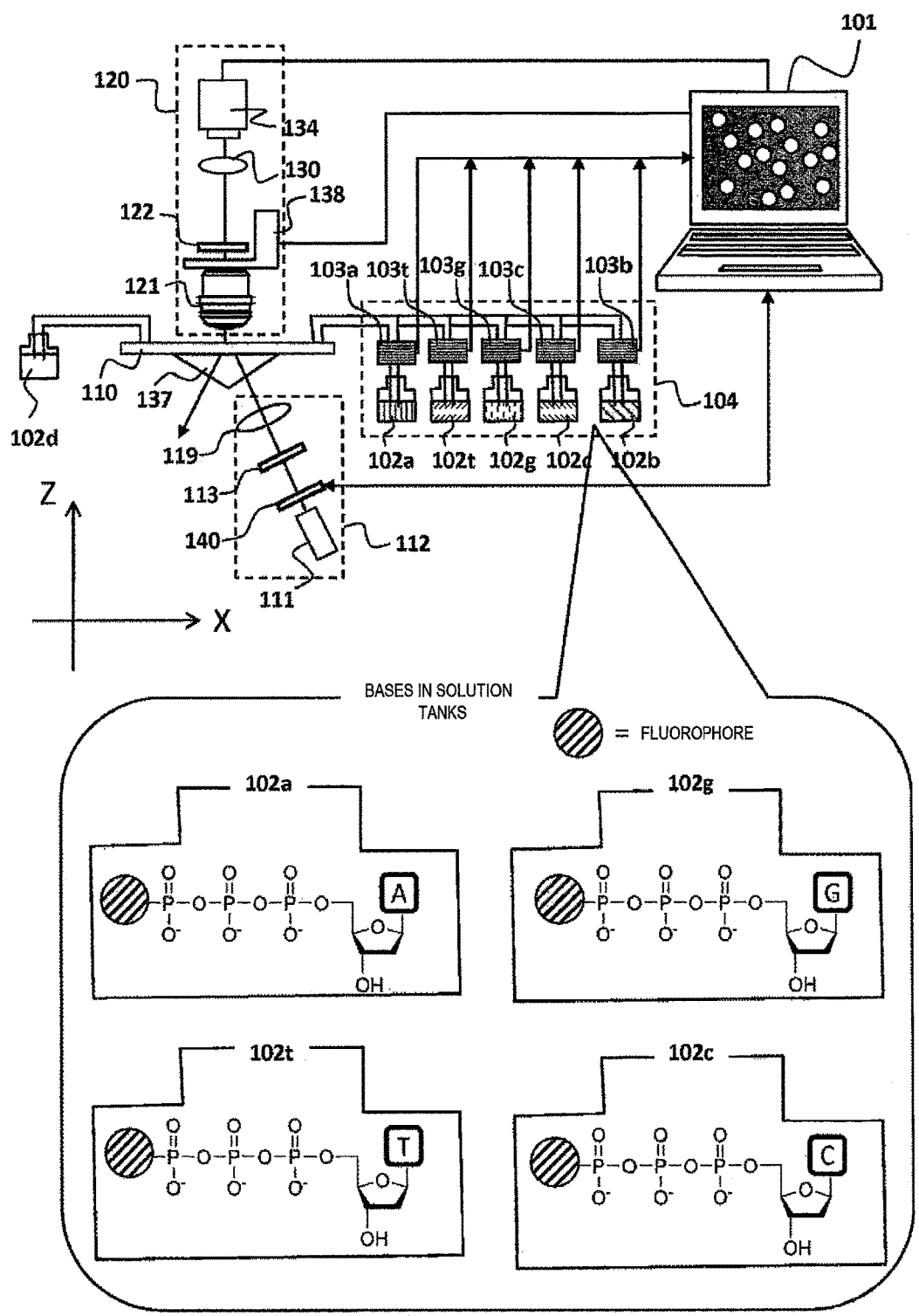

[FIG. 2]
(a)
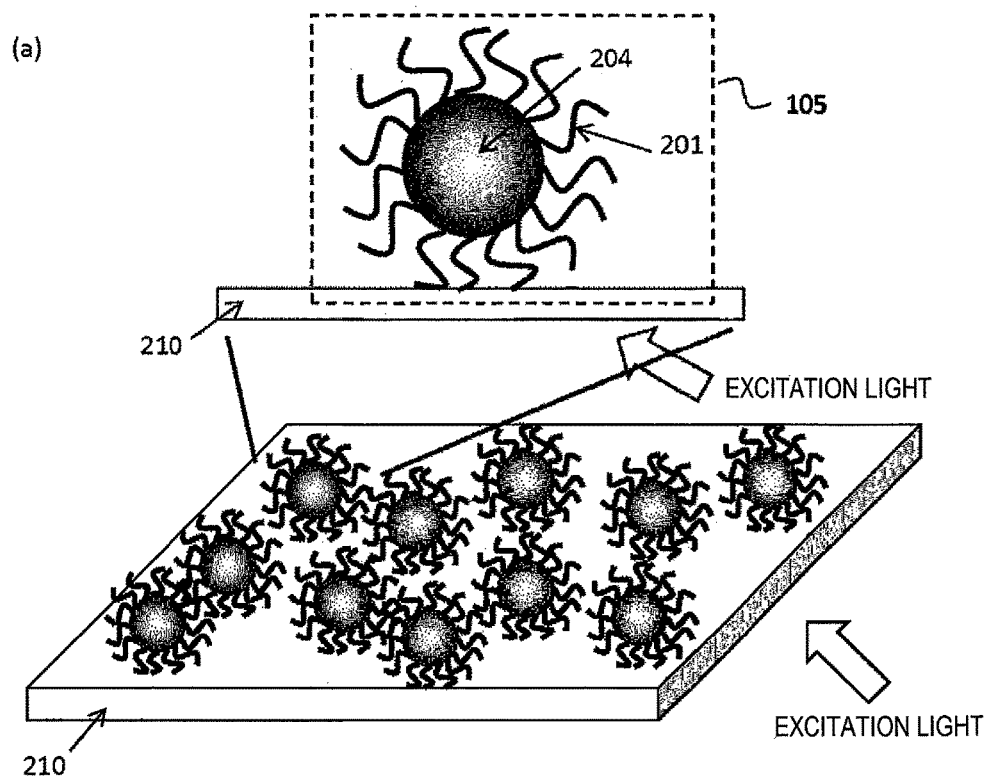
(b)
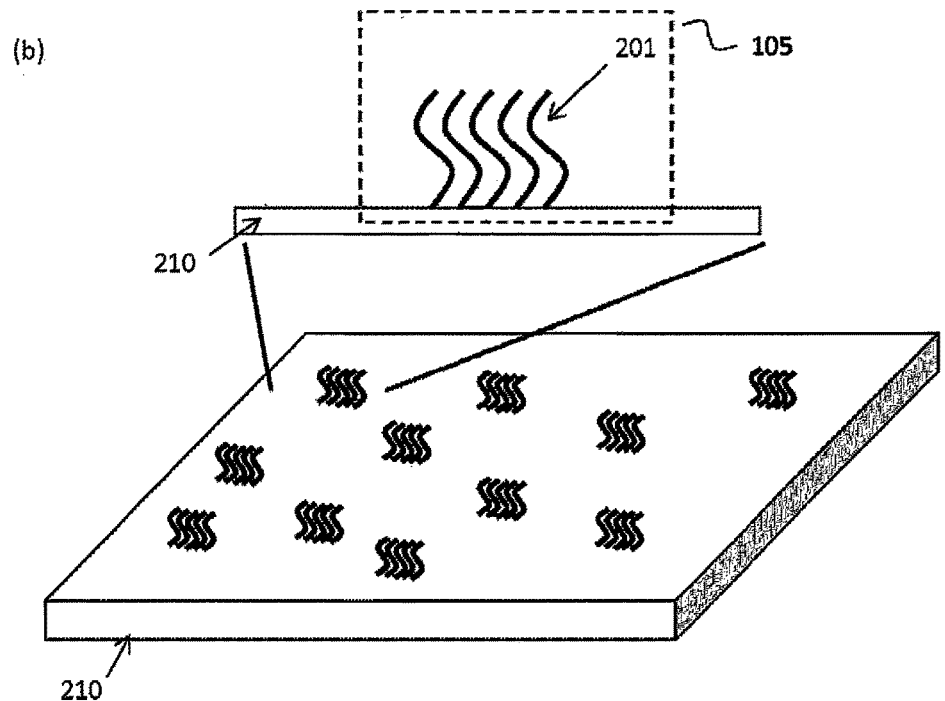

[FIG. 3]
[EXAMPLE 1]
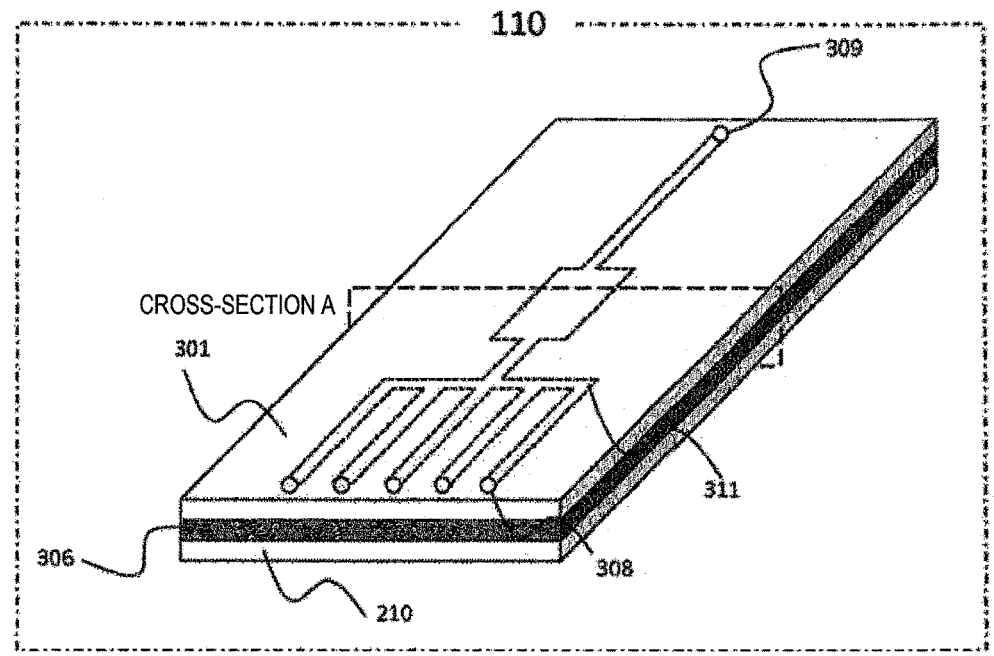
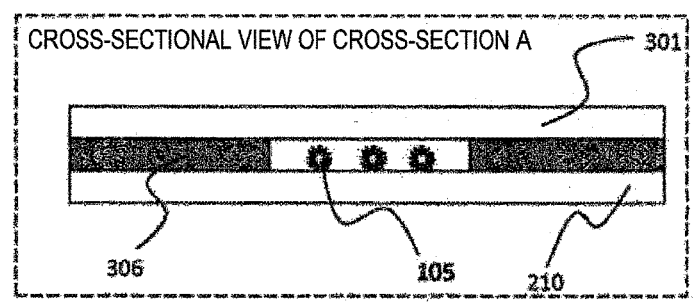

[FIG. 4]
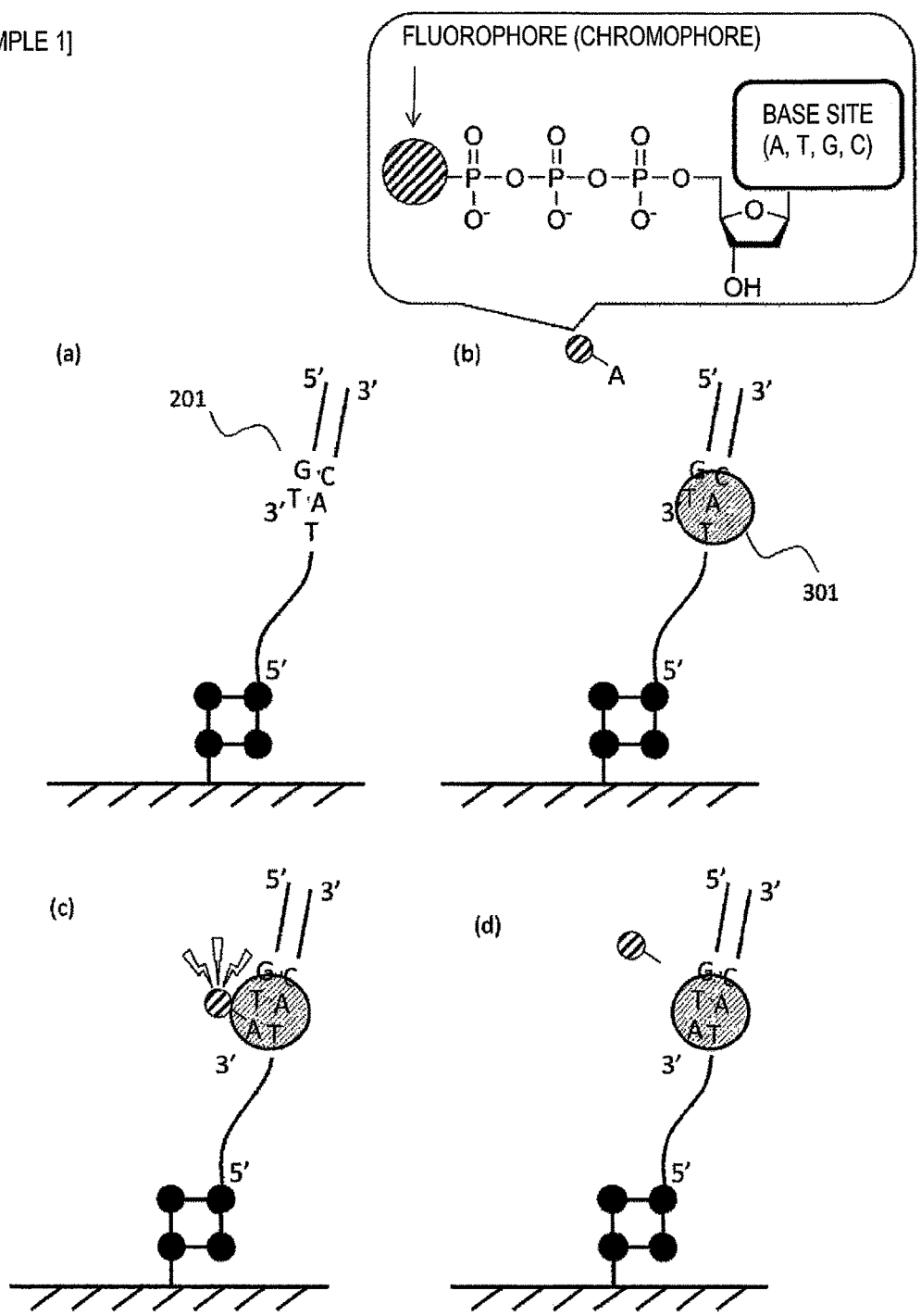

[FIG. 5]
[EXAMPLE 1]
(a)
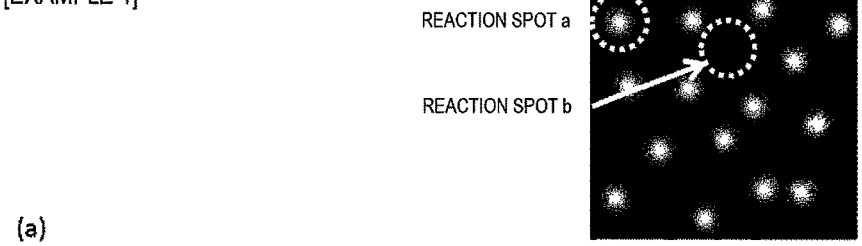
(b)
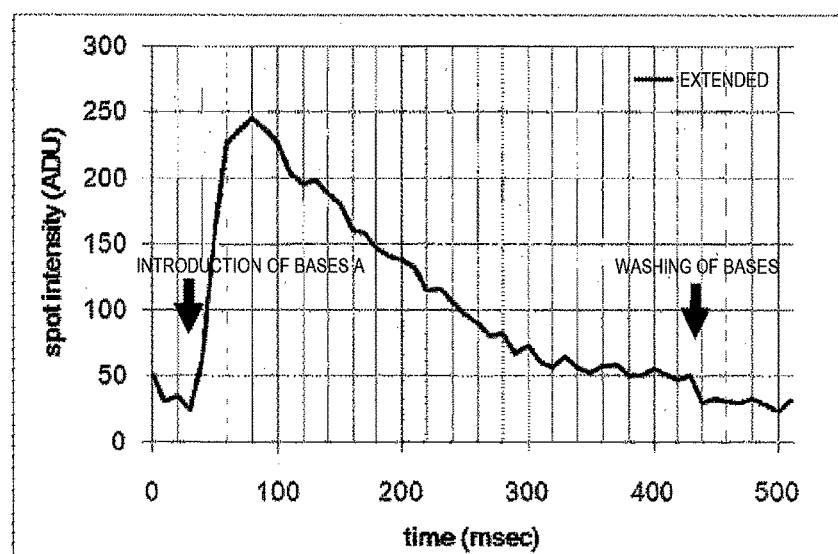
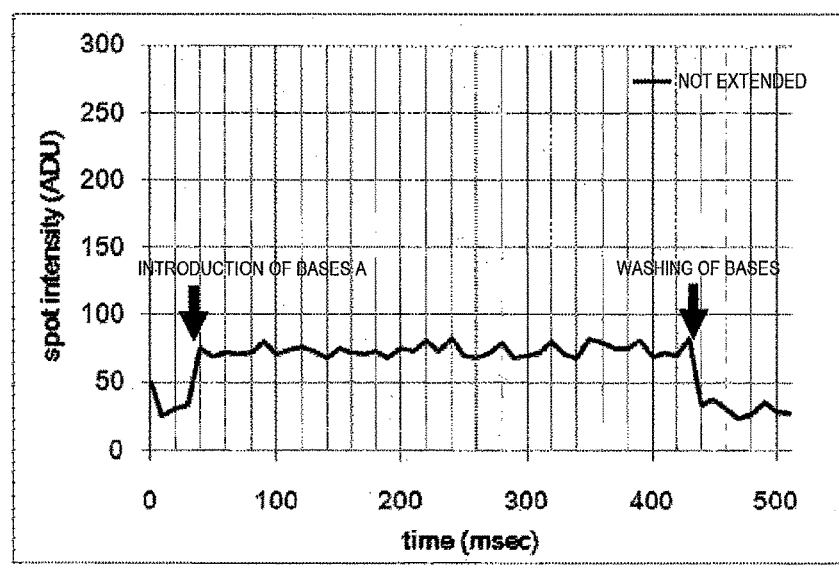

[FIG. 6]
[EXAMPLE 1]
(a) REACTION SPOT 1
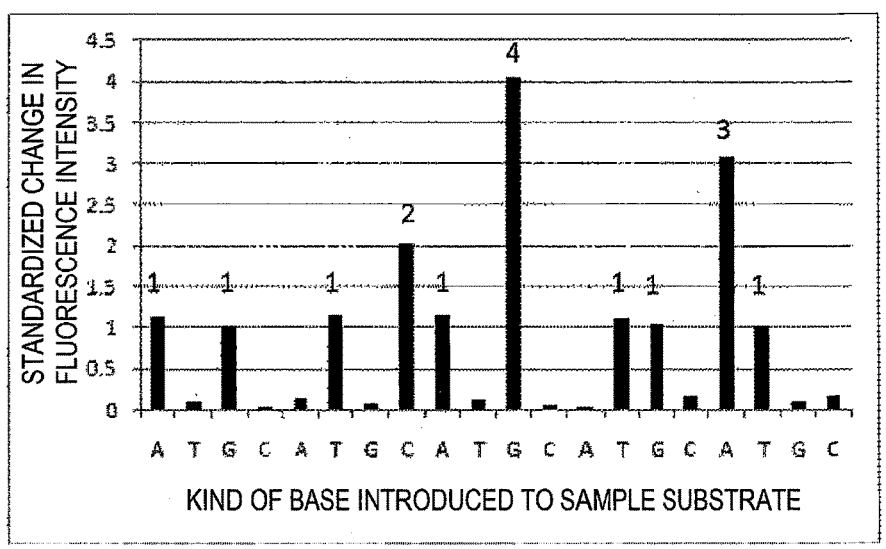
(b) REACTION SPOT 2
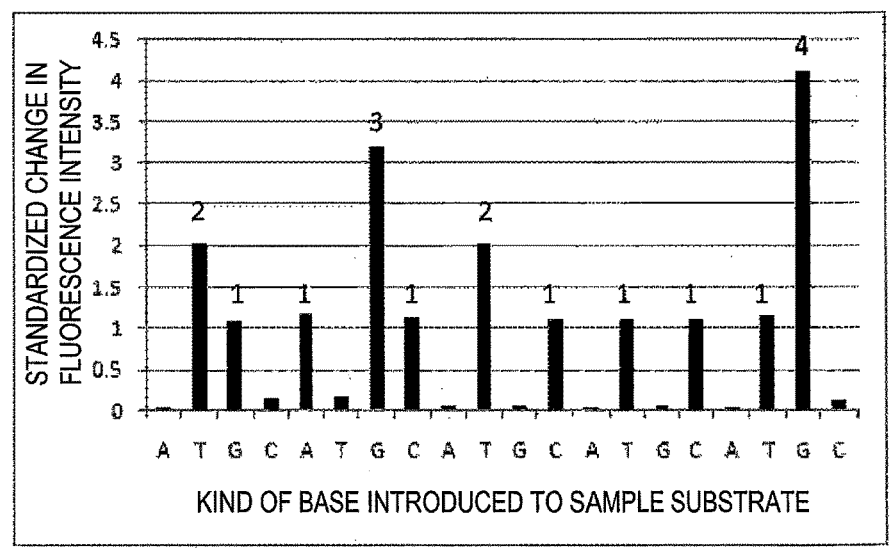

[FIG. 7]
FLOWCHART OF SEQUENCING CYCLE
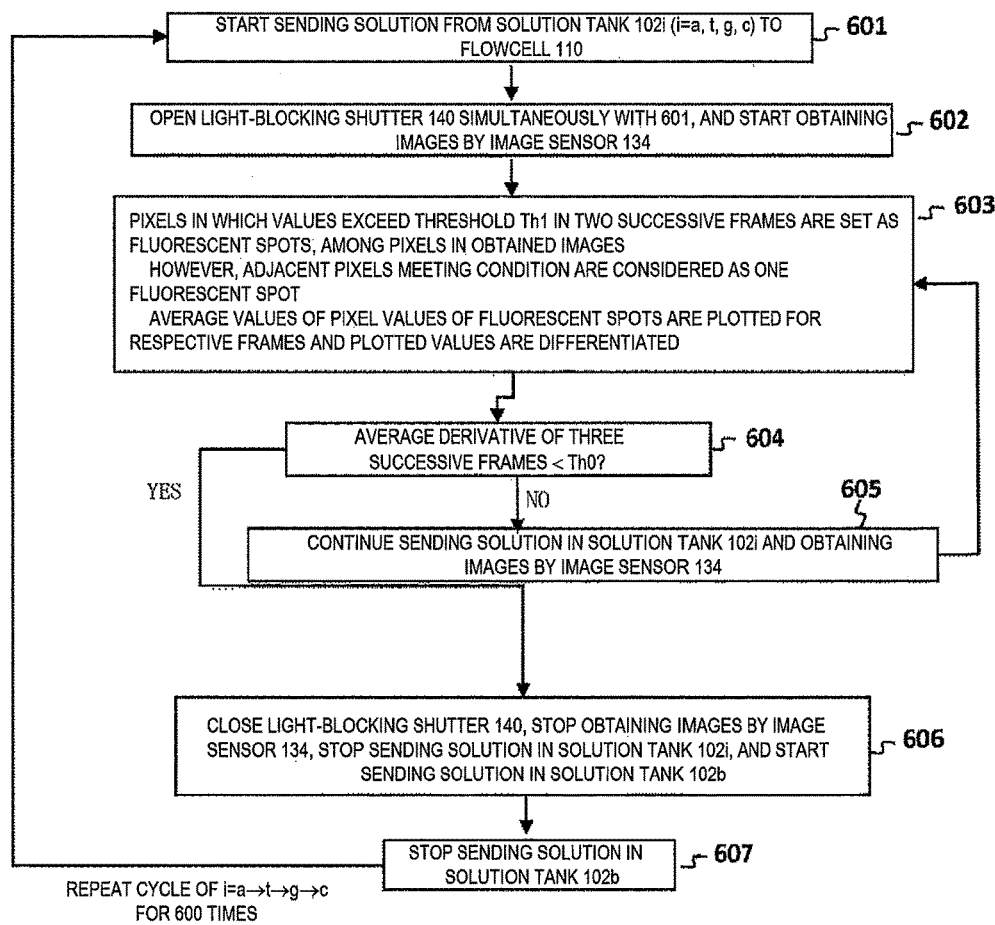

[FIG. 8]
FLOWCHART OF BASE CALLING OF REACTION SPOTS
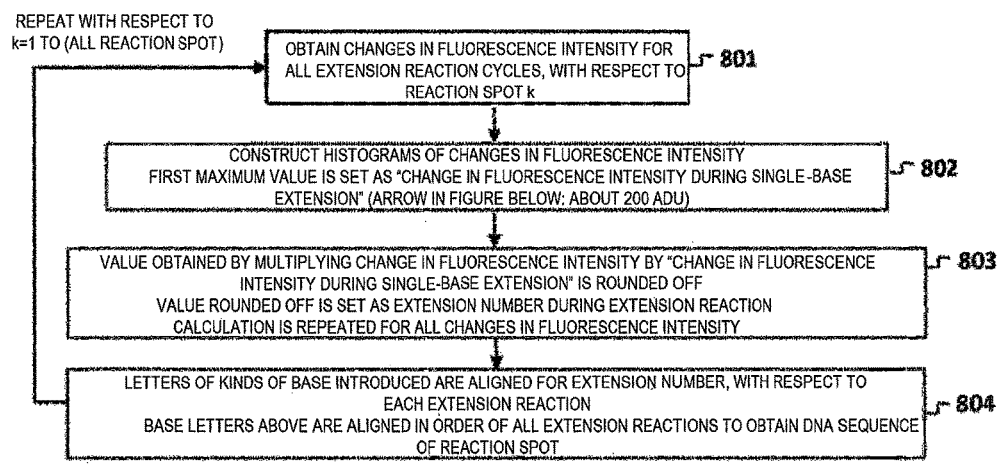
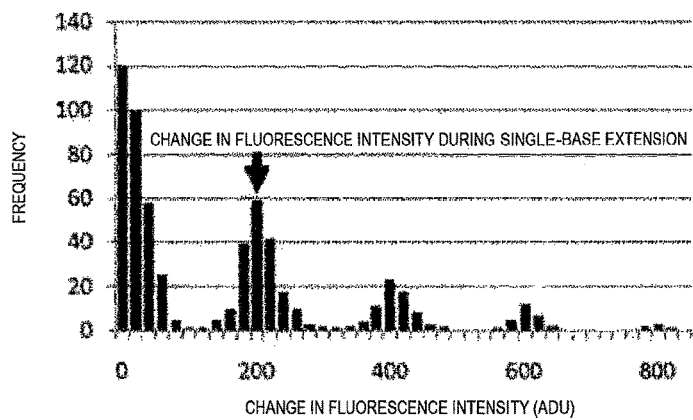

[FIG. 9]
(a)
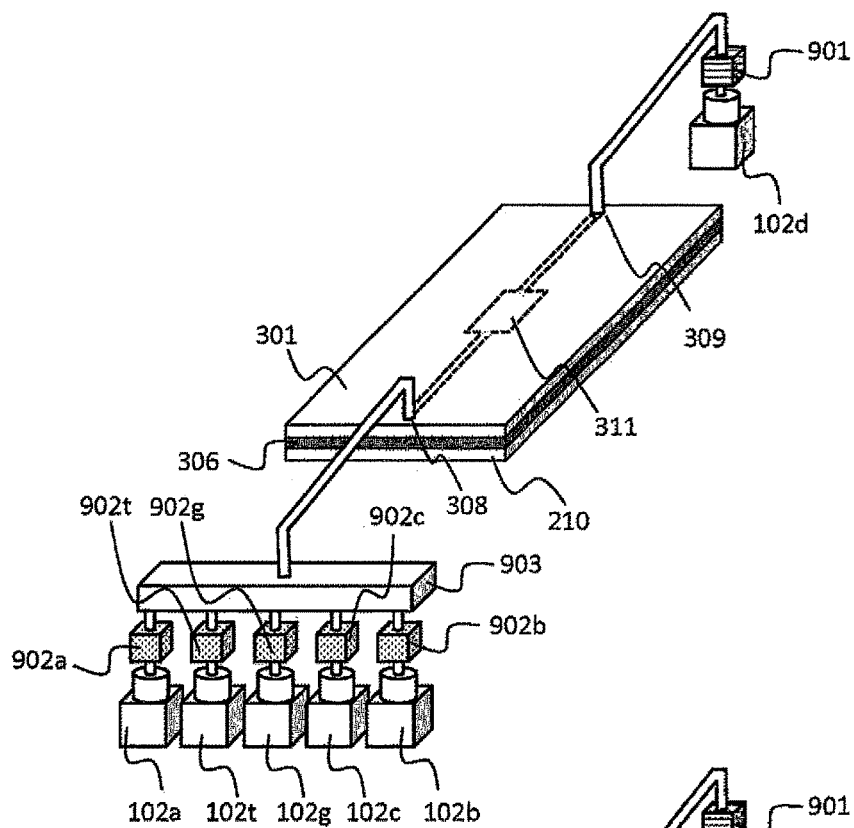
(b)
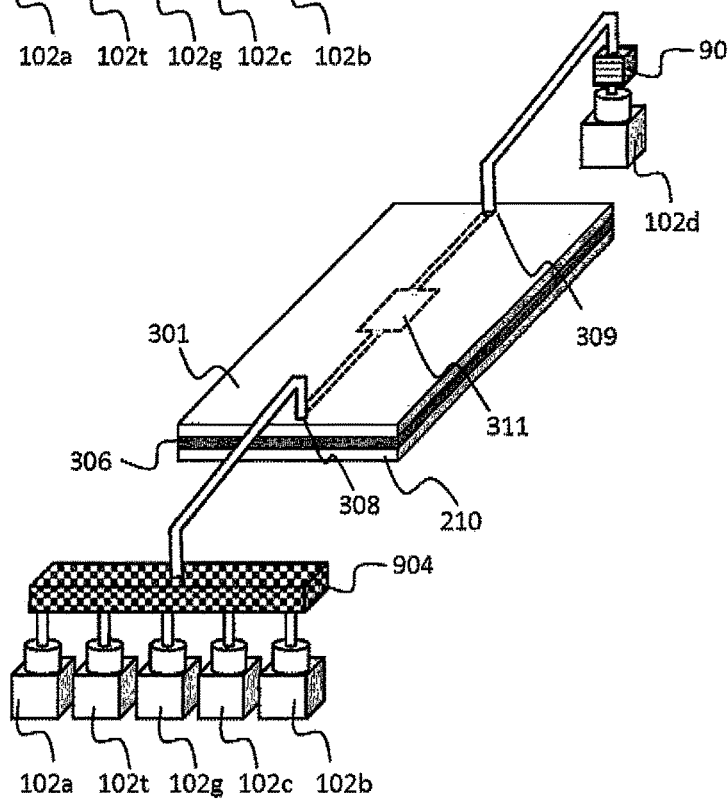

[FIG. 10]
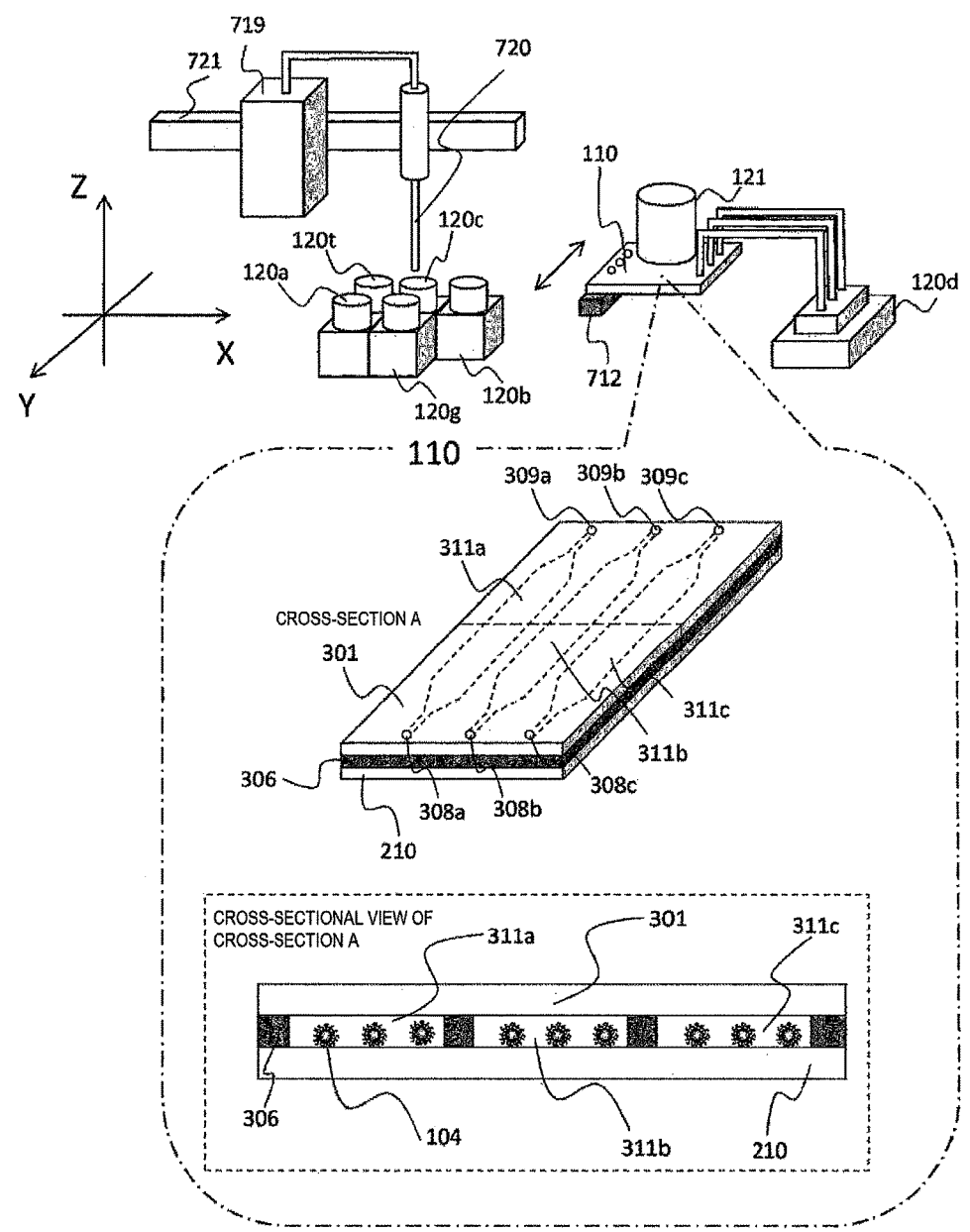

[FIG. 11]
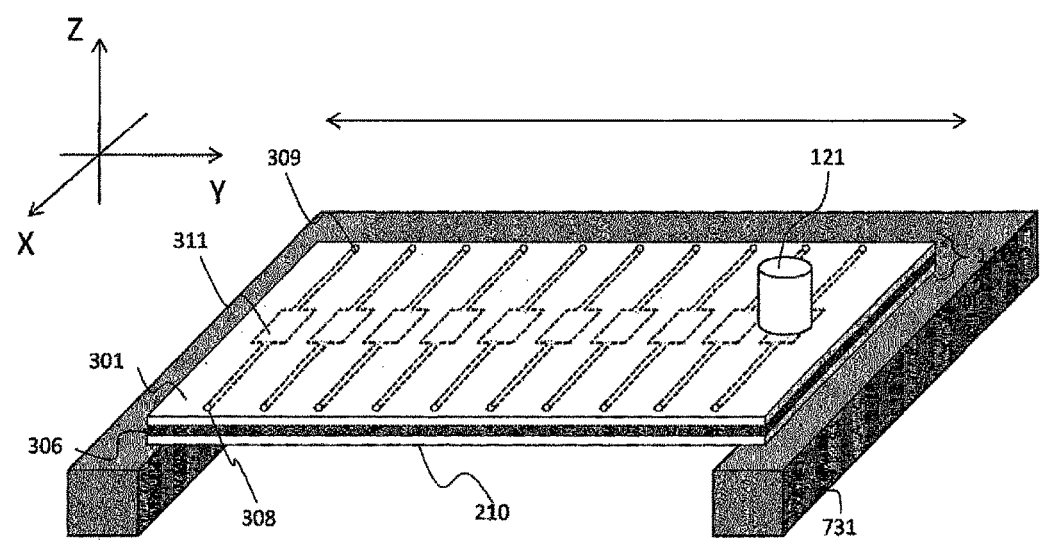

[FIG. 12]
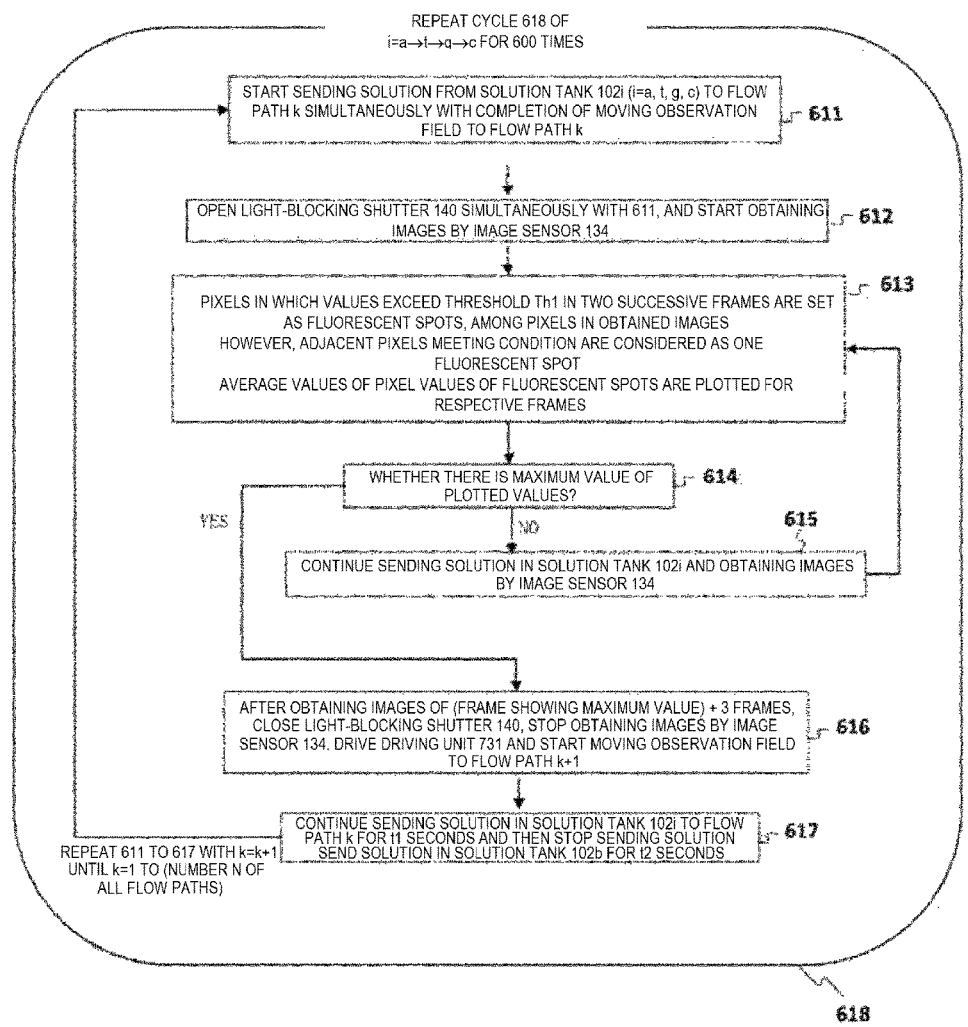

[FIG. 13]
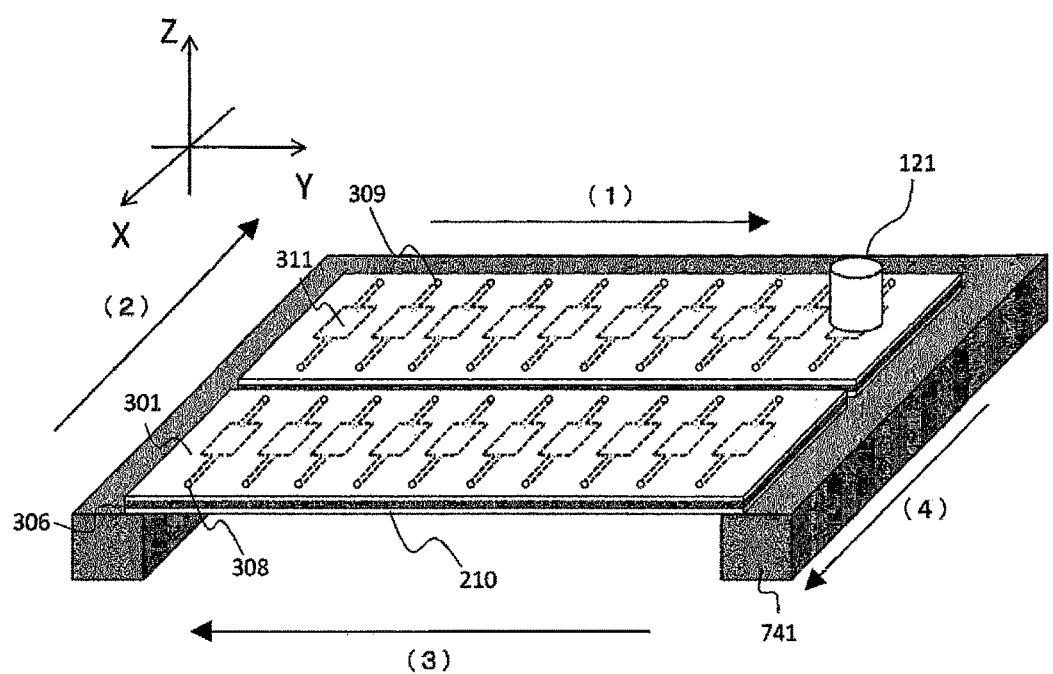

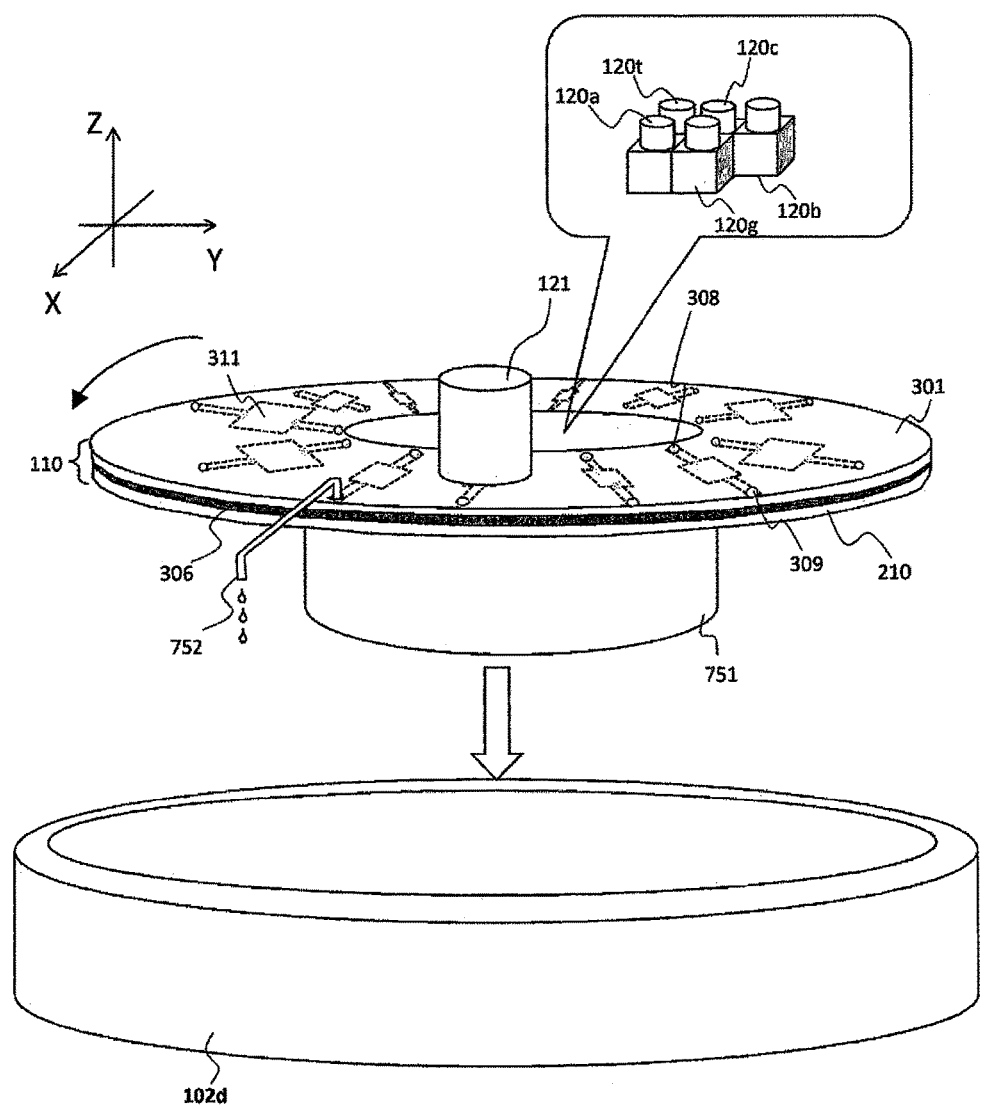
[FIG. 14]

[FIG. 15]
(a)
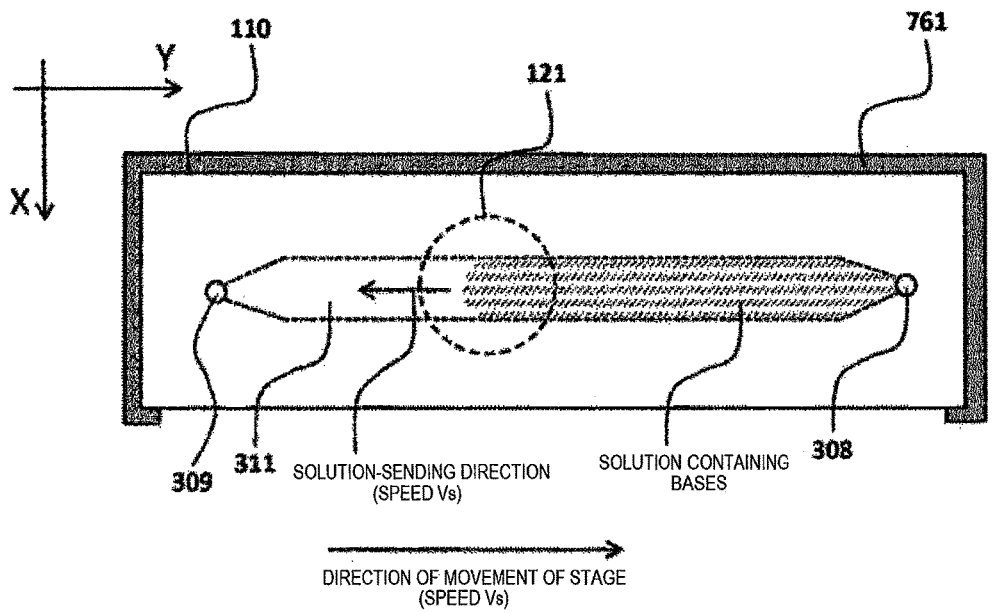
(b)
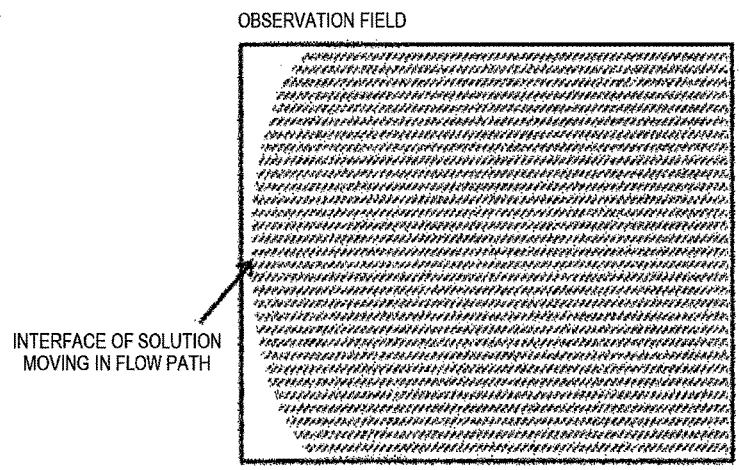

[FIG. 16]
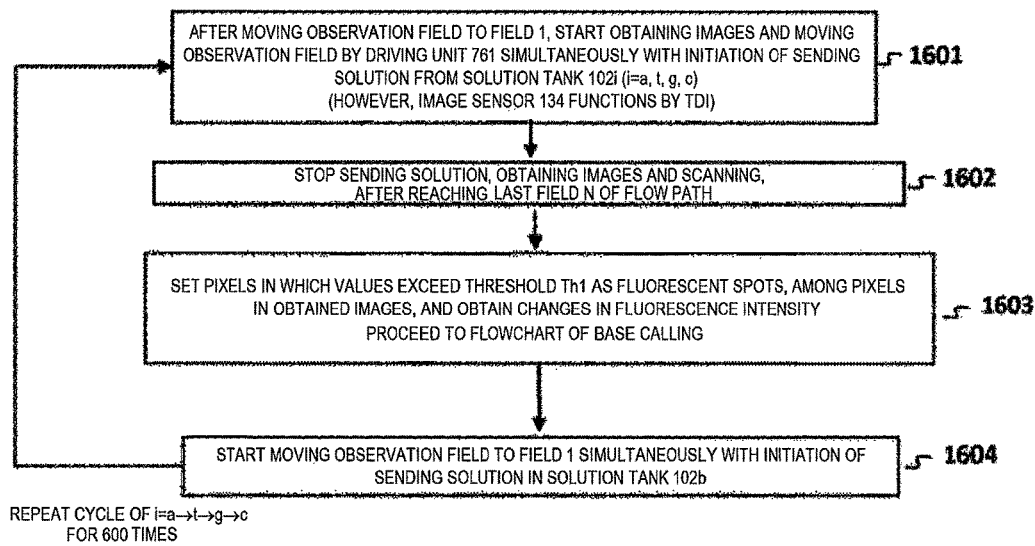

[FIG. 17]
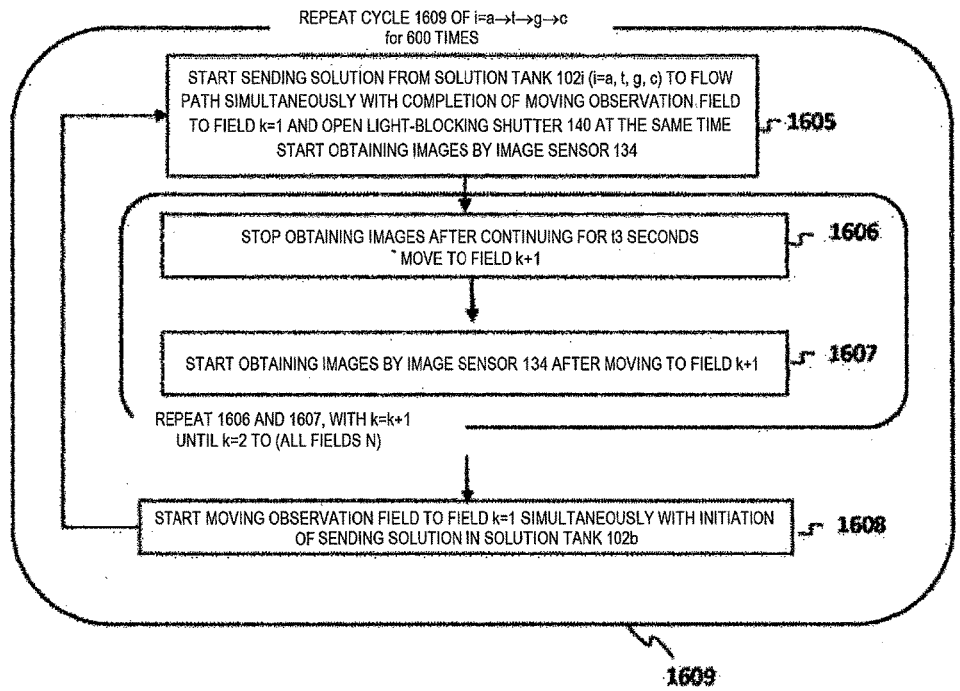

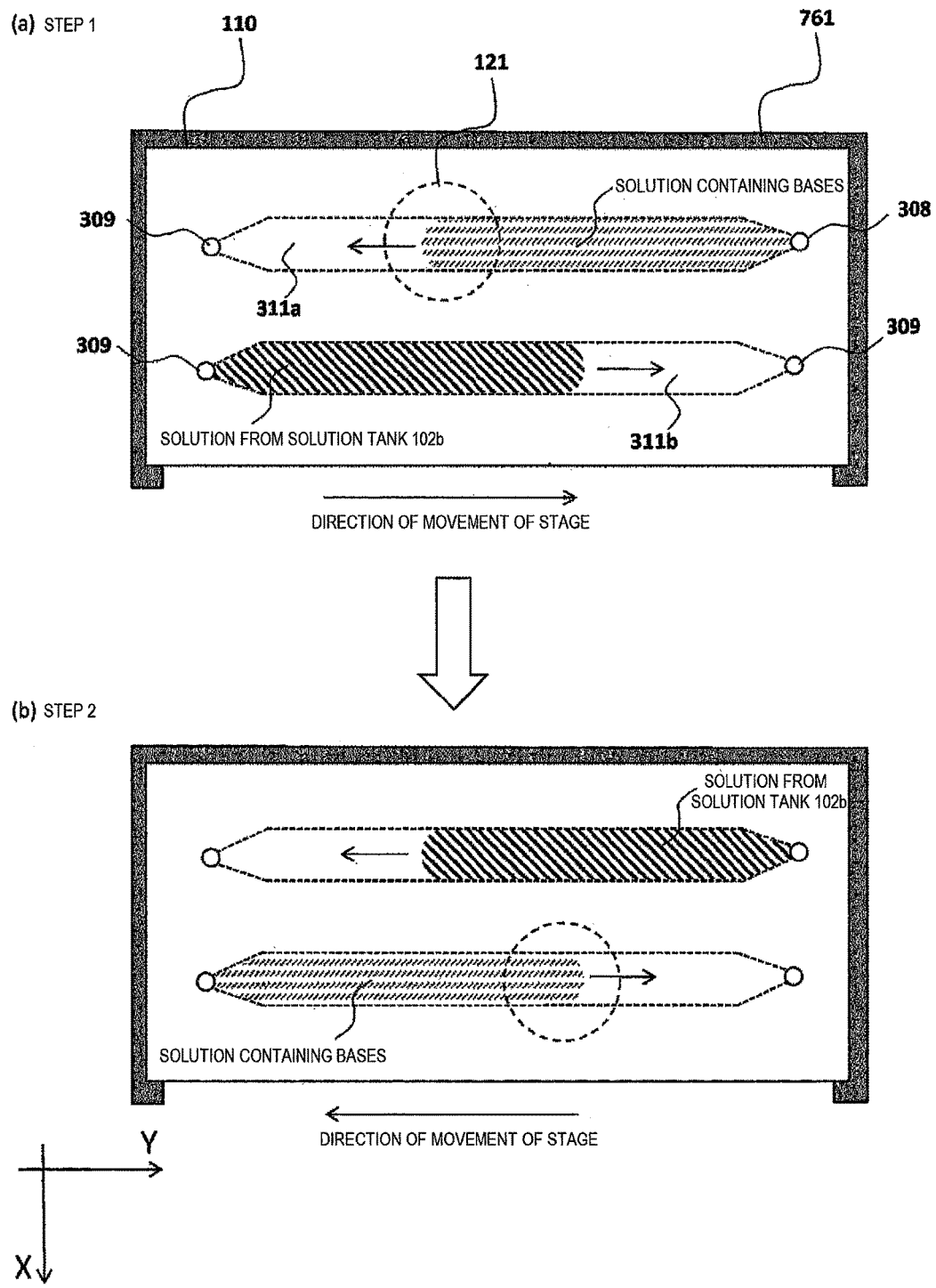
[FIG. 18]

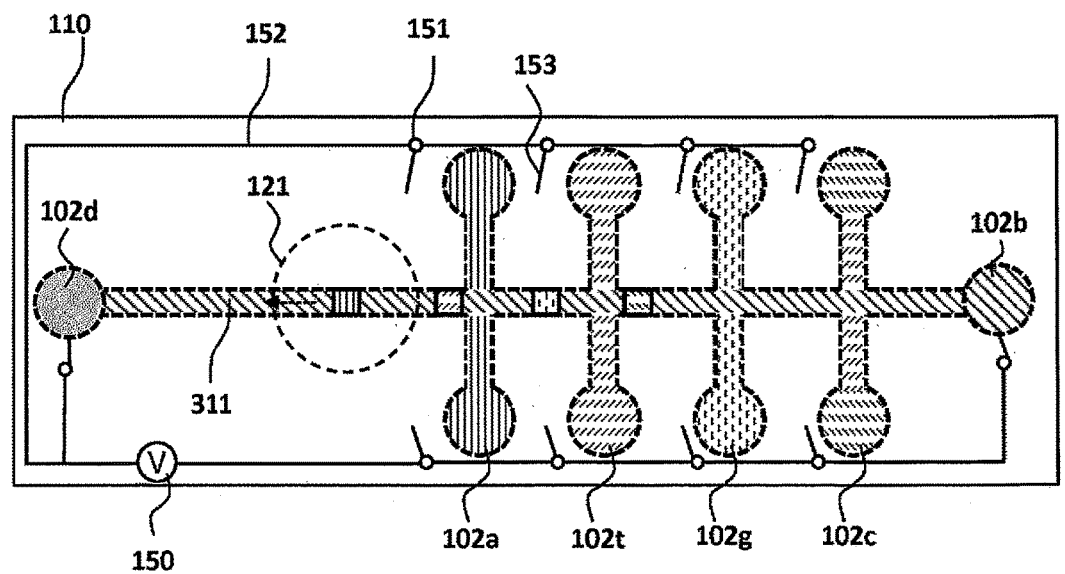
[FIG. 19]

[FIG. 20]
(a)
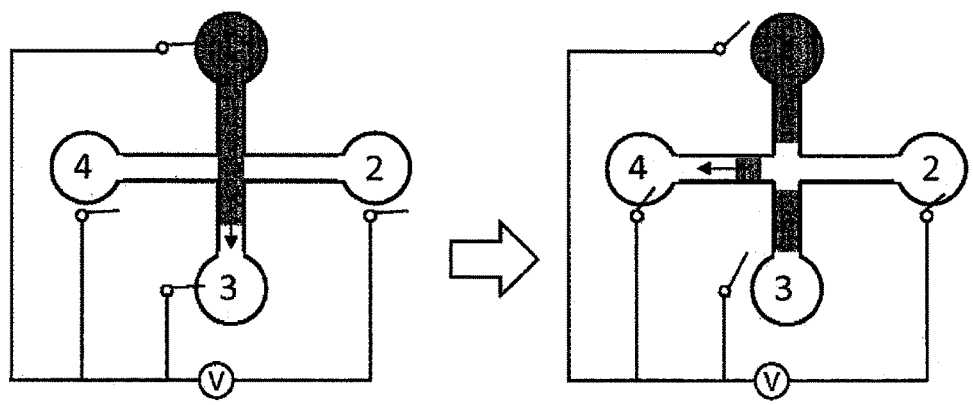
(b)
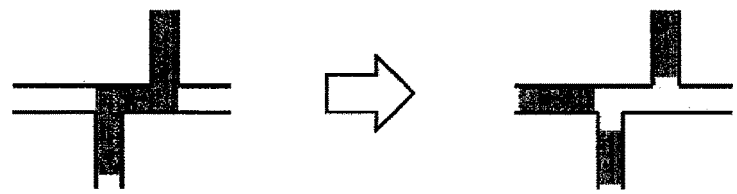

[FIG. 21]
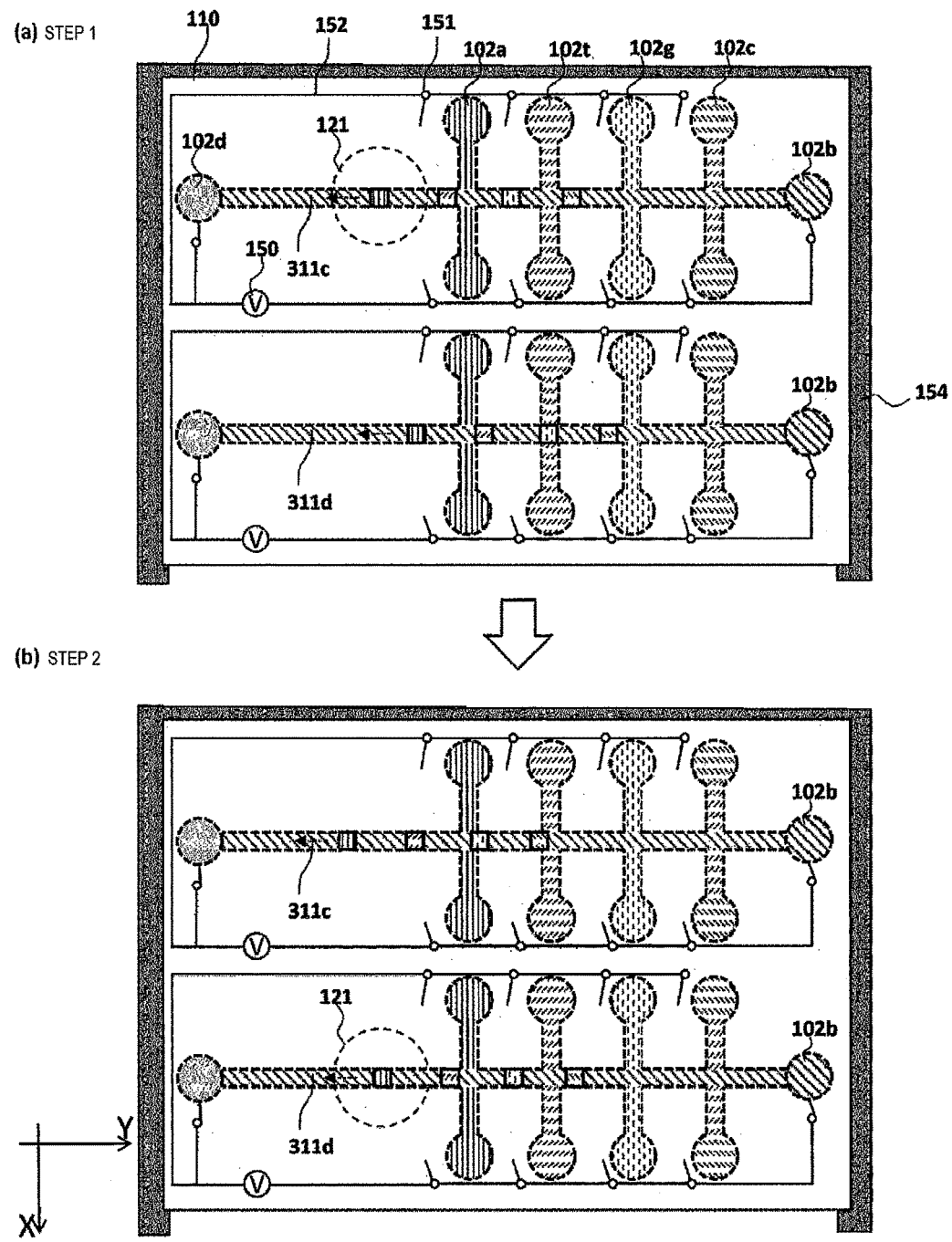

[FIG. 22]
(a)
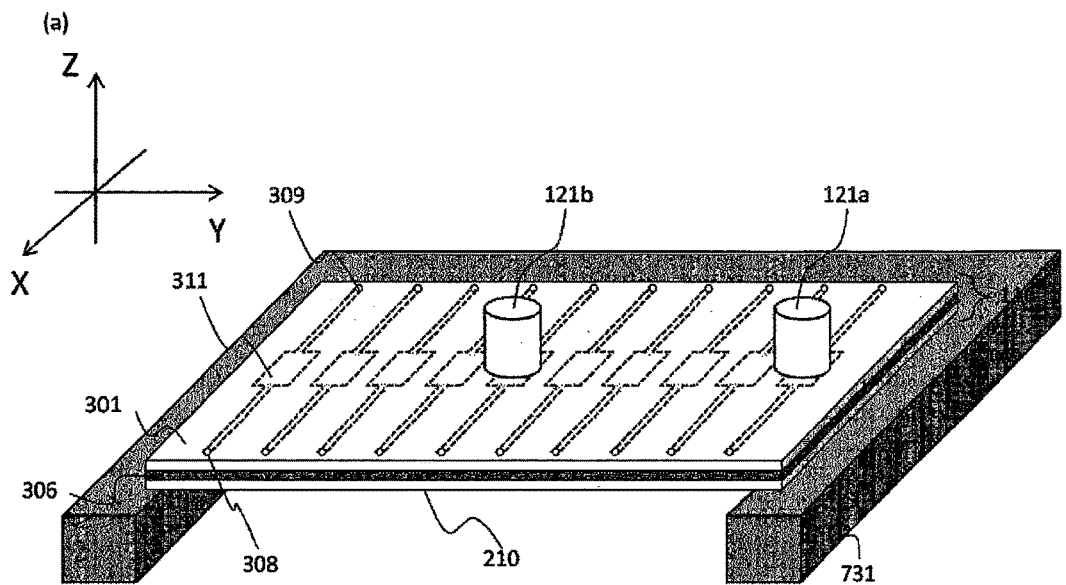
(b)
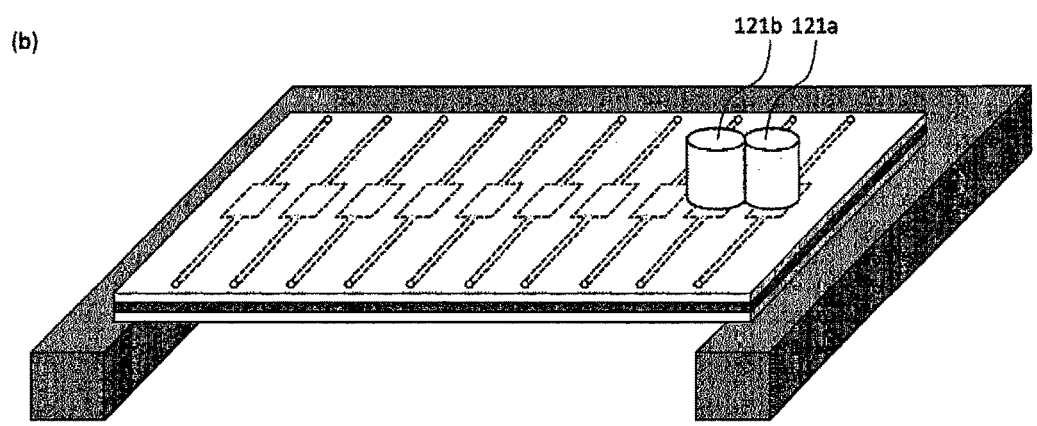

[FIG. 23]
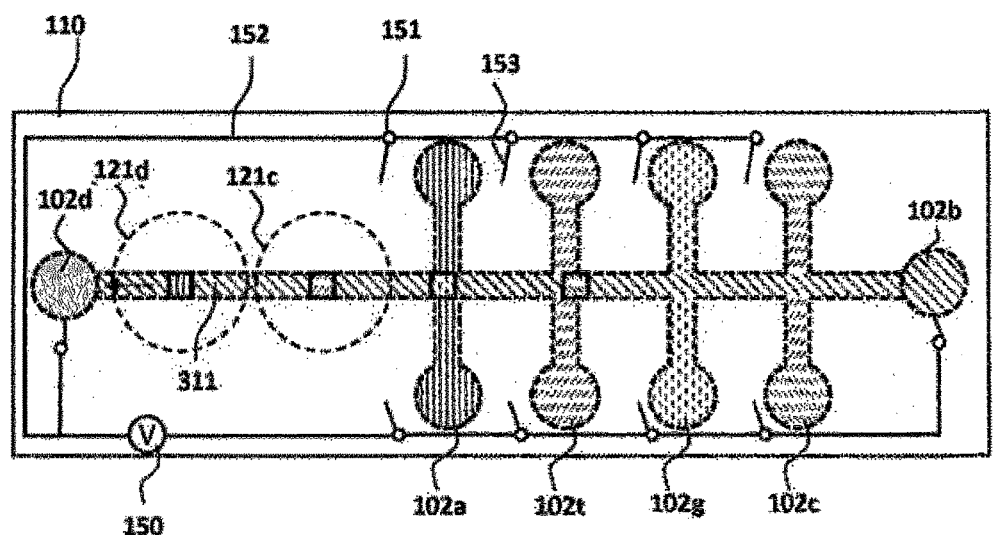

[FIG. 24]
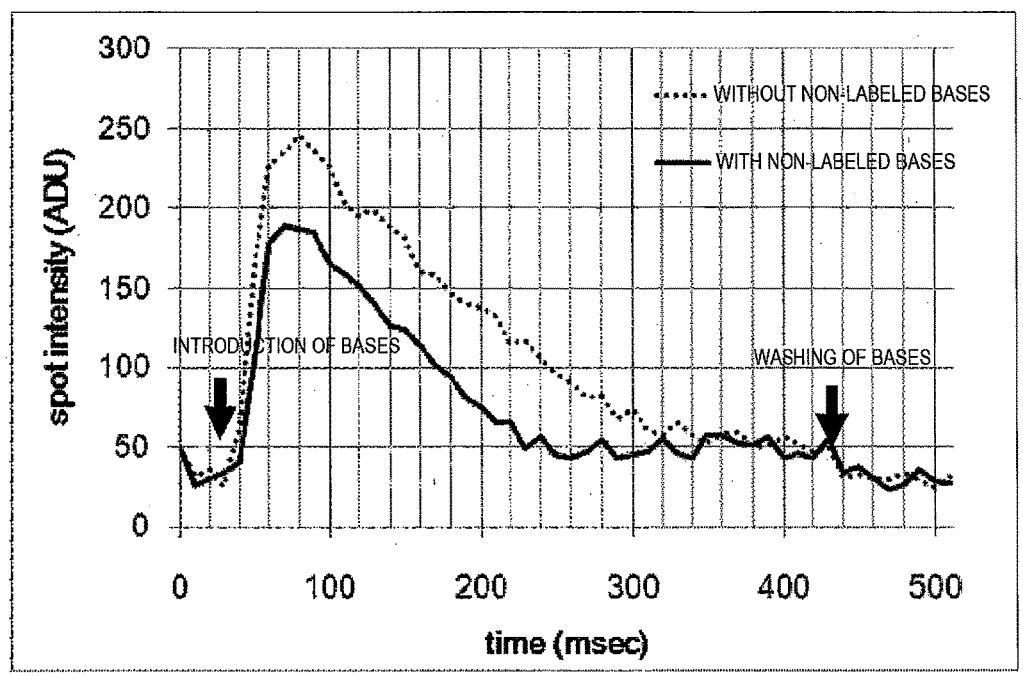

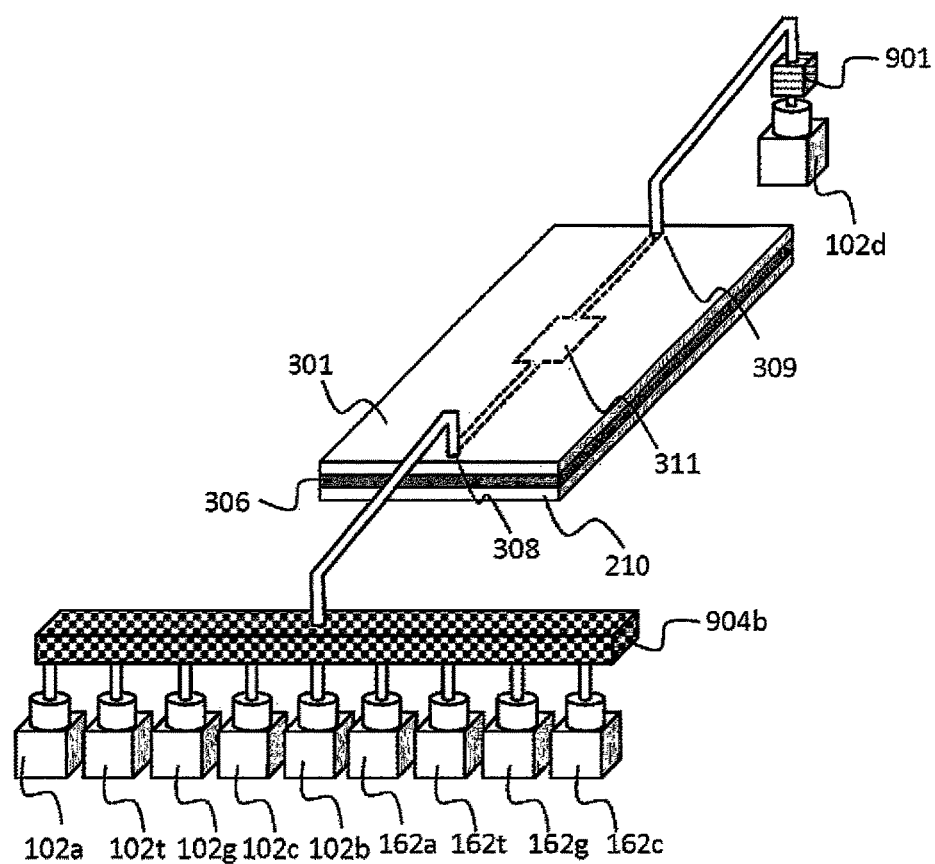
[FIG. 25]

[FIG. 26]
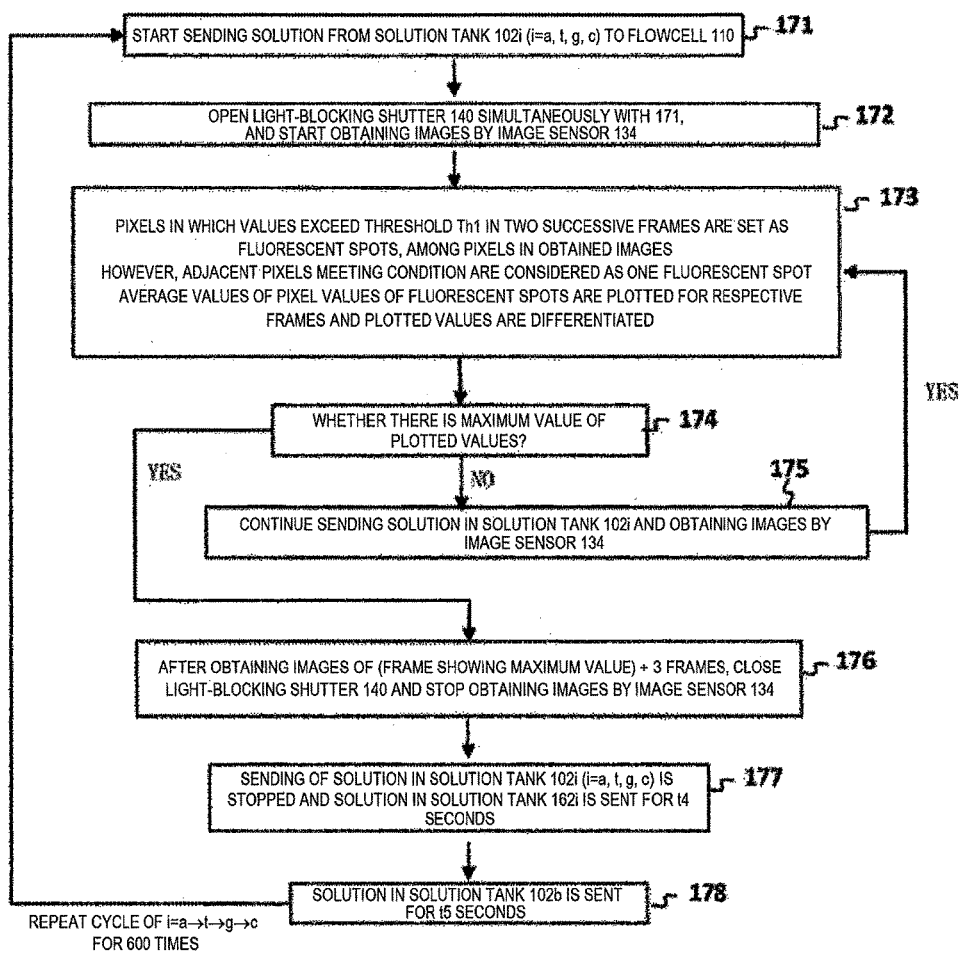

[FIG. 27]
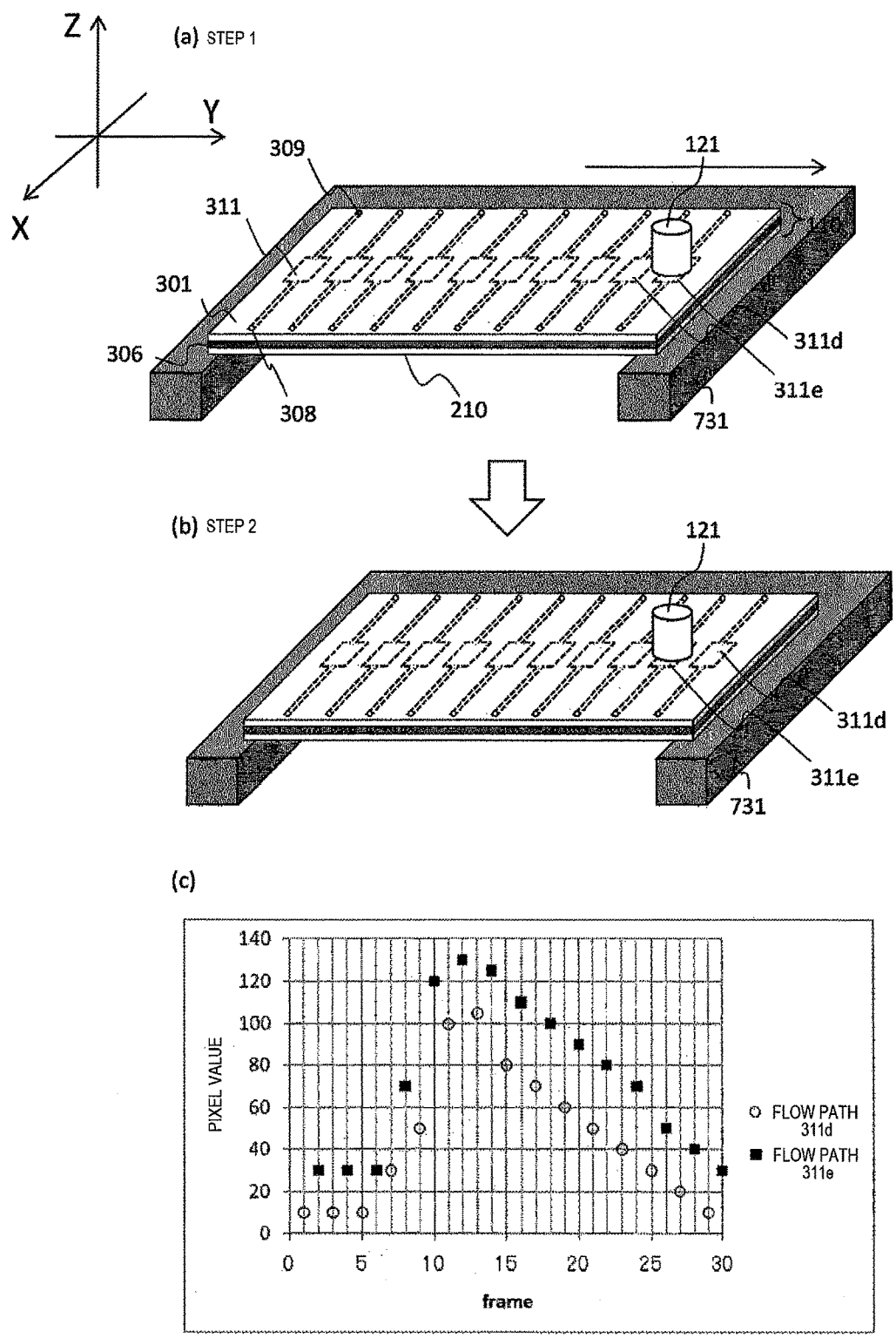

[FIG. 28]
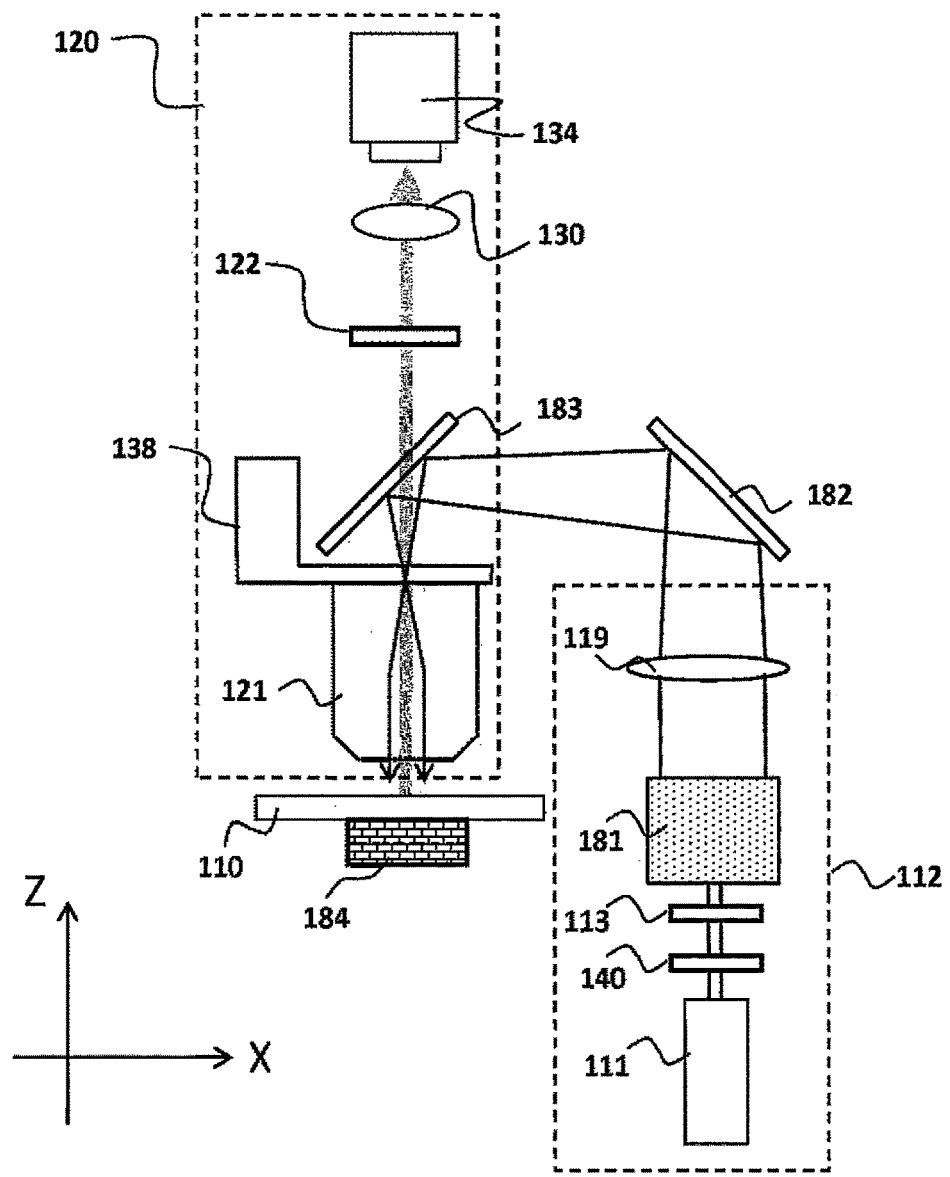

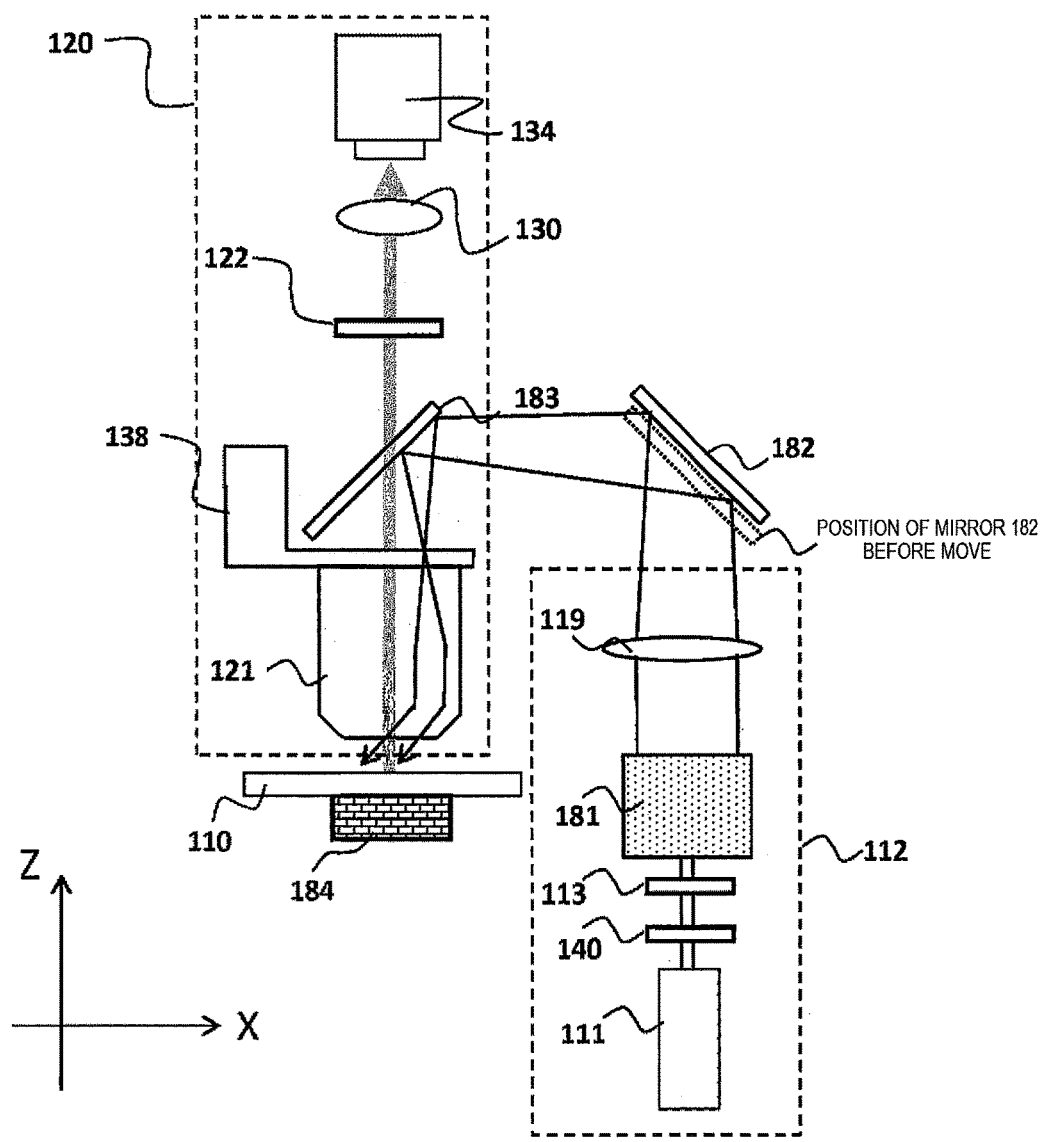
[FIG. 29]

[FIG. 30]
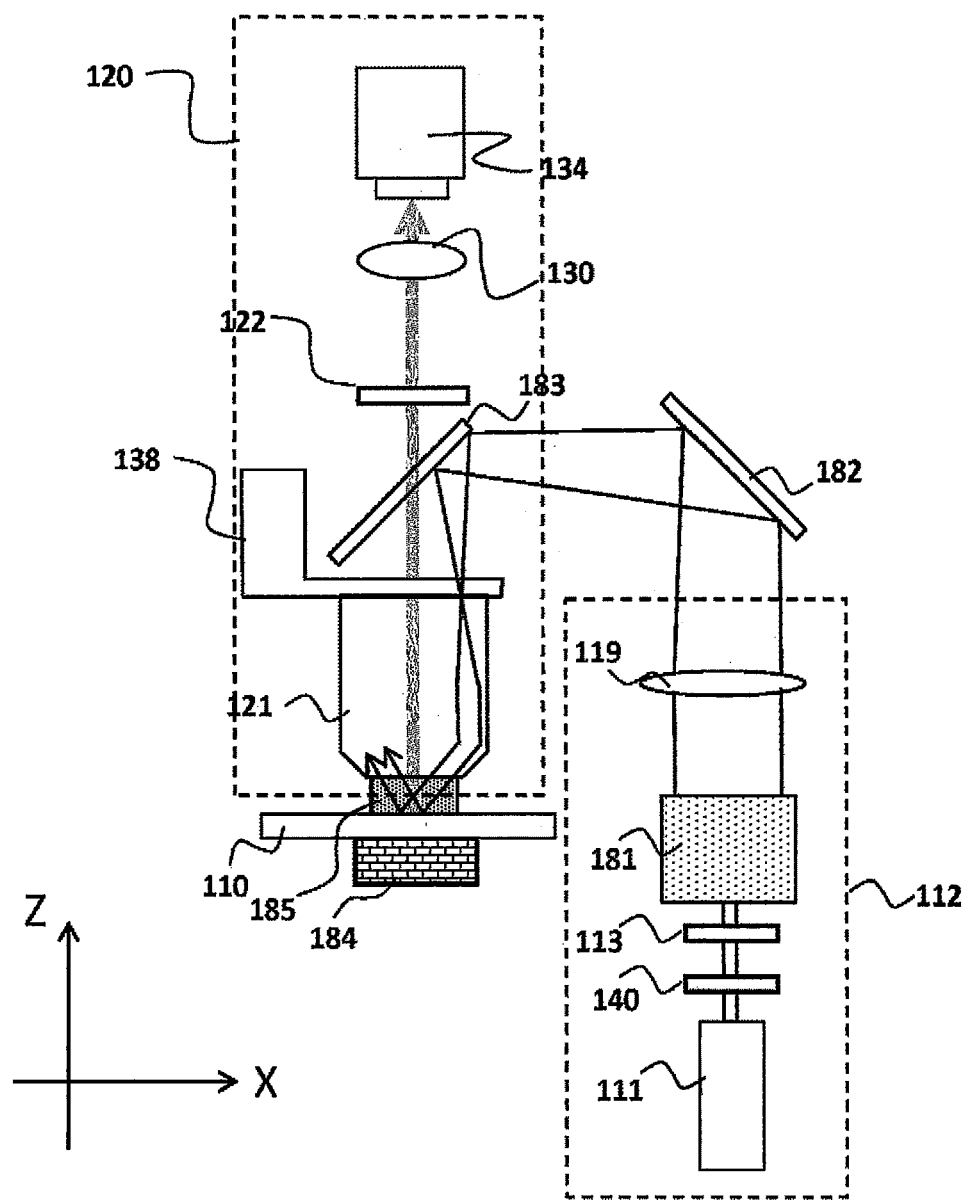

[FIG. 31]
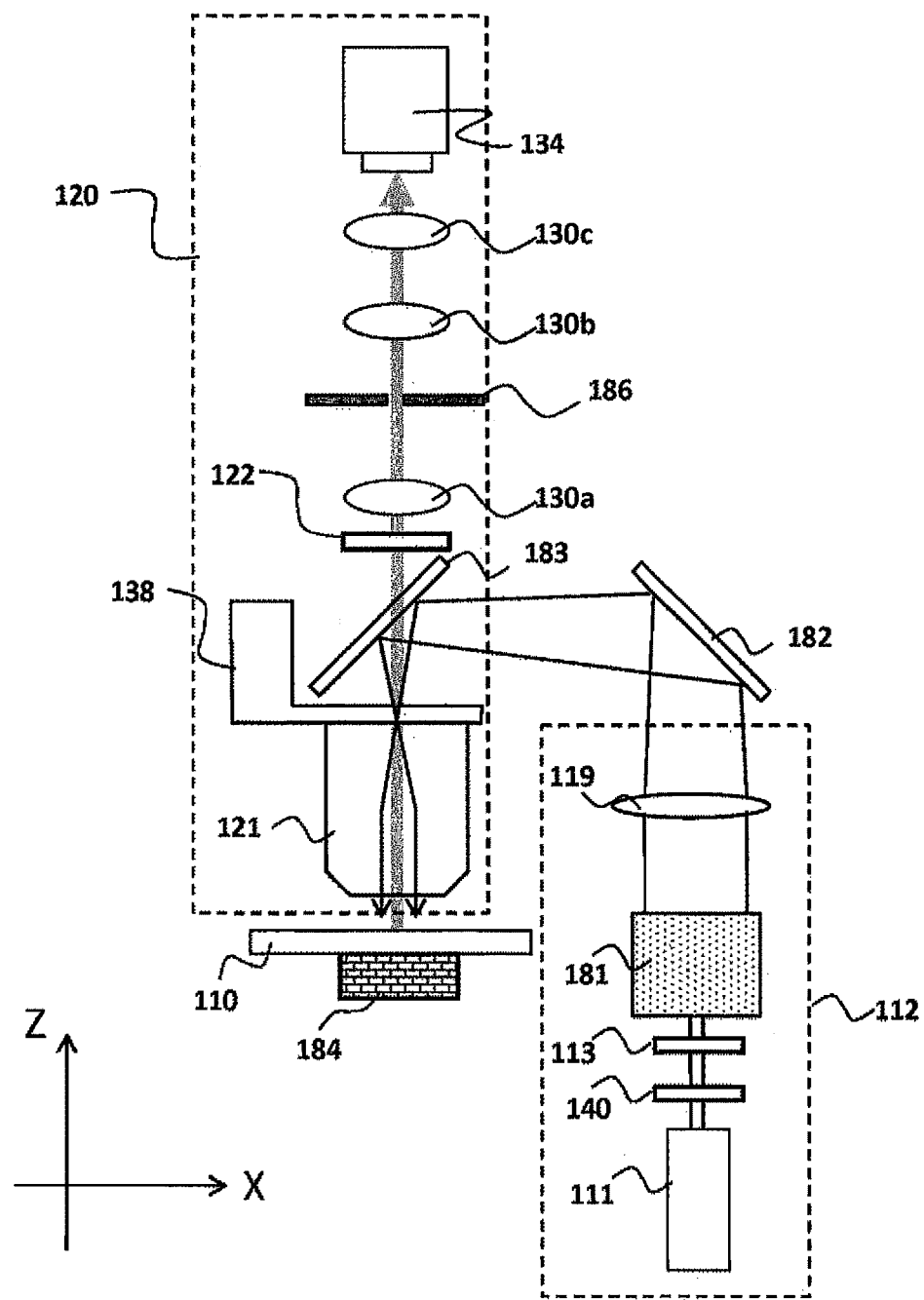

[FIG. 32]
(a)
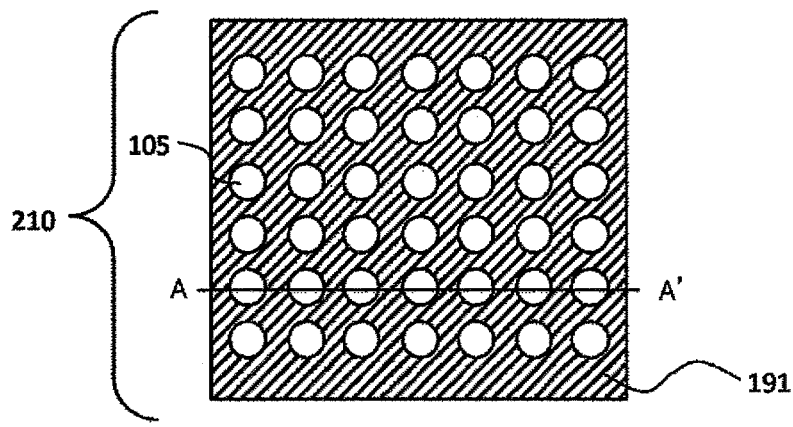
(b)
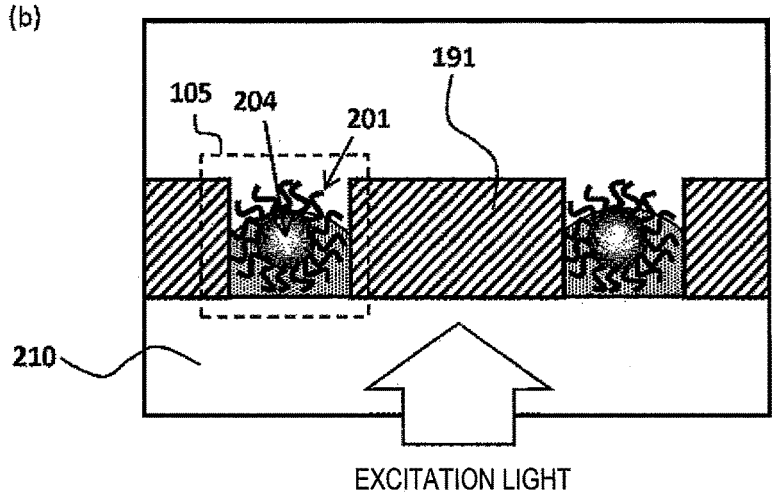
EXCITATION LIGHT
(c)
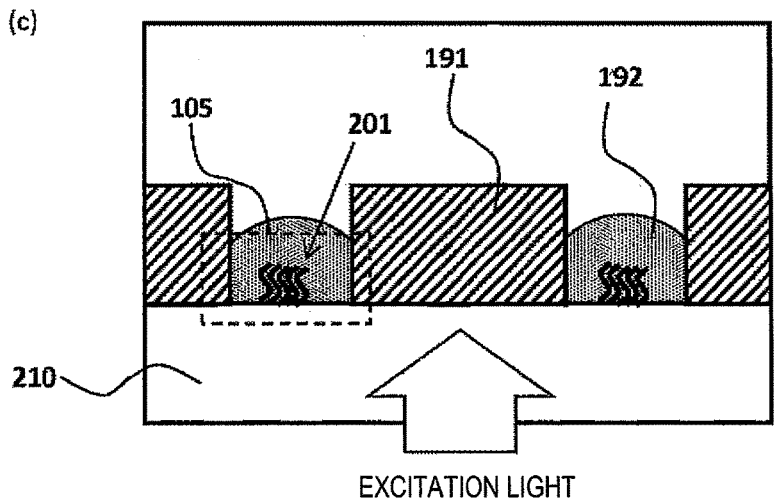
EXCITATION LIGHT

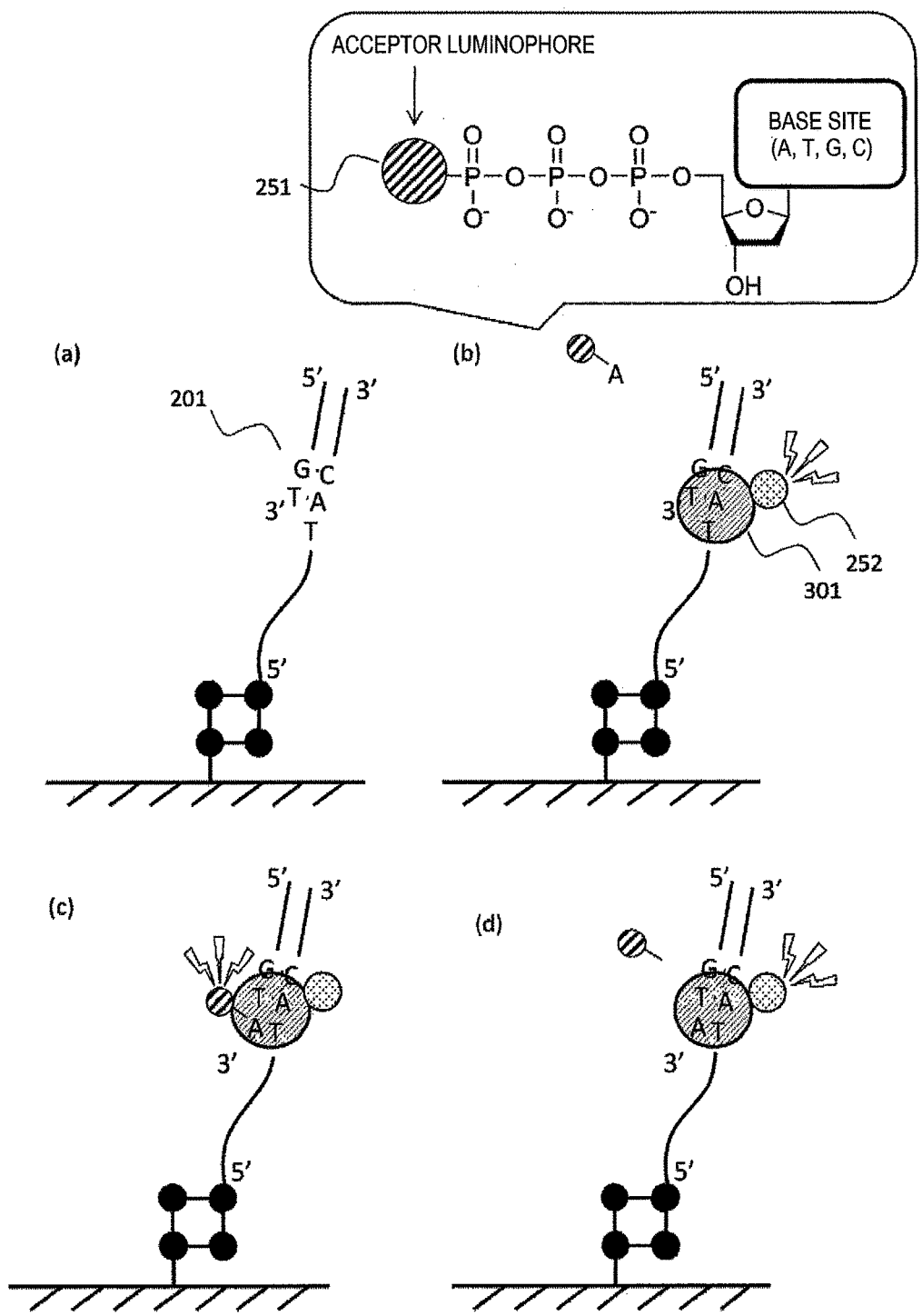
[FIG. 33]

[FIG. 34]
(a)
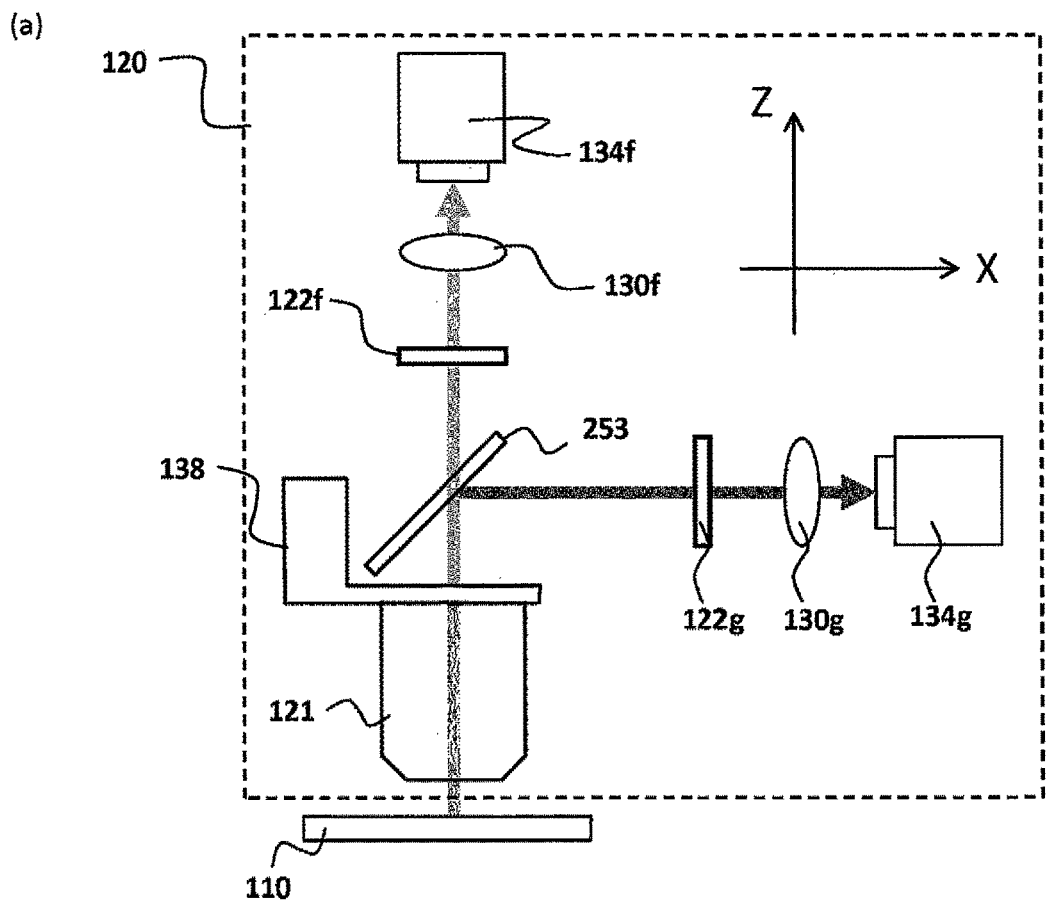
(b)
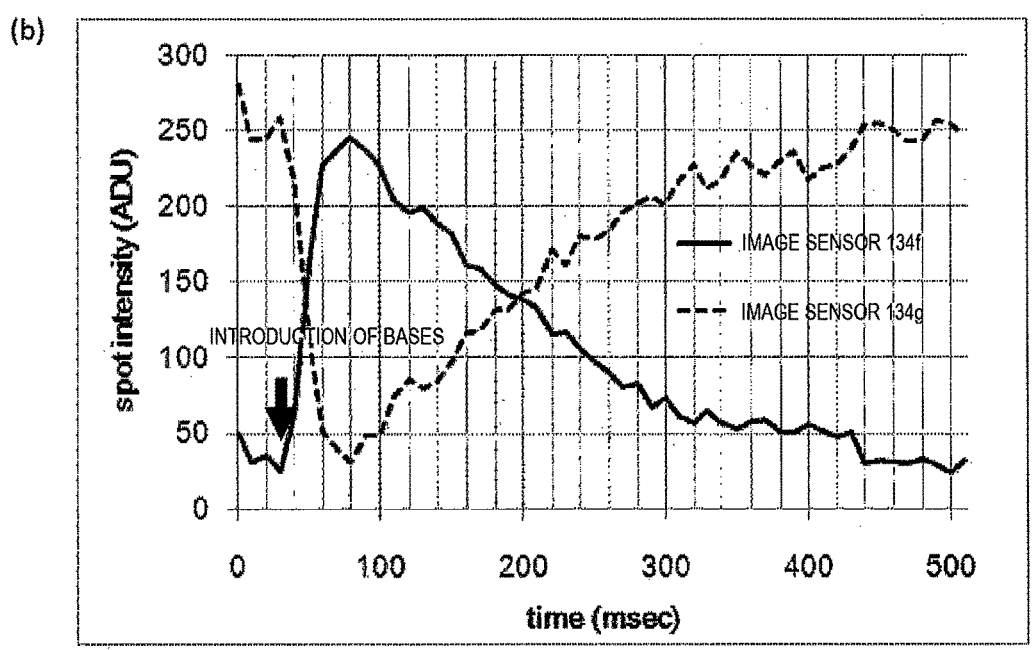

[FIG. 35]
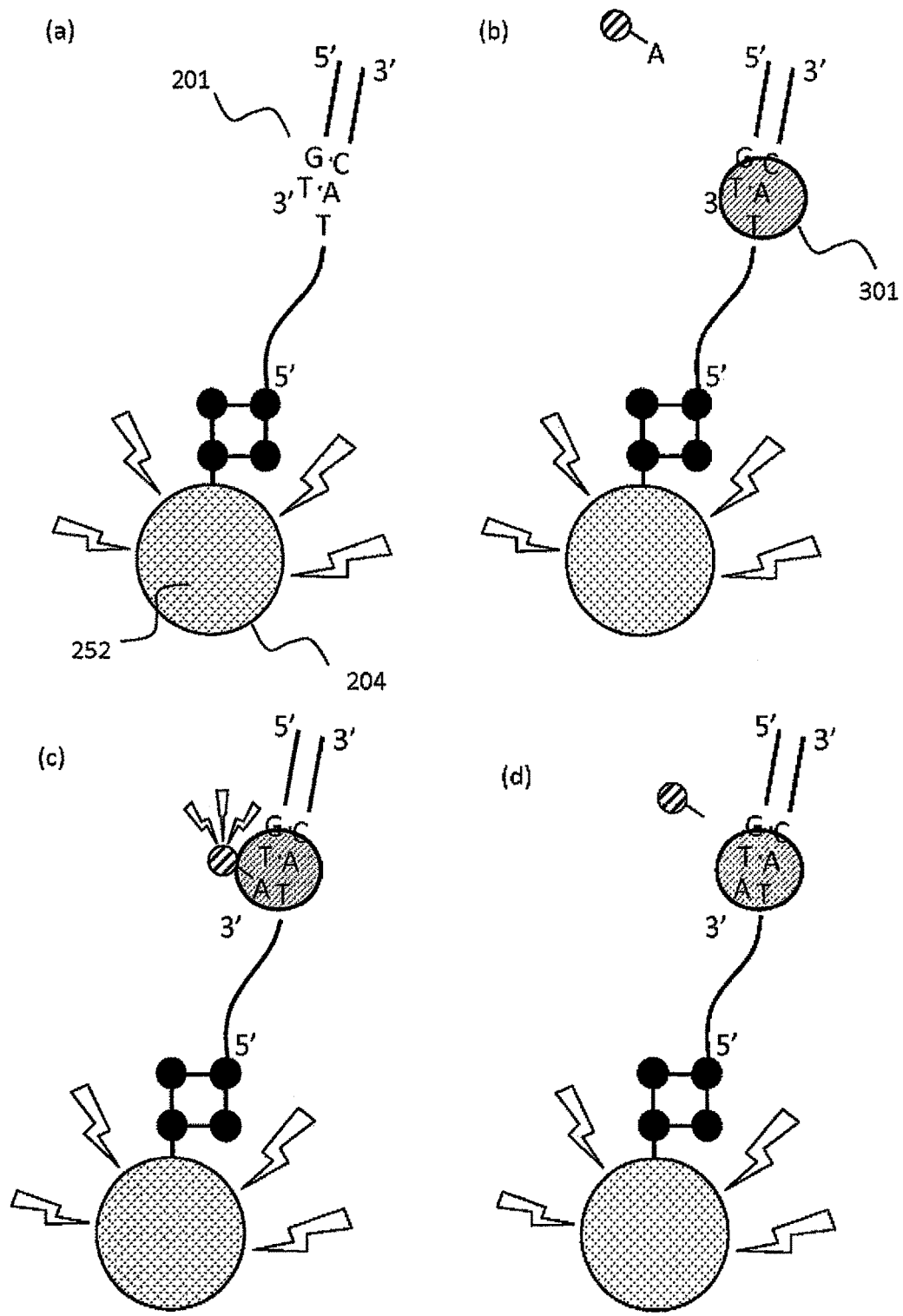

[FIG. 36]
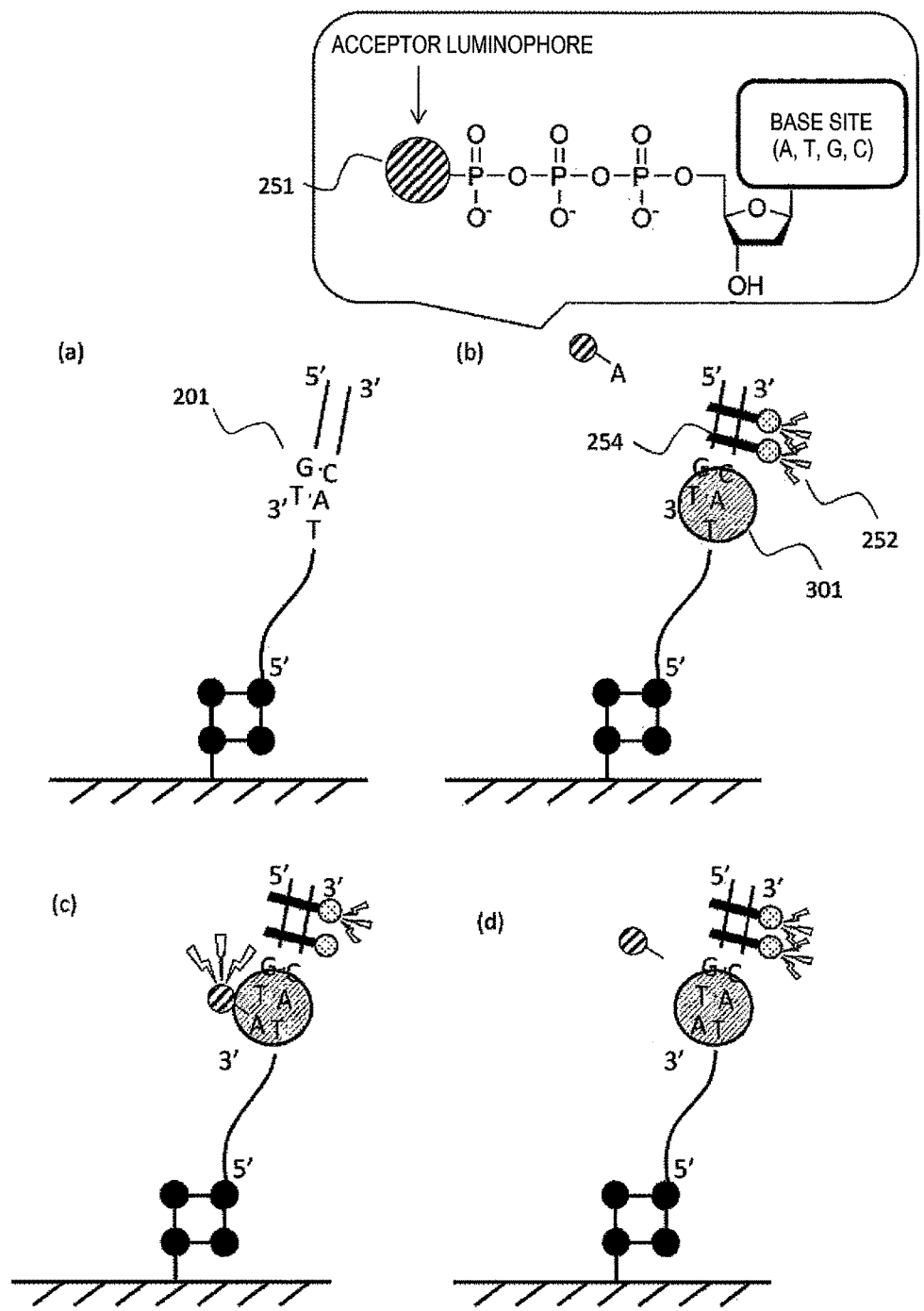

[FIG. 37]
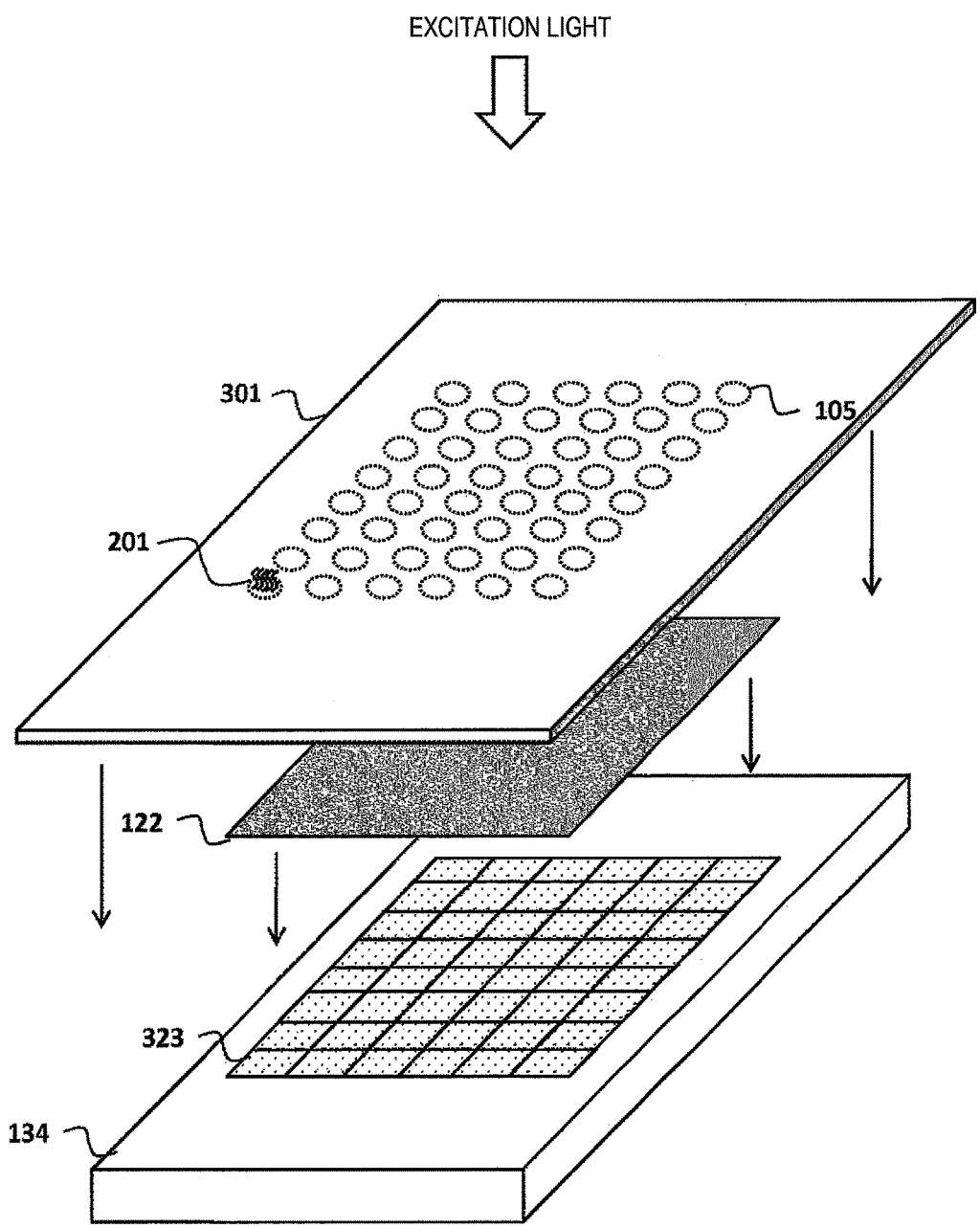

[FIG. 38]
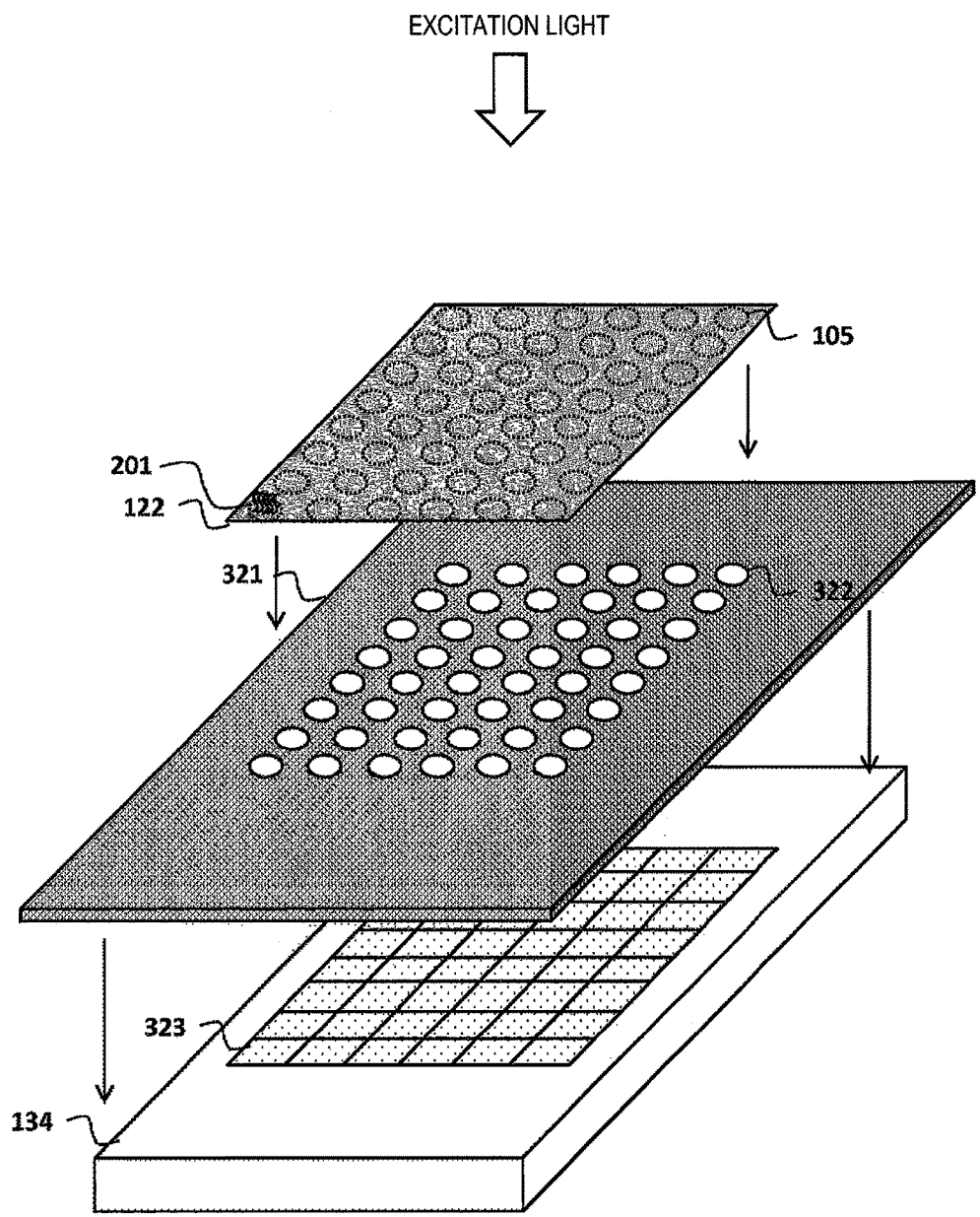

[FIG. 39]
(a)
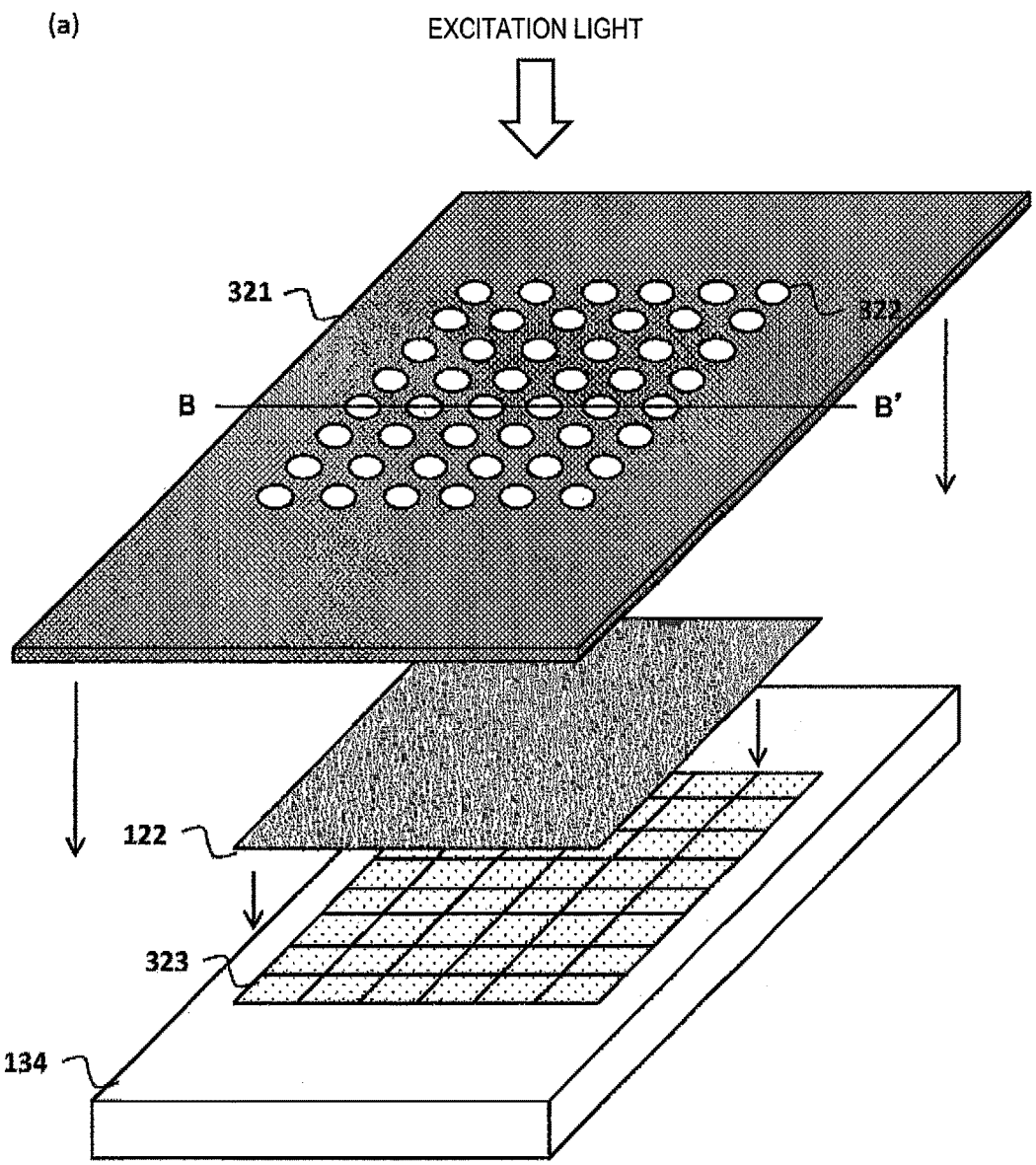
(b) A PART OF BB' CROSS-SECTION
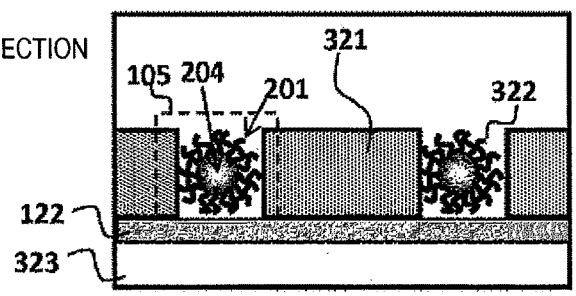

[FIG. 40]
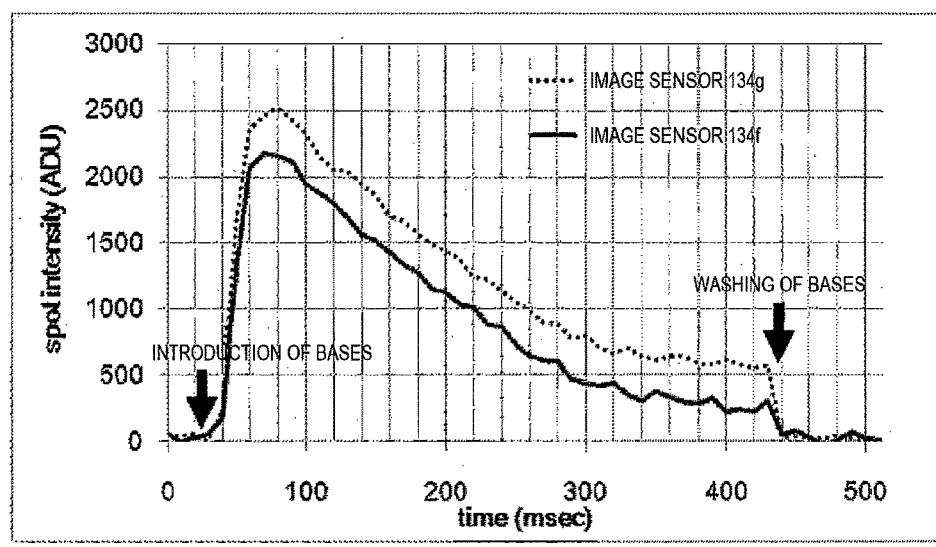

[FIG. 41]
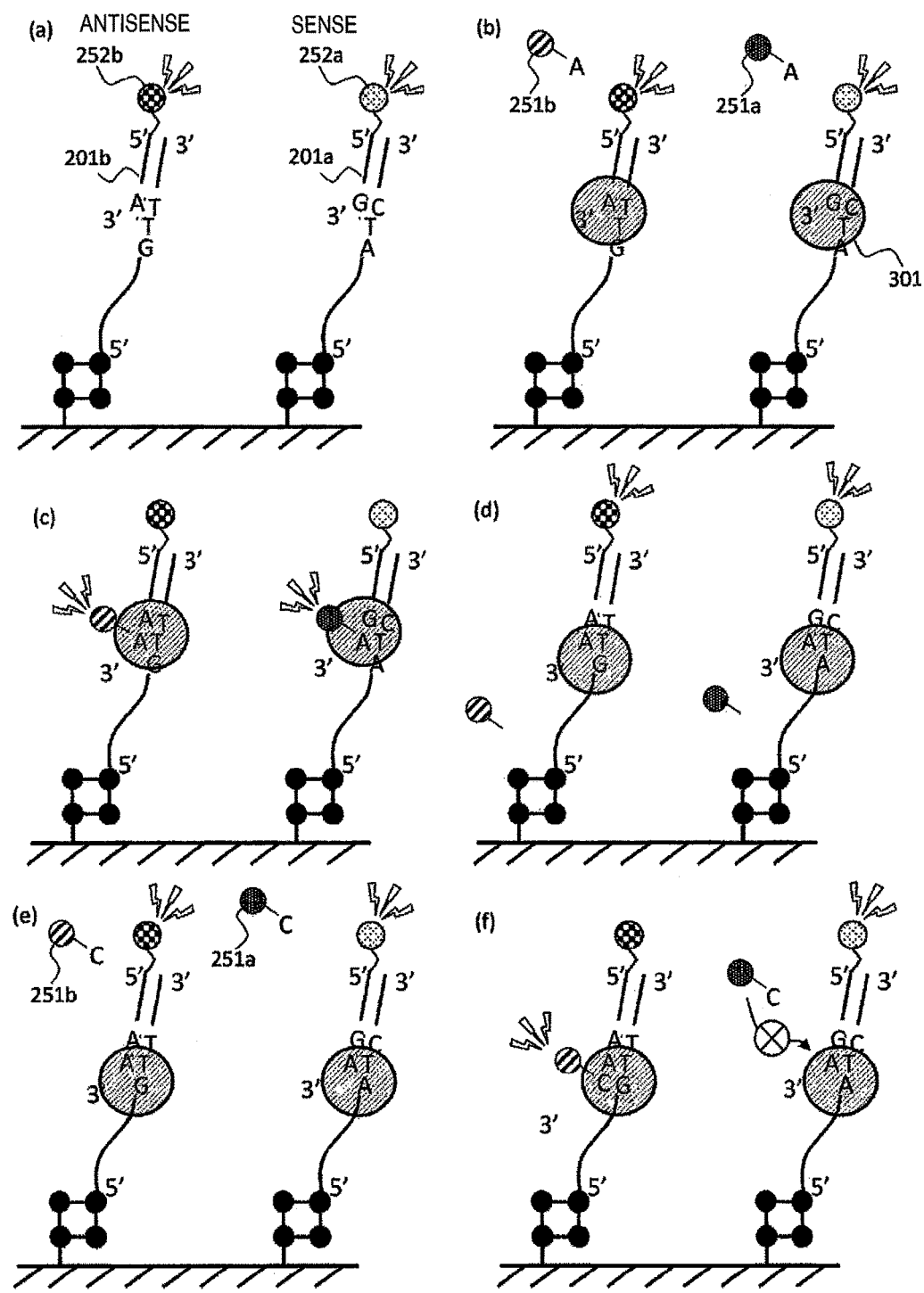

[FIG. 42]
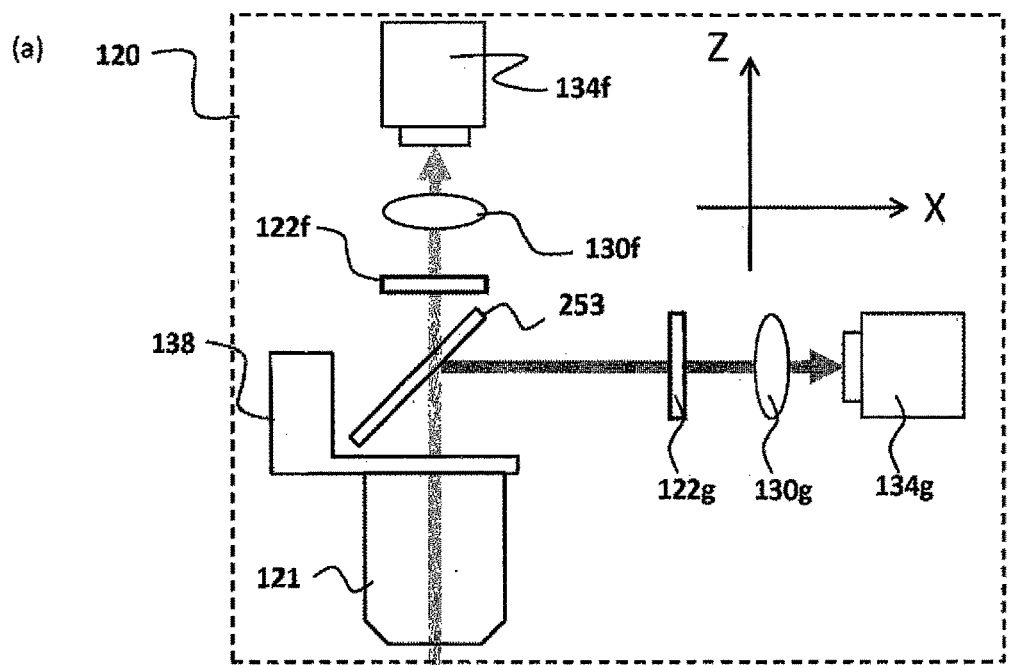
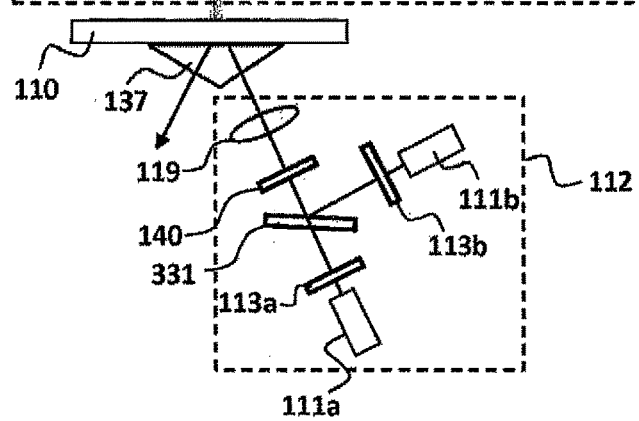
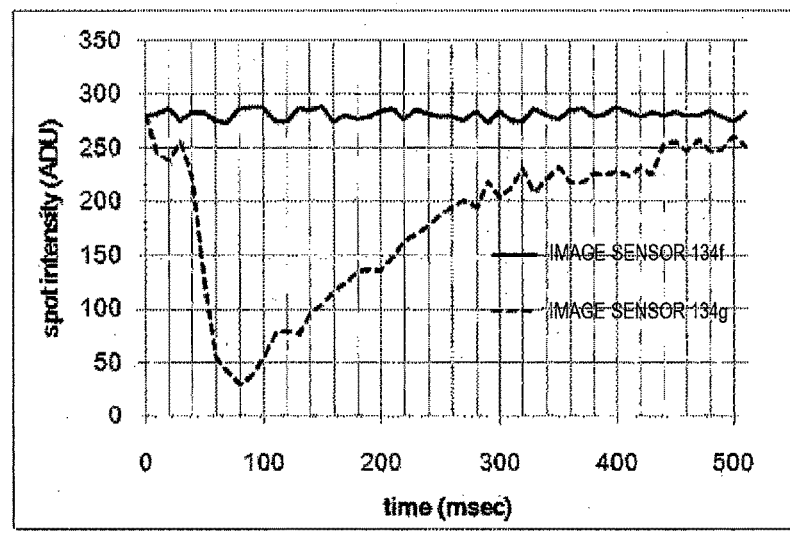

[FIG. 43]
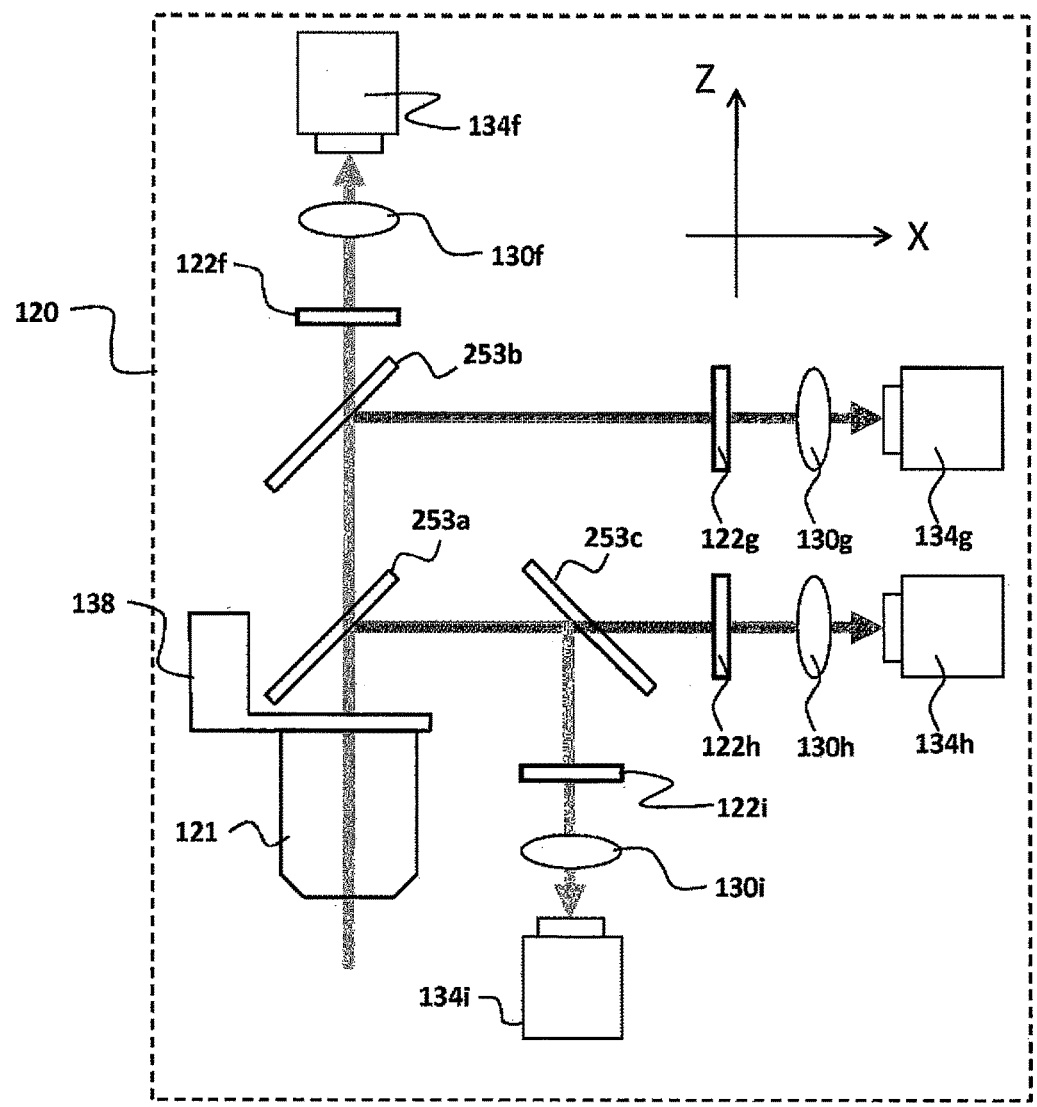

NUCLEIC ACID ANALYSIS DEVICE

TECHNICAL FIELD

The present invention relates to a nucleic acid analysis device.

BACKGROUND ART

Recently, next-generation DNA sequencers have attracted attention as sequencing techniques for DNA nucleotide sequences (DNA sequencing) which have a higher parallel processing capability than DNA sequencers by Sanger method using capillary electrophoresis. Next-generation DNA sequencers achieve ultra-parallel processing by extending DNA fragments to be sequenced spotted highly densely on a substrate and detecting the luminescence of the extension reaction.

NPL 1 discloses a DNA sequencing technique of a next-generation DNA sequencer based on fluorescence detection. Reaction spots in which identical DNA fragments are clustered densely by amplification treatment are arranged highly densely on a glass sample substrate. When four kinds of base (A, T, G and C) labeled with four kinds of fluorophore are introduced to the substrate, a base complementary to that of the DNA fragments is incorporated by extension reaction by polymerase. Because the 3'-terminal of each fluorescently labeled base is modified with a functional group (terminator) for inhibiting the extension reaction, only one base is incorporated in one DNA fragment. After the extension reaction, excess free bases are washed out, and then the fluorescence emitted from each reaction spot is detected as a fluorescent spot and the kind of fluorophore is identified by the color. After the fluorescence detection, the terminator and the fluorophore are removed from each DNA fragment by chemical reaction so that the next base would be incorporated. By repeating the extension reaction, fluorescence detection and removal of the terminator one by one, about 100 bases of the sequence of the DNA fragments are determined.

NPL 2 discloses a DNA sequencing technique of a next-generation DNA sequencer based on detection of chemical luminescence (pyrosequencing). Beads which each have a diameter of about 30 µm wand carry identical DNA fragments fixed thereon by amplification treatment are contained in wells each having a diameter of about 50 µm. A closely packed honeycomb structure of reaction spots having such a well structure is on a sample substrate. The substrate faces an image sensor through optic fibers and is fixed in such a way that the light from a reaction spot is always detected by a same pixel of the image sensor. Although this structure makes sequencing easy, it is difficult to scan two or more fields and process the data in parallel. When a kind of base (for example A) is introduced to a DNA fragment on a bead, the base is incorporated by the extension reaction by polymerase when the complementary base is A. Because the beads are surrounded by a luciferase luminescent agent which emits light by pyrophosphoric acid, the extension can be recognized by detecting the luciferase luminescence emitted from the reaction spots while the extension reaction progresses by the image sensor. Theoretically, the luciferase luminescence amount is in proportion to the amount of pyrophosphoric acid, and thus a luciferase luminescence amount in proportion to the number of incorporated bases is detected in case of a homopolymer. By repeating the above extension reaction for A, T, G and C, around 400 bases of the sequence of the DNA fragments are determined. Because no terminator is used in the above method, it is necessary to introduce the four kinds of base separately to the substrate.

CITATION LIST

Non Patent Literature

NPL 1: D. R. Bentley et al., Accurate whole human genome sequencing using reversible terminator chemistry, Nature 456, 53-59 (2008)

NPL 2: M. Margulies et al., Genome sequencing in microfabricate high-density picoliter reactors, Nature 437, 376-380 (2005)

SUMMARY OF INVENTION

Technical Problem

The next-generation DNA sequencer of NPL 1 has a high parallel processing capacity due to the micro-size reaction spots and the highly dense arrangement thereof, but has its drawback that the read base length is short (100 bases or shorter). This is because of its poor reaction efficiency for removing the terminator, since the terminator is used and the extension reaction is stopped after each base (even if the reaction efficiency is 99%, the signal intensity becomes about ⅓ at 100th base). In addition, when the reaction time is made longer to conduct the removal reaction sufficiently, the sequencing time becomes longer. On the other hand, because the next-generation sequencer of NPL 2 does not use any terminator, a long read base length (400 bases or longer) can be achieved. However, the sequencer has its drawback of poor parallel processing capability for the following two reasons. The first reason is that biochemical luminescence is weaker than fluorescence and thus the sizes of the reaction spots cannot be reduced. The second reason is that scanning is not possible because the lights from the reaction spots should enter the image sensor elements through the optic fibers so that the luminescence from a reaction spot is always detected in the same position of the image sensor. As described above, because biochemical luminescence is weaker than fluorescence, the detection sensitivity thereof is lower than that of fluorescence detection. Accordingly, the sequencing accuracy of the next-generation sequencer of NPL 2 is poor.

As described above, there is no example of a next-generation sequencer which uses fluorescence detection and which can achieve a long read base length, a high parallel processing capability and a high sequencing accuracy at the same time.

Solution to Problem

The invention provides a technique for DNA sequencing by conducting sequential extension reaction without using any terminator and real-time detection of fluorescence. A structure and the means for achieving the technique are as follows:

a nucleic acid analysis device having:

a flowcell in which two or more DNA fragment clusters of two or more DNA fragments having identical nucleotide sequences are immobilized, wherein at least a part of the flowcell is made of a transparent material;

an irradiation unit for irradiating a part in which the DNA fragment clusters are immobilized;

a lens for collecting fluorescence; and a light-detection element for detecting a collected light:

which is characterized in that a solution containing only dATP having a fluorescently modified phosphate terminal among four bases, a solution containing only dCTP having a fluorescently modified phosphate terminal among the four bases, a solution containing only dGTP having a fluorescently modified phosphate terminal among the four bases, a solution containing only dTTP having a fluorescently modified phosphate terminal among the four bases, and a buffer solution for washing out the bases are sent sequentially to the part in which the DNA fragment clusters are immobilized.

Advantageous Effects of Invention

A next-generation DNA sequencer having a long read base length, a high parallel processing capability and a high sequencing accuracy is provided.

BRIEF DESCRIPTION OF DRAWINGS

FIG. 1 shows a device structure of Example 1.
FIGS. 2(a) and 2(b) shows structures on a sample substrate 210 constituting a flowcell 110 of Example 1.
FIG. 3 shows a structure of the flowcell 110 of Example 1.
FIGS. 4(a), 4(b), 4(c) and 4(d) show schematic diagrams of a sequential extension reaction.
FIGS. 5(a) and 5(b) show time-changes in pixel value in pixel positions with reaction spots 105.
FIGS. 6(a) and 6(b) show charts drawn by plotting standardized changes in fluorescence intensity of respective extension reactions, with respect to two reaction spots, namely a reaction spot 1 and a reaction spot 2.
FIG. 7 is a flowchart of a sequencing cycle.
FIG. 8 is a flowchart of base calling of the reaction spots 105.
FIGS. 9(a) and 9(b) show another embodiment 1 of the flowcell and a solution-sending unit.
FIG. 10 is a second embodiment of the flowcell and the solution-sending unit.
FIG. 11 is a structure around the flowcell 110 of Example 2.
FIG. 12 is a flowchart of parallel processing of a sequencing cycle with two or more flow paths.
FIG. 13 is a third embodiment of the flowcell.
FIG. 14 is a fourth embodiment of the flowcell.
FIGS. 15(a) and 15(b) show A structure around a driving unit 761 and the flowcell of Example 3, and a relation of an observation field and the head of a solution, respectively.
FIG. 16 is a flowchart of a sequencing cycle of TDI driving.
FIG. 17 is a flowchart of a sequencing cycle of step driving.
FIGS. 18(a) and 18(b) show another embodiment of the flowcell in Example 3.
FIG. 19 is a structure around the flowcell of Example 4.
FIGS. 20(a) and 20(b) show the principle of a solution-sending method in Example 4.
FIGS. 21(a) and 21(b) show another embodiment of the flowcell in Example 4.
FIG. 22(a) is an example in which two detection units 120 and two irradiation units 112 are provided; and FIG. 22 (b) is another arrangement of the detection units and the irradiation units.
FIG. 23 shows another embodiment of Example 5.
FIG. 24 shows changes in pixel value during the extension reaction of the reaction spots 105, for a case in which non-labeled bases were mixed and a case in which the non-labeled bases were not mixed.
FIG. 25 is an embodiment of the flowcell and the solution-sending unit when non-labeled bases are used after sending respective solutions of fluorescently labeled bases.
FIG. 26 is a flowchart of a sequencing cycle in which non-labeled bases are used after sending respective solutions of fluorescently labeled bases.
FIGS. 27(a), 27(b) and 27(c) show an embodiment of Example 7.
FIG. 28 shows a structure of the irradiation unit and the detection unit of Example 8.
FIG. 29 shows another embodiment of the irradiation unit of Example 8.
FIG. 30 shows another embodiment of the irradiation unit of Example 8.
FIG. 31 shows another embodiment of the detection unit of Example 8.
FIGS. 32(a), 32(b) and 32 (c) show a structure around the sample substrate 210 of Example 9.
FIGS. 33(a), 33(b), 33(c) and 33(d) show schematic diagrams of a sequential extension reaction using fluorescence resonance energy transfer (FRET) in Example 10.
FIG. 34(a) is a structure of the detection unit in Example 10; and FIG. 34(b) shows time-changes in pixel value during an extension reaction of a reaction spot.
FIGS. 35(a), 35(b), 35(c) and 35(d) show another embodiment of Example 10.
FIGS. 36(a), 36(b), 36(c) and 36(d) show another embodiment of Example 10.
FIG. 37 shows a structure around an image sensor 134 and a cover substrate 301 in Example 11.
FIG. 38 shows another embodiment of Example 11.
FIGS. 39(a) and 39(b) show another embodiment of Example 11.
FIG. 40 shows changes in pixel value during extension reaction of a reaction spot 105 measured by image sensors 134g and 134f in Example 12.
FIGS. 41(a), 41(b), 41(c), 41(d), 41(e) and 41(f) show schematic diagrams of a sequential extension reaction using fluorescence resonance energy transfer (FRET) in Example 13.
FIG. 42(a) is a structure of the detection unit and the irradiation unit in Example 13; and FIG. 42(b) shows time-changes in pixel value during an extension reaction of a reaction spot.
FIG. 43 shows another embodiment of the detection unit of Example 13.

DESCRIPTION OF EMBODIMENTS

New characteristics and benefits of the invention are explained below referring to the drawings. In this regard, however, the drawings are solely for the explanations and do not limit the scope of the invention.

Example 1

(Device Structure)
The device structure of Example 1 is shown in FIG. 1. The device is composed of an irradiation unit 112, a flowcell 110, a detection unit 120, a solution-sending unit 104, a controller PC 101 and a waste-fluid tank 102d. First, the irradiation unit 112 and the detection unit 120 are explained in order in which the light travels.

Only when a light-blocking shutter 140 is open, an excitation light emitted from a light source 111 is separated from unnecessary wavelength components by an excitation filter 113 and leaves the irradiation unit 112 while being focused by a condenser lens 119, and the excitation light then enters a total reflection prism 137 perpendicularly. The excitation light which has passed through the total reflection prism 137 passes through a matching material filling the gap between the total reflection prism 137 and a sample substrate 210 constituting the flowcell 110 (FIG. 2) and is completely reflected by the interface between the sample substrate 210 constituting the flowcell 110 and a solution filling on the substrate, and the excitation light then exists from the total reflection prism 137 and enters a terminal. A near field (evanescent field) generated on the surface of the sample substrate 210 by the total reflection excites the fluorophores on the surface of the sample substrate 210. The lights on the substrate are collected by an objective lens 121 in the detection unit 120 and separated from a scattered component of the excitation light by a detection filter 122, and only the fluorescent components pass through an imaging lens 130 and form an image on an image sensor 134 as fluorescent spots. The image sensor 134 successively obtains fluorescent images and sent the data to the controller PC 101.

Specific conditions for Example 1 are as follows, although other conditions are also acceptable: Cy3 was used as the fluorophore, a lens with a numerical aperture of 0.75 (×20) was used as the objective lens 121, and a semiconductor laser which successively oscillates at 532 nm was used as the light source 111. A band-pass filter which transmits only the fluorescence from Cy3 was used as the detection filter 122. A CMOS sensor having a detection element size of 2560×2160 pixels and a pixel size of 6.5 µm was used as the image sensor 134. Because the focal length of the imaging lens 130 is 180 mm and the image magnification is ×20, the observation field is 832×702 µm in size. In order for the evanescent field to surround the observation field, the condenser lens 119 was moved back and forth in the optical axis direction and the size of the excitation beam entering the sample substrate 210 was adjusted. The image sensor 134 obtained fluorescent images with a time interval of 100 Hz.

A Z-axis driving unit 138 is a driving stage for focusing the objective lens 121. The Z-axis driving unit 138 is controlled by the controller PC 101. The Z-axis driving unit 138 can focus automatically using a fluorescent image out of focus. In addition, the driving range is set for each device in order to prevent the objective lens 121 from colliding with the flowcell 110.

The matching material and the terminal are not shown in FIG. 1. Synthetic quartz was used for the total reflection prism 137 and glycerol was used as the matching material. Other transparent materials such as BK7 can be used for the total reflection prism 137. It is appropriate that the matching material be a transparent material having a refractive index between the refractive indexes of the total reflection prism 137 and the sample substrate 210. For example, when PDMA is used as the matching material, the matching material does not drip on the device, resulting in an effect of improving the operability. Provision of the terminal results in an effect of preventing the stray light caused from the excitation light in the device.

The light-blocking shutter 140 is controlled by the controller PC 101 and closed to prevent the excitation light from reaching the sample substrate 210 when fluorescence is not detected. This has an effect of preventing the photodamage of a polymerase 401 (FIG. 4) on the sample substrate 210. Another method which does not use the light-blocking shutter 140 is a method in which the power supply of the light source 111 is turned on and off by switching. This method can achieve a similar effect.

In this Example, total reflection illumination was used to form the evanescent field. This has an effect of inhibiting the background light caused by the excitation of free fluorophores in the solution. In addition to total reflection illumination, oblique illumination has a similar effect. As another illumination method, epi-illumination may be also used.

FIG. 2 shows structures on the sample substrate 210 constituting the flowcell 110. Reaction spots 105 in which identical DNA fragments 201 are clustered together are distributed at random on the sample substrate 210, or the reaction spots 105 may be arranged in lattice. The reaction spots 105 may be beads 204 on which the identical DNA fragments 201 are immobilized as in FIG. 2(a), or may be formed by clusters of the identical DNA fragments 201 as in FIG. 2(b). The individual beads 204 are preferably 500 nm or less in diameter. A method for producing the beads is described in NPL 2. A method for producing the clusters is described in NPL 1. A DNA sequencing method by sequential extension reaction is described below.

FIG. 3 shows a structure of the flowcell 110. The flowcell 110 is an integrated reaction device having five solution inlets 308, one solution outlet 309 and a flow path 311 for sending solutions, and has a structure in which a cover substrate 301, a spacer 306, wherein a part of the spacer is hollowed, and the sample substrate 210 are attached. The flow path 311 is formed by the cover substrate 301, the hollow of the spacer 306 and the sample substrate 210. Reaction solutions are introduced from the solution inlets 308 and discharged from the solution outlet 309. The sample substrate 210 is not limited, but the material thereof is an inorganic material such as glass, sapphire and quartz, or a highly thermally conductive resin material added with carbon fibers or inorganic fillers. The thickness of the sample substrate 210 is not limited, but a thickness of 10 mm or less is desirable to improve the thermal conductivity. The spacer 306 is not limited, but an epoxy adhesive such as thermocurable and photo-curable epoxy adhesives, an acrylic adhesive or the like can be used. A double-sided tape containing an acrylic resin as a base or the like can be also used. A more preferable material is polydimethylsiloxane, which has higher adhesion strength to glass, quartz, sapphire or a transparent resin. As the spacer becomes thinner, the volume in the flow path can be reduced and the amounts of the reagents used can be reduced. In addition, a thickness of 50 µm or less is desirable. It is desirable to use a cover glass material for a fluorescence microscope with a thickness of 0.17 µm for the cover substrate 301.

Although a temperature-regulating mechanism 184 is provided around the flowcell 110, the temperature-regulating mechanism 184 is not shown in FIG. 1. In this Example, the temperature is regulated at 37° C., at which the enzyme reaction is most active. It is possible to bring a metal plate with a Peltier element as the temperature-regulating mechanism 184 into contact with a part of the flowcell 110 except for the light path, or it is also possible to attach a transparent electrically conductive film containing indium tin oxide as the temperature-regulating mechanism 184 to the flowcell 110. Warm wind may be also blown towards the flowcell 110.

The structure of the solution-sending unit 104 is explained. The solution-sending unit 104 is composed of five solution tanks 102a, 102t, 102g, 102c and 102b and solution-sending pumps 103a, 103t, 103g, 103c and 103b. The five solution tanks, the solution-sending pumps and the five solution inlets 308 are connected with pipes. At the command given to the solution-sending pumps from the controller PC 101 connected thereto, one solution-sending pump is driven at a time to send a solution to the flowcell 110. A waste fluid pushed out from the flowcell 110 is discharged from the solution outlet 309 and stored in the waste-fluid tank 102*d*. A buffer solution containing the polymerase 401 and base A having a fluorescently modified phosphate terminal is contained in the solution tank 102*a*. A buffer solution containing the polymerase 401 and base T having a fluorescently modified phosphate terminal is contained in the solution tank 102*t*. A buffer solution containing the polymerase 401 and base G having a fluorescently modified phosphate terminal is contained in the solution tank 102*g*. A buffer solution containing the polymerase 401 and base C having a fluorescently modified phosphate terminal is contained in the solution tank 102*c*. A washing buffer solution only is contained in the solution tank 102*b*. Although the polymerase 401 is contained in the four solution tanks above, the polymerase 401 may be contained in only one of the solution tanks. In addition, a sixth solution tank and a sixth solution inlet may be provided separately. The concentrations of the fluorescently modified bases are desirably 50 to 500 nM. The composition of the buffer solution is 50 mM ACES, pH 7.1, 75 mM, potassium acetate and 5 mM dithiothreitol, 1× protocatechuate dioxygenase, 4 mM protocatechuic acid and 6 mM nitrobenzoic acid (Sigma-Aldrich, St. Louis, Mo.), 0.5 mM manganese acetate, or the like, but a solution capable of conducting enzyme reaction similarly is also acceptable. The above solutions contain a scavenger for removing a dissolved enzyme. By the dissolved enzyme and continuous irradiation with the excitation light, the fluorophores gradually lose their colors. The scavenger has an effect of preventing the discoloration.

The individual fluorophore is attached to a phosphate terminal through a linker. Methods for modifying the phosphate terminals are described in Brent A. Mulder et al., Nucleic Acids Research, 2005, Vol. 33, No. 15, 4865-4873, and Jonas Korlach et al., Nucleosides, Nucleotides and Nucleic Acids, 27:1072-1083, 2008.

(Principle of DNA Sequencing)

FIG. 4 is a schematic diagram of the sequential extension reaction. The extension reaction is explained, focusing on one of the DNA fragments 201 in a reaction spot 105. Before the initiation of the reaction, the DNA fragment 201 is in a state in which a primer is hybridized with a single-strand DNA to be sequenced (FIG. 4(*a*)). The extension reaction progresses from the 3'-terminal of the primer. The surrounding area is filled with the buffer solution. The polymerase 401 and a base (A in the figure) in which the phosphate terminal is labelled with a fluorophore (chromophore) through a linker (the enlarged view of the base structure in FIG. 4 (*b*)) are introduced from the solution tank 102*a* to the substrate (FIG. 4(*b*)). Because base A is complementary to the base (T) next to the 3'-terminal of the primer, the base A is captured by the polymerase 401 and detected as a fluorescent bright point (FIG. 4(*c*)). Then, the phosphate group is removed with the completion of the extension reaction, and the fluorophore thus floats and is not detected as a fluorescent bright point any more (FIG. 4(*d*)). Because there is no terminator, the extension reaction of the DNA fragment 201 progresses when there is the next complementary base. Accordingly, when four kinds of fluorescently labeled base are sequentially introduced to the sample substrate 210 and the increase in fluorescence intensity of the reaction spot 105 is then observed, it means that the DNA fragment has extended. Although the four kinds of base are labeled with Cy3 fluorophores, other fluorophores may be used.

FIG. 5 shows time-changes in pixel value in pixel positions with the reaction spots 105. The chart (a) shows the case when the fragments have extended at the reaction spot 105, while the chart (b) shows the case when the fragments have not extended at the reaction spot 105. In case (a), almost at the same time the fluorescently labeled bases A are introduced to the sample substrate 210, the bases A reaches the reaction spot 105 and the extension reaction progresses. Thus, the pixel value increases rapidly from the pixel value before the introduction of the bases A (called baseline; about 30 ADU) due to the fluorescence from the reaction spot 105. Then, the fluorescence intensity decreases gradually because the number of unreacted DNA fragments reduces, and the pixel value of the reaction spot 105 decreases to the baseline when the bases A are washed out with a washing solution introduced. On the other hand, in case (b), because the extension reaction does not progress, the pixel value increases due to free bases and non-specific binding of the free bases to the reaction spot 105 and then decreases to the baseline simultaneously with the introduction of the washing solution. When the pixel value of the pixel without the reaction spot 105 is set as the background light intensity, the change in fluorescence intensity is i) a value calculated by subtraction of the background light intensity from the maximum pixel value, or ii) a value calculated by subtraction of the integral of the background light intensity over the period from the introduction of the bases to washing out of the bases from the integral of the pixel intensity over the same period. It can be recognized that the extension reaction has progressed when the change in fluorescence intensity exceeds the threshold.

FIG. 6 contains charts drawn by plotting the standardized changes in fluorescence intensity for respective extension reactions, with respect to two reaction spots, namely a reaction spot 1 and a reaction spot 2. Although only five extension reaction cycles of A, T, G and C are shown in the charts, 100 or more extension reaction cycles are conducted. The standardization was conducted by multiplying the change in fluorescence intensity during each extension reaction by the change in fluorescence intensity during single-base extension. In case of a homopolymer, because an intensity change of several-fold of the number of the extended bases is obtained, the vertical axis of the charts corresponds to the extended base number. In FIG. 6, the numbers of extended bases are indicated over the histogram bars for the cases in which the changes in fluorescence intensity exceeded the thresholds.

(Flowchart of DNA Sequencing)

FIG. 7 is a flowchart of the extension reaction cycle. The extension reaction cycle is a process for obtaining fluorescent images for DNA sequencing. The entire flow is automatically controlled by the controller PC 101. This flowchart is on the assumption that the reaction spots 105 as shown in FIG. 2 are formed on the sample substrate 210 filled with the buffer solution. According to this flowchart, the extension reaction cycle is conducted.

Supplemental explanations for each step in the flowchart are as follows: the fluorescent spots shown in the step 603 are fluorescent images of the fluorescence from the reaction spots 105. The threshold Th1 in the step 603 was as follows: Th1=(average of all pixel values)+4×(standard deviation of all pixel values). In the step 604, Th0 is a threshold for determining that the extension reaction has been finished. Although Th0=0.1 here, an optional value can be set. Although the "average of three successive frames" is used for the condition, the number of the frames may be two or less, or four or more. Although the solution is sent until the condition "average derivative of three successive frames<Th0" is met in the step 605, the solution sending may be stopped as long as the solution in the flowcell 110 is sufficiently replaced with that from the solution tank 102i in the step 601. In this regard, however, continuous sending of the solution has an effect of preventing non-specific adsorption. In addition, the flow of the solution sent can lay the DNA fragments 201 and bring the DNA fragments 201 close to the surface of the sample substrate 210. From this, the DNA fragments 201 can be placed in the evanescent field where the excitation intensity is high, resulting in an effect of increasing the fluorescence intensity. When the time required until "average derivative of three successive frames<Th0" is met is known in advance, the steps 603 to 605 may be skipped and the images may be obtained for a certain period of time from the initiation of solution sending.

FIG. 8 is a flowchart of base calling of the reaction spots 105. In accordance with this flowchart, the fluorescent images obtained in the sequencing cycles were analyzed and the nucleotide sequence of each reaction spot 105 was determined.

(Other Embodiments of Flowcell and Solution-Sending Unit)

Embodiments of the flowcell 110 and the solution-sending unit 104 other than the above embodiments are shown. FIG. 9 is another embodiment 1 of the flowcell 110 and the solution-sending unit 104. The solution in the flow path 311 is sucked with a pump 901 interposed between the solution outlet 309 and the waste-fluid tank 102d and a solution is thus sent. Because the number of pump can be reduced to one in this method, the cost can be cut. In FIG. 9 (a), the embodiment is characterized in that the solution tanks 102a, 102t, 102g, 102c and 102b have switching valves 902a, 902t, 902g, 902c and 902b, respectively. The flow paths from the five solution tanks 102 are combined into one flow path at a flow path connector 903 and connected to one solution inlet 308. The pump 901, and the switching valves 902a, 902t, 902g, 902c and 902b are connected to the controller PC 101 and the timing for sending the solutions is controlled automatically. In FIG. 9(b), the embodiment is characterized by having a changeover valve 904. The changeover valve 904 is connected to the controller PC 101 and is controlled automatically in such a way that one of the solutions in the solution tanks 102a, 102t, 102g, 102c and 102b is sent to the solution inlet 308. Because the number of valve is reduced to one, this embodiment has an effect of simplifying the structure.

FIG. 10 shows another embodiment 2 of the flowcell 110 and the solution-sending unit 104. Because the solutions are sent using a nozzle 720, the number of the pipes can be reduced, resulting in an effect of simplifying the structure of the flowcell 110 having two or more flow paths. Although an example with three flow paths is shown in FIG. 10, the number of the flow paths may be two or less, or four or more. The solutions are sent by the following method. It is assumed here that a flow path 311a is in the observation field of the objective lens 121. The nozzle 720 accesses one of the solution tanks 102a, 102t, 102g, 102c and 102b and a reagent is sucked with a solution-sending unit 719. The nozzle 720 is moved over the flowcell 110 by a nozzle-moving unit 721 and connected to a solution inlet 308a to introduce the reagent. The waste fluid pushed out from the flow path 311a is discharged from a solution outlet 309a into the waste-fluid tank 102d. Then, the nozzle 720 leaves the solution inlet 308a and sends the solutions from the other solution tanks by repeating the solution-sending cycles of accessing/sucking/moving/introducing. When DNA sequencing in the flow path 311a is finished, the flowcell 110 is moved in the Y-axis direction by a driving unit 712 and a flow path 311b is moved to the observation field of the objective lens 121. DNA sequencing is conducted by carrying out a similar solution-sending operation. By repeating this operation with respect to a flow path 311c, DNA sequencing in the three flow paths can be conducted sequentially. The above operations are controlled automatically by the controller PC 101. In order to simplify the explanation, the components of the detection unit 120 except for the objective lens 121 are not shown in FIG. 10. Although one nozzle 720 is used in the above example, the solutions may be sent by two or more nozzles aligned in parallel using two or more solution inlets for each flow path. Because a nozzle can introduce a regent while another nozzle is accessing/sucking/moving, this case has an effect of shortening the time of the solution-sending cycles.

Example 2

FIG. 11 shows a structure around the flowcell 110 of Example 2. The other components are the same as in Example 1. Example 2 is characterized in that two or more flow paths are aligned and the flow paths are processed in parallel by synchronizing solution sending and driving of the flowcell 110. This has an effect of increasing the number of parallel processing.

The flowcell 110 has two or more flow paths 311. The flowcell 110 is fixed on a driving unit 731 and can move the flow paths to the observation field of the objective lens 121 one after another. Although the solution-sending unit 104 shown in FIG. 9 is connected to each flow path of the flowcell 110, the solution-sending units 104 are not shown in the figure. In this Example, the embodiment of the flowcell 110 and the solution-sending unit 104 is an embodiment in which two or more structures shown in FIG. 9 are aligned, but the other structures of the flowcell 110 and the solution-sending unit 104 shown in Example 1 can be used. Although 10 flow paths are aligned in parallel in FIG. 11, the number thereof may be more than 10 or less than 10.

According to the flowchart of parallel processing of an extension reaction cycle with two or more flow paths in FIG. 12, the controller PC 101 automatically sends the solutions, obtains images and drives the flowcell 110. Supplemental explanations for this flowchart are as follows: in the step 616, because the frame showing the maximum value varied with the position of the reaction spot 105, the time difference was set at three frames and the acquisition of images was stopped after ((frame showing maximum value)+3 frames). This time difference is in proportion to the time required to completely fill the flow path with a solution. The larger the observation field, the larger the number of frames from the frame showing the maximum value to the frame at which the acquisition of the images is stopped. The number of frames can be set at an optional value as long as the likelihood is 1 or more. In the step 617, t1=0.3 sec and t2=1.0 sec in this Example. t1 is the period from the time showing the maximum value to the completion of the extension reaction. In the example of FIG. 5, the maximum value was around 90 msec and the extension reaction was completed at around 400 msec, and thus t1=0.3 sec in view of the difference thereof (310 msec). It is appropriate that t2 be longer than the time required to replace the solution in the flow path with the solution in the solution tank 102b. In this regard, however, it is desirable that the replacement of the solution is completed before the next extension reaction. When the period from the initiation of the solution sending to the time showing the maximum value (this period is referred to as t0) is known in advance, the steps 613 and 614 may be skipped and the solution sending in the step 611 and the acquisition of the images in the step 612 may be conducted for the period t0.

(Other Embodiments of Flowcell)

Embodiments of the flowcell 110 other than the above embodiments are shown. FIG. 13 shows another embodiment 3 of the flowcell 110. Two flowcells 110 are aligned on a driving unit 741. The driving unit can be driven in the X and Y directions. By driving the driving unit 741 in order of (1) to (4) in FIG. 13 in such an embodiment, an effect of reducing unnecessary driving upon scanning the surfaces of the flowcells 110 is achieved. FIG. 14 is another embodiment 4 of the flowcell 110. The flowcell 110 has a disk shape with a hollow. The flowcell 110 is fixed on a rotary driving unit 751. In the hollow of the flowcell 110, the solution tanks 102a, 102t, 102g, 102c and 102b are on the rotary driving unit 751. By rotating the rotary driving unit 751, the flow paths 311 can be moved to the observation field of the objective lens 121 one after another. Although the components such as the pipes connecting the solution tanks and the inlets 308, and the pumps are not shown in the figure, these components are the same as those in FIG. 1. In FIG. 14, the waste-fluid tank 102d is separated from the flowcell 110 in the direction of the outline arrow for the purpose of explanation. A pipe 752 is attached to each of the solution outlets 309 and the waste fluids drip through the pipes to the waste-fluid tank 102d. The waste-fluid tank 102d is separate from the rotary driving unit 751 and thus does not rotate. The structure of FIG. 14 also has an effect of reducing unnecessary driving upon scanning the surface of the flowcell 110.

Example 3

FIG. 15(a) shows a structure around a driving unit 761 and the flowcell 110 of Example 3. The other components are the same as the components in the Examples above. The characteristics of this Example are that the driving unit 761 is driven at the same speed as the speed (flow rate) of the surface of a solution containing bases from the solution tank 102a, 102t, 102g or 102c moving in the flow path but in the opposite direction, and thus the part near the interface of the solution moving in the flow path is located right under the observation field of the objective lens 121 and two or more fields are detected. This method has an effect of increasing the number of parallel processing. In addition, because two or more fields can be detected in each flow path, this method has an effect of making the amount of the reagent for each field very low.

As the method for obtaining images by the image sensor 134, a method in which images are obtained successively with a charge-transfer direction and a speed corresponding to those of the driving unit 761 (Time Delay Integration; TDI) is effective. Because the gap between adjacent observation fields can be minimized, this method has an effect of using the area of the flow path 311 effectively. The relation of the observation field and the interface of a solution moving in the flow path above in case of TDI driving is shown in FIG. 15 (b). It is preferable that the solution interface is as close to the edge of the scanning direction side of the observation field as possible. This has an effect of shortening the scanning time. FIG. 16 is a flowchart of a sequencing cycle of TDI driving. It is not always necessary to conduct the step 1603 before the step 1604. The obtained images may be stored in a recording medium and the step 1603 may be conducted after the extension reaction cycles.

The flowcell 110 may be driven by step driving of each field. This case should follow the flowchart of an extension reaction cycle of step driving in FIG. 17. In the step 1606, t1 should be longer than the period from the initiation of the extension reaction in a position in the field where the solution reaches the latest to the time when the maximum pixel value is observed. In this Example, t1=0.4 seconds. t1 is set in accordance with the field size and the speed for sending the solutions.

In the two flowcharts above (FIGS. 16 and 17), the driving unit 761 is driven to move to an observation field 1 simultaneously with the initiation of the introduction of the buffer solution in the solution tank 102b (1604 or 1608). This has an effect of shortening the measurement time. In this regard, however, the initiation of the introduction of the buffer solution may be before the completion of the acquisition of the image of the last field. As long as the reaction time sufficient for finishing the extension reaction in all the fields is ensured, it is possible to start introducing the buffer solution at any time. The observation field may be moved by driving the detection unit 120 as well as by moving the flowcell 110.

(Other Embodiments of Flowcell)

FIG. 18 shows another embodiment of the flowcell 110 in Example 3. This embodiment is characterized in that the flowcell 110 has two or more flow paths and the solution-sending directions of adjacent flow paths are opposite. FIG. 18 shows an example of two flow paths. In this example, while a solution containing bases flows through the flow path 311a and the fluorescence by the extension reaction is detected, the buffer solution flows through the flow path 311b in the direction opposite to that in the flow path 311a and unreacted bases are discharged (the step 1 in FIG. 18). When the fluorescence detection of the extension reaction in the flow path 311a is completed up to the last field, the driving unit 761 is driven in the X-axis direction to move the observation field to the field 1 of the flow path 311b and the fluorescence of the extension reaction is detected. During this time, the buffer solution flows through the flow path 311a to discharge unreacted bases (the step 2 in FIG. 18). This embodiment has an effect of shortening the driving time of the flowcell 110. The observation field may be moved also by driving the detection unit 120.

Example 4

FIG. 19 shows a structure around the flowcell 110 of Example 4. The other components are the same as the components of the Examples above. The characteristic of Example 4 is that the solutions are sent using electrophoresis. The flowcell 110 of FIG. 19 has the solution tanks 102a, 102t, 102g, 102c and 102b and electrodes 153 can be immersed in the solution tanks. The electrodes 153 are immersed by turning on electrode switches 151. The electrodes are connected with a wire 152 and a power supply 150 for applying a voltage to the electrodes 153 is provided in the middle of the wire. Two tanks are provided for storing each of the solutions in the solution tanks 102a, 102t, 102g and 102c. FIG. 20 shows the principle of the solution-sending method in Example 4. As shown in FIG. 20(a), by applying a voltage to a solution tank 2 and a waste-fluid tank 4 after applying a voltage to solution tanks 1 and 3, the reagent in the solution tank 1 can be sent to the flow path connecting the solution tanks 2 and 4. In order to increase the amount of the solution to be sent, the flow path between the solution tanks 1 and 2 should be T-shaped, as shown in FIG. 20(b). This solution-sending method is called a cross-injection method and the details thereof are described in Shaorong Liu et al., Anal. Chem. 1999, 71, 566-573. By the method, it is possible to send the extension reaction reagents containing small amounts of the labeled bases and the buffer solution in the solution tank 102b to the observation field of the objective lens 121 one after another in FIG. 19. By this, the solutions can be exchanged quickly. This Example has an effect of making the amounts of the reagents very low and shortening the solution-sending time.

(Other Embodiments of Flowcell)

FIG. 21 shows another embodiment of the flowcell 110 in Example 4. The flowcell 110 has two or more flow paths and a driving unit 154 for moving the flowcell 110. Solutions are sent in adjacent flow paths in such a way that the timing for washing with the buffer solution and the timing for sending an extension reaction reagent are shifted. Although FIG. 21 shows two flow paths, the number of the flow paths may be three or more. In FIG. 21(a), the extension reaction reagent in the solution tank 102a is sent to the observation field of the objective lens 121 in the flow path 311c and the fluorescence of the extension reaction is detected (the step 1 of FIG. 21 (a)). After the completion of the detection, the driving unit 154 is moved in the X-axis direction and the observation field is moved to the flow path 311d (the step 2 of FIG. 21(b)). At the time when the move is completed, the extension reaction reagent in the solution tank 102a reaches the observation field in the flow path 311d and the detection of the fluorescence of the extension reaction starts. On the other hand, in the position in the flow path 311c where there has been the observation field, unreacted bases are washed out with the buffer solution. By repeating the steps 1 and 2, parallel processing of the two observation fields is possible without waiting for the time required for washing out the unreacted bases with the buffer solution. Accordingly, this embodiment has an effect of increasing the throughput.

Example 5

This Example is characterized by having two or more detection units 120 and irradiation units 112. FIG. 22(a) shows an example having two detection units 120 and two irradiation units 112 for processing the flowcell 110 having a structure including two or more flow paths in FIG. 11 in parallel. All the components of the detection units 120 and the irradiation units 112, except for the objective lenses 121, are not shown in the figure. By processing with the two detection units 120 and the two irradiation units 112 in parallel according to the flowchart shown in FIG. 12, this example has an effect of increasing the throughput. FIG. 22(b) shows another alignment of the detection units 120 and the irradiation units 112. Although the effect of this Example can be obtained by both of the alignments (a) and (b), the alignment (a) has an effect of reducing the driving range of scanning. In the alignment (a), the detection units 120 and the irradiation units 112 are placed for the first and sixth flow paths among 10 flow paths (only objective lenses 121a and 121b are shown in the figure). In this case, when the distance between the flow paths is L mm, the flowcell 110 should be moved by the driving unit 731 only by 4 L mm in order to scan all the flow paths. On the other hand, in case of (b), 8L mm is necessary to scan all the flow paths.

FIG. 23 shows another embodiment of this Example. Two detection units 120 and two irradiation units 112 are provided for the flow path of FIG. 19 (only objective lenses 121c and 121d are shown in the figure). As in this embodiment, it is possible to provide two or more detection units 120 and irradiation units 112 for one flow path.

Although two examples are shown above, a combination with any of the Examples above is possible. In addition, although examples in which two detection units 120 and two irradiation units 112 are provided are shown in the examples, the numbers thereof may be three or more.

Example 6

This Example is characterized in that non-labeled bases are used for the extension reaction. The non-labeled bases are used for the extension reaction after mixing with the respective fluorescently labeled bases or used after sending the respective solutions of the fluorescently labeled bases. The flowchart of the sequencing cycle in the case of using for the extension reaction after mixing with the fluorescently labeled bases is the same as the flowchart described in the Examples above. In this regard, however, the solution tanks 102a, 102t, 102g and 102c contain non-labeled bases corresponding to the respective kinds of labeled base. In this Example, the fluorescently labeled bases and the non-labeled bases were mixed with a concentration ratio of 30:1. FIG. 24 shows changes in pixel value during the extension reaction of the reaction spots 105, for the case in which the non-labeled bases were mixed and the case in which the non-labeled bases were not mixed. The reaction efficiency of non-labeled bases is higher than that of labeled bases. Thus, in the case with non-labeled bases, the extension reaction in the reaction spot 105 progresses faster, the increase in the fluorescence intensity of the extension reaction is small and the decay is also faster. There are two or more DNA fragments having identical nucleotide sequences in the reaction spots 105.

Although a sufficient time is required for extending the DNA fragments entirely with the labeled bases only, the use of the non-labeled bases can increase the extension reaction speed. Thus, an effect of shortening the DNA sequencing time is achieved and the read length can be increased due to the improved reaction yield.

When the non-labeled bases are used after sending the respective solutions of the fluorescently labeled bases, solution tanks 162a, 162t, 162g and 162c containing the non-labeled bases only are provided as shown in FIG. 25. A buffer solution containing non-labeled bases A is contained in the solution tank 162a. A buffer solution containing non-labeled bases T is contained in the solution tank 162t. A buffer solution containing non-labeled bases G is contained in the solution tank 162g. A buffer solution containing non-labeled bases C is contained in the solution tank 162c. FIG. 25 shows the structure of FIG. 9(b) with an addition. The structure is the same as that in FIG. 9(b), except that the number of the solution tanks is increased and that a change-over valve 904b has a function capable of switching the solutions sent from the nine solution tanks. The flowchart of the extension reaction cycle using this structure is shown in FIG. 26. When the period from the initiation of the solution sending to the time showing the maximum value (the period is referred to as t0) is known in advance in the step 173, the steps 173 and 174 may be skipped and the solution sending in the step 171 and the acquisition of the images in the step 172 may be conducted for the period t0. In this Example, the concentrations of the non-labeled bases were 10 µM, each solution was sent for t4=0.5 seconds, and t5=1 second. The values may be changed optionally. In general, because the fluorescence intensity sometimes becomes weaker at the late stage of the reaction cycles of DNA sequencing, the decrease in the intensity can be prevented by setting t5 long in the early stage and setting t4 long in the late stage. When the non-labeled bases are used after sending the respective solutions of the fluorescently labeled bases, the extension reaction time can be shortened and also the extension reaction progresses efficiently with the labeled bases at a high concentration, resulting in the reduction of amount of the unreacted DNA fragments. That is, phase shifts due to the unreacted DNA fragments are prevented, resulting in an effect of increasing the read length.

Example 7

This Example is characterized by moving the observation field between two places and repeating the acquisition of images alternately. FIG. 27 shows an embodiment of this Example using the structure of FIG. 11 of Example 2. In FIG. 27(a), an image is obtained while the observation field of the objective lens 121 is over the flow path 311d (step 1). Then, as shown in FIG. 27(b), the flowcell 110 is driven in the Y direction by the driving unit 731 and the observation field is moved to the flow path 311e, and then an image is obtained (step 2). By repeating the steps 1 and 2, the changes in fluorescence intensity of the extension reaction in the flow paths 311d and 311e are measured alternately. FIG. 27(c) shows the changes in intensity of the same pixel measured by the above method. The increases in pixel value, which indicate the extension reaction, are observed because there are reaction spots 105 in this pixel location in both of the two flow paths. The maximum values of the two flow paths can be calculated by curve fitting of the plotted values. Although the observation field is moved between two flow paths in the example above, the number of the flow paths may be three or more. In addition, this Example may be combined with the embodiments other than those in Example 2.

In general, the same numbers of the detection units 120 and the irradiation units 112 as that of the observation fields are necessary to process two or more observation fields in parallel, however, two or more fields can be processed in parallel with one detection unit 120 and one irradiation unit 112 according to this Example. Therefore, this Example has an effect of cutting the device cost.

Example 8

FIG. 28 shows a structure of the irradiation unit 112 and the detection unit 120 of Example 8. This structure is characterized in that a light from the light source 111 is applied to the flowcell 110 from the side of the detection unit 120 (coaxial illumination). This has an effect of providing a space behind the flowcell 110, at the side opposite to the detection unit 120. In FIG. 28, the temperature-regulating mechanism 184 was provided in this space and the temperature of the flowcell 110 was kept at a temperature at which the extension reaction progressed efficiently. A Peltier element was used for the temperature-regulating mechanism 184 and the temperature during the extension reaction was set at 37° C., but other temperature-regulating mechanisms 184 and other temperature settings are acceptable. Köhler illumination was used for the illumination method in FIG. 28. A semiconductor laser continuously oscillating at 532 nm was used as the light source 111. When the light-blocking shutter 140 is open, the excitation beam from the light source 111 is separated from unnecessary wavelength components by the excitation filter 113, followed by expansion of the beam size by a beam expander 181, reflects at a mirror 182 and a dichroic mirror 183 after being focused by the condenser lens 119, and focuses on the focal point behind the objective lens 121. Then, the excitation beam is converted into a parallel light flux with a size larger than the observation field in the objective lens 121 and enters the flowcell 110. In addition to Köhler illumination, critical illumination and the like can be used as the illumination method, however, Köhler illumination has an effect of irradiating the irradiation area evenly. In addition, as the light source 111, a xenon lamp, a halogen lamp, a mercury lamp and the like can be used in addition to the laser. The dichroic mirror 183 has transmission properties of reflecting the light from the light source 111 and transmitting the fluorescence from the labeled bases.

FIG. 29 shows another embodiment of the irradiation unit 112 of this Example. By altering the position of the mirror 182 and thus bringing the focal point of the excitation beam off the axis of the objective lens, oblique illumination was achieved. This can reduce the background light and thus has an effect of improving the detection sensitivity. As the embodiment of oblique illumination, embodiments described in Highly inclined thin illumination (Makio Tokunaga et al., Nat. Methods 5, 159-161 (2008)), and low-angle oblique illumination (Yasushi Sako, Molecular Systems Biology 56 (2006)) can be used. In case of oblique illumination, use of an oil immersion objective lens can increase the angle of incidence and the effect of reducing the background light becomes significant. When an oil immersion objective lens is used as the objective lens 121, total reflection illumination as shown in FIG. 30 is possible by further moving the mirror 182. In this case, it is necessary to fill the gap between the objective lens 121 and the flowcell 110 with an immersion oil 185. Total reflection illumination further improves the effect of reducing the background light. With the structure in FIG. 30, the reaction spots 105 which are arranged with higher density can be detected, by further combining with the super-resolution technique described in Peter Kner et al., Nature Methods, vol. 6, No. 5, 339-342 (2009).

FIG. 31 shows another embodiment of the detection unit 120 of this Example. The characteristic of this embodiment is the use of confocal technique. A primary image is formed by imaging the fluorescent spots on the sample substrate 210 with an imaging lens 130a and the primary image is imaged on the image sensor 134 with imaging lenses 130b and 130c. The surface on which the primary image is formed has pinholes 186. Decreasing the sizes of the pinholes 186 results is an effect of preventing the background light. When the reaction spots 105 are arranged in a lattice, the observation field can be further enlarged by providing the pinholes 186 in positions corresponding to the reaction spots 105 of the primary image (multi-pinhole).

Example 9

FIG. 32 shows a structure around the sample substrate 210 of this Example. The structure is characterized by a light-blocking thin film 191 deposited on the sample substrate 210 and a lattice of openings 192 each having a diameter of 500 nm or less formed in the light-blocking thin film 191. FIG. 32(a) is a view of the sample substrate 210 from above. FIGS. 32(b) and (c) each show a part of the AA' cross-section. The diagram (b) shows the case in which the beads 204 on which the identical DNA fragments 201 are immobilized are used as the reaction spots 105. The diagram (c) shows the case in which clusters of the identical DNA fragments 201 are used as the reaction spots 105.

Details of the sample substrate 210 of FIG. 32 are explained. The structure is composed of an optically transparent sample substrate 210 such as quartz glass, the light-blocking thin film 191 formed on the sample substrate 210, and the openings 192 formed in the light-blocking thin film 191. For the production, aluminum is first deposited in a thickness of 200 nm on the sample substrate 210, thereby forming the light-blocking thin film 191. In addition to aluminum, other materials such as silver, gold, chromium and silicon carbide may be used to form the light-blocking thin film 191. Two or more openings 192 each with a diameter of 200 nm are formed on the light-blocking thin film 191 with a distance of 1 µm by electron beam lithography. The openings 192 may be holes piercing through the film, or very thin films may remain on the sample substrate 210.

By making the diameters of the openings 192 the same as or smaller than the wavelength (500 nm or less), the excitation light entering perpendicularly from under the sample substrate 210 does not pass through the openings but stays at around the bottoms of the openings (creates a near field on the surface of the sample substrate 210). This has an effect of reducing the background light. The structure of FIG. 31 can be used as the structure of the detection unit 120 and the irradiation unit 112. In this case, a multi-pinhole structure of the pinholes 186 has an effect of enlarging the field. Structures other than that of FIG. 31 may be combined.

Example 10

This Example is characterized by the DNA sequencing using fluorescence resonance energy transfer (FRET). As shown in FIG. 33, an acceptor luminophore 251 was used as the fluorophore attached to the phosphate terminal of a base. The polymerase 401 is labeled with a donor luminophore 252. Although Cy5 was used as the acceptor luminophore 251 and Cy3 was used as the donor luminophore 252 in this Example, other kinds of fluorophore may be used. As shown in FIG. 33(b), the donor luminophore 252 emits fluorescence by the excitation light from the light source 111. When a base labeled with the acceptor luminophore 251 is incorporated therein by extension reaction, the luminescence from the donor luminophore 252 stops by FRET and fluorescence is emitted from the acceptor luminophore 251 (FIG. 33(c)). When the acceptor luminophore 251 is removed together with the phosphate group, only the fluorescence from the donor luminophore 252 is emitted.

Using the detection unit 120 having a structure shown in FIG. 34(a), the fluorescent changes of the two kinds of luminophore can be detected. A dichroic mirror 253 transmits the luminescence from the acceptor luminophores 251 and reflects the luminescence from the donor luminophores 252. A detection filter 122f is a band-pass filter which transmits only the luminescence from the acceptor luminophores 251 and a detection filter 122g is a band-pass filter which transmits only the luminescence from the donor luminophores 252. The fluorescence from the acceptor luminophores 251 and that of the donor luminophores 252 which have passed through the respective detection filters 122 form images on image sensors 134f and 134g by imaging lenses 130f and 130g, respectively. FIG. 34(b) shows the time-changes in pixel value during the extension reaction of a reaction spot 105. The change in pixel value measured by the image sensor 134g shows the time-change in fluorescence intensity of the donor luminophores 252. The change in pixel value measured by the image sensor 134f shows the time-change in fluorescence intensity of the acceptor luminophores 251. When bases are introduced and the extension reaction starts, the luminescence intensity of the donor luminophores 252 decreases and the luminescence intensity of the acceptor luminophores increases. As the extension reaction progresses, there are less unreacted DNA fragments and the relation of the luminescence intensities of the donor luminophores 252 and the acceptor luminophores 251 is reversed.

The detection unit 120 of this Example may have the structures of the detection unit 120 shown in the Examples above in addition to that of FIG. 34(a). In this regard, however, it is desirable that the detection filter 122 has transmission properties of transmitting the fluorescence from the acceptor luminophores 251 only. The simultaneous detection of the fluorescence intensity of the donor luminophores 252 as in FIG. 34(a) has an effect of improving the detection accuracy. In addition, it can be known that the luminescence of the donor luminophores 252 has stopped from the decrease in the fluorescence intensity. In this case, by adding the polymerase 401, the donor luminophores 252 can be newly supplied.

A quantum dot may be used as the donor luminophore 252, as well as a fluorophore. A quantum dot does not lose the luminescence easily and thus has an effect of a long read base length. A bead 204 on which the donor luminophore 252 is embedded as shown in FIG. 35 may be used as the donor luminophore 252. In this case, the polymerase 401 is not modified with the donor luminophore 252. The donor luminophore 252 may be a molecule obtained by modifying an intercalator 254 with the donor luminophore 252 as shown in FIG. 36. In this case, two or more donor luminophores 252 intercalate in the double strand of a DNA fragment. As the extension reaction progresses, the distance between the donor luminophores and the base to be incorporated becomes larger and thus FRET is less likely to occur. In this case, by adding the donor luminophores 252 to the flow path, the donor luminophores intercalate in the newly extended double strand and thus FRET is more likely to occur. Use of the intercalator 254 modified with the donor luminophore 252 has an effect of a long read base length because the donor luminophores 252 can be supplied easily.

The FRET efficiency is 50% when the distance between the acceptor luminophore 251 and the donor luminophore 252 is the Förster distance (about 5 nm) and this efficiency decreases in inverse proportion to the 6th power of the distance. Thus, the luminescence from the acceptor luminophore 251 is observed only during the extension reaction in which the acceptor luminophore 251 and the donor luminophore 252 come close to each other with a distance around the Förster distance. Because the acceptor luminescence from a free base is inhibited, this has an effect of reducing the background light.

Example 11

This Example is characterized by detecting the fluorescence from the reaction spots 105 directly with the image sensor 134 without imaging the fluorescence. Because the lens between the image sensor 134 and the flowcell 110 is not necessary, this Example has an effect of reducing the size of the device.

FIG. 37 shows a structure around the image sensor 134 and the cover substrate 301 in this Example. The other components, the method of DNA sequencing and the like are the same as those of the Examples above. The detection unit 120 is composed of the image sensor 134 and the detection filter 122. The reaction spots 105 are on the cover substrate 301. The reaction spots 105 are arranged in a lattice with a distance of an integral multiple number of the pixel distance of the detection elements 323. To simplify the figure, the identical DNA fragments 201 are drawn in one of the reaction spots 105 in the figure. The DNA fragments 201 may be immobilized on the beads 204. A method for arranging the reaction spots 105 in a lattice is described in R. Drmanac et al., Science 327, 78-81 (2010). Although it is not shown in the figure, the spacer 306 and the sample substrate 210 as shown in FIG. 3 are piled on the cover substrate 301 to form the flowcell structure. Accordingly, the flow path 311 is formed in the area in which the reaction spots 105 are arranged. In this regard, however, there is no reaction spot on the sample substrate 210. The structure described in Example 1 can be used for the irradiation unit 112. The detection filter 122 is between the cover substrate 301 and the detection elements 323 and these three kinds of component are attached closely and fixed. The detection filter 122 has a property of transmitting only the fluorescence of the fluorophores attached to the bases. In order to reduce the cross-talk between adjacent reaction spots 105 due to spreading of the light, the thickness of the detection filter 122 is preferably small. In this Example, an interference filter having a thickness of 5 to 90 μm was used. The fluorescence from the reaction spots 105 passes through the detection filter 122 and is detected by the facing pixel areas. When the sizes of the reaction spots 105 are the same as or smaller than the pixel size and the reaction spots 105 are arranged in a lattice with a distance same as the pixel distance, one reaction spot 105 can be detected by one pixel and thus the number of parallel processing can be maximized. It is also possible to form the reaction spots 105 on the detection filter 122 and use the detection filter 122 also as the cover substrate 301. Because the reaction spots 105 and the detection elements 323 come closer, this case has an effect of reducing the cross-talk.

FIG. 38 shows another embodiment of this Example. This embodiment is characterized in that the lights from the reaction spots 105 pass through openings 322 formed in a light-blocking substrate 321 and are then detected. This has an effect of reducing the cross-talk. The reaction spots 105 are arranged on the detection filter 122.

The detection filter 122 also functions as the cover substrate 301. The surface of the detection filter 122 on which the reaction spots 105 are not immobilized is attached closely to the substrate 321. The substrate 321 has the openings 322 each having an approximately same size as that of the detection spots. The openings 322 are arranged with the same lattice distance as that of the reaction spots 105 and one reaction spot 105 faces one opening 322. A silicon substrate having a thickness of 60 μm was used as the substrate 321. After depositing aluminum in a film thickness of 200 nm on the surface of silicon, a pattern of the openings was formed by photolithography. Holes piercing through the silicon substrate, which are the openings 322, were formed by dry-etching the silicon substrate using the aluminum film as a mask. Methods other than the above method may be used for producing the substrate 321.

FIG. 39(a) shows another embodiment of this Example. This embodiment is characterized by having the reaction spots 105 in the openings. The embodiment has not only an effect of reducing the cross-talk but also an effect of reducing the reagent amounts because the volume of the flow path can be reduced. FIG. 39(b) shows a part of the BB' cross-section of the diagram (a). A fragment reaction spot 105 is trapped in the space of an opening 322. The substrate 321 and the detection filter 122 are attached closely and fixed to prevent the leakage of the solutions. The detection filter 122 also functions as the cover substrate 301. The sample substrate 210, which is not shown in the figure, is on the substrate 321 through the spacer 306 to form the flow path 311. Because the volume of the flow path is reduced by the volume of the substrate 321, the reagent amounts are low.

Example 12

This Example is characterized by using two or more kinds of fluorophore as the fluorophores for modifying the phosphate terminals of the bases. From this, the dynamic range for detecting the fluorescent changes by the extension reaction can broaden and a homopolymer with a longer base length can be sequenced.

The embodiment in FIG. 34(a) can be used for a structure in the case of using two kinds of fluorophore (which is referred to as a fluorophore 1 and a fluorophore 2). In this case, band-pass filters which transmit only the fluorescence from the fluorophore 1 and only the fluorescence from the fluorophore 2 are desirably used as the detection filters 130f and 130g, respectively. Cy3 and Cy5 were used as the fluorophores. The detection filter 130g is a band-pass filter which transmits Cy3 only and the detection filter 130f is a band-pass filter which transmits Cy5 only. FIG. 40 shows the changes in pixel value during the extension reaction of a reaction spot 105 measured by the image sensors 134g and 134f in this Example. The values of the image sensors 134g and 134f indicate the changes in the fluorescence intensities of Cy3 and Cy5, respectively, with respect to the same spot. Because the behaviors of the changes in the intensities of Cy3 and Cy5 are similar, it can be seen that the bases (A) modified with the two kinds of fluorophore have been incorporated in the reaction spot 105. The sum of the changes in the fluorescence intensity obtained in the image sensors 134g and 134f is used for the value of the change in fluorescence intensity defined in Example 1. The figure shows the intensity changes of the fluorescence emitted from the reaction spot 105 when 20 bases of A extended. The dynamic ranges of the pixel values of the image sensors used in this Example are 0 to 4095. When only Cy3 is used as in Example 1, the range exceeds 4095. However, by using two kinds of fluorophore as in this Example, the dynamic range can broaden and a homopolymer with a long base length can be detected.

Example 13

This Example is characterized by detecting two types of FRET phenomenon at the same time. This has an effect of shortening the sequencing time because the sense and antisense DNA fragments on the reaction spots 105 can be sequenced simultaneously.

The methods for forming the reaction spots described in NPL 1 and NPL 2 can amplify sense and antisense DNA fragments in the reaction spots. Sense and antisense DNA fragments have sequences complementary to each other. In the Examples above, either one of the sense and antisense DNA fragments is extended in one extension reaction. On the other hand, in this Example, primers hybridize with both of the sense and antisense DNA fragments and the two kinds of DNA fragment are extended simultaneously. FIG. 41 is a schematic diagram of the sequential extension reaction using fluorescence resonance energy transfer (FRET) in this Example. The primer terminals of an antisense DNA fragment 201b and a sense DNA fragment 201a are labeled with donor luminophores 252a and 252b which are different from each other (FIG. 41(a)). Bases A labeled with acceptor fluorophores 251a and 251b are introduced (FIG. 41(b)). Kinds of luminophore are selected in such away that the energy transfers (FRET) from the donor luminophore 252a to the acceptor luminophore 251a and from the donor luminophore 252b to the acceptor luminophore 251b. Because base A is complementary to the bases (T) of the antisense DNA fragment 201b and the sense DNA fragment 201a, the bases A are incorporated in both fragments by extension reaction, resulting in the FRET (FIG. 41(c)). Because the acceptor luminophores 251a and 251b, which cause FRET, have been incorporated here, FRET has been observed in both of the DNA fragments; however, when the base A labeled with the acceptor luminophore 251a has been incorporated in the antisense DNA fragment 201b, FRET is not observed. Once the extension reaction is finished and the acceptor fluorophores are removed, the FRET does not occur any more (FIG. 41(d)). The solution in the solution tank 102b is sent to wash out the excess bases and the next bases (C) are introduced (FIG. 41(e)). Because only the antisense DNA fragment 201b has the base (G) complementary to the base C, FRET is observed. FRET is not observed in the sense DNA fragment 201a (FIG. 41(f)). Although Alexa 488 was used as the donor luminophore 252a and Alexa 647 was used as the donor luminophore 252b, other luminophores may be used. Alexa 555 was used as the acceptor luminophore 251a and Alexa 700 was used as the acceptor luminophore 251b.

FIG. 42(a) shows an embodiment of the irradiation unit 112 and the detection unit 120 in this Example. Lights from light sources 111a and 111b are combined to travel in one light path by a dichroic mirror 331, enter the flowcell 110 at the total reflection angle as shown in Example 1, and form an evanescent field on the sample substrate 210. The donor luminophore 252a is excited by the light from the light source 111a and the donor luminophore 252b is excited by the light from the light source 111b. The wavelength characteristics of the dichroic mirror 253 and the detection filters 122f and 122g are designed in such a way that the fluorescence from the donor luminophore 252a is detected by the image sensor 134g and the fluorescence from the donor luminophore 252b is detected by the image sensor 134f. Components 130f and 130g are imaging lenses. An argon ion laser which oscillates at 488 nm was used as the light source 111a and a helium-neon laser which oscillates at 594 nm was used as the light source 111b. FIG. 42(b) shows changes in pixel value during the extension reaction of a reaction spot 105 obtained by the image sensors 134g and 134f. Because the decrease in the fluorescence intensity by the FRET of the donor luminophores 252b is observed with the image sensor 134g, it can be seen that the bases have been incorporated in the antisense DNA fragments 201b. Because the fluorescence from the donor luminophores 252a measured by the image sensor 134g does not change, the bases have not been incorporated.

FIG. 43 shows another embodiment of the detection unit 120 in this Example. This embodiment is characterized by having four sets of components, namely image sensors 134f, 134g, 134h and 134i, imaging lenses 130f, 130g, 103h and 130i and detection filters 122f, 122g, 122h and 122i. With respect to the luminescence collected by the objective lens 121, the luminescence from the donor luminophores 252a and the luminescence from the acceptor luminophores 251a are reflected by a dichroic mirror 253a, the fluorescence from the donor luminophores 252a is reflected by a dichroic mirror 253c and detected by the image sensor 134i, and the luminescence from the acceptor luminophores 251a which has passed through the dichroic mirror 253c is detected by the image sensor 134h. On the other hand, among the luminescence from the donor luminophores 252b and the luminescence from the acceptor luminophores 251b which have passed through the dichroic mirror 253a, the luminescence from the donor luminophores 252b is reflected by a dichroic mirror 253b and detected by the image sensor 134g and the luminescence from the acceptor luminophores 251b passes through the dichroic mirror 253b and is detected by the image sensor 134f. Such simultaneous detection of the changes in the fluorescence intensities of the donor luminophores 252a and 252b and the acceptor luminophores 251a and 251b has an effect of improving the sequencing accuracy.

Although fluorophores were used as the donor luminophores 252 above, two kinds of quantum dot may be used. Because only one light source 111 is used, this case has an effect of reducing the cost of the structure and simplifying the structure. In addition one kind or three or more kinds of luminophore may be used as the acceptor luminophores 251. In this case, it is necessary to select two kinds of donor luminophore 252 and one kind or three or more kinds of acceptor luminophore 251 in such a way that energy transfers from the two kinds of donor luminophore 252. When only one kind is used for the acceptor luminophores 251, three image sensors 134 may be used for the structure of FIG. 43. Use of one kind of acceptor luminophore 251 has an effect of reducing the reagent amounts.

Although the observation field(s) is moved and the fields are scanned by driving the flowcell (s) 110 in the Examples above, the observation field(s) may be moved and the fields may be scanned by driving the detection unit(s) 120.

Examples of the invention have been explained above, however, the invention is not limited to these examples and one skilled in the art would understand that various changes are possible within the scope of the invention described in the claims. Appropriate combinations of the Examples are also included in the scope of the invention.

REFERENCE SIGNS LIST

112: Irradiation Unit
113, 113a, 113b: Excitation Filter
110: Flowcell
120: Detection Unit
104: Solution-Sending Unit
101: Controller PC
102d: Waste-Fluid Tank
111, 111a, 111b: Light Source
140: Light-Blocking Shutter
119: Condenser Lens
137: Total Reflection Prism
210: Sample Substrate
121: Objective Lens
122, 122f, 122g, 122h, 122i: Detection Filter
130, 130a, 130b, 130c, 130f, 130g, 130h, 130i: Imaging Lens
134, 134f, 134g, 134h, 134i: Image Sensor
138: Z-Axis Driving Unit
201: DNA Fragment
204: Bead
105: Reaction Spot
311, 311a, 311b, 311c, 311d, 311e: Flow Path
306: Spacer
301: Cover Substrate
308, 308a: Solution Inlet
309, 309a: Solution Outlet 102, 102a, 102t, 102g, 102c, 102b, 162a, 162t, 162g, 162c: Solution Tank
103a, 103t, 103g, 103c, 103b: Solution-Sending Pump
401: Polymerase
902a, 902t, 902g, 902c, 902b: Switching Valve
904, 904b: Changeover Valve
150: Power Supply
151: Electrode Switch
152: Wire
153: Electrode
720: Nozzle
719: Solution-Sending Unit
154, 712, 741, 731, 761: Driving Unit
751: Rotary Driving Unit
181: Beam Expander
182: Mirror
183, 253, 331, 253a, 253b, 253c: Dichroic Mirror
184: Temperature-Regulating Mechanism
185: Immersion Oil
186: Pinhole
191: Light-Blocking Thin Film
192, 322: Opening
251, 251a, 251b: Acceptor Luminophore
252, 252a, 252b: Donor Luminophore
254: Intercalator
321: Substrate
323: Detection Element
201b: Antisense DNA Fragment
201a: Sense DNA Fragment

The invention claimed is:

1. A DNA sequencing device for sequencing DNA without a terminator and in real-time, comprising:
    a flowcell in which two or more DNA fragment clusters of two or more DNA fragments having identical nucleotide sequences are immobilized, wherein at least a part of the flowcell where the two or more DNA fragment clusters are immobilized is made of a transparent material;
    an irradiation light source to irradiate the part of the flowcell in which the DNA fragment clusters are immobilized;
    a first lens to collect fluorescence from the part of the flowcell in which the DNA fragment clusters are immobilized; and
    a light-detection sensor to detect collected light from the lens; a plurality of solution tanks connected to the flow cell, the solution tanks including a first tank storing a dATP solution containing dATP having a fluorescently modified phosphate terminal, a second tank storing a dCTP solution containing dCTP having a fluorescently modified phosphate terminal, a third tank storing a dGTP solution containing dGTP having a fluorescently modified phosphate terminal, a fourth tank storing a dTTP solution containing dTTP having a fluorescently modified phosphate terminal, and a fifth tank storing a buffer solution for washing out the flowcell;
    one or more pumps and valves connected to the flow cell and the solution tanks to send the dATP solution, the dCTP solution, the dGTP solution, the dTTP solution, and the buffer solution to the flowcell; and
    a controller which is programmed to fill the part of the flowcell where the two or more DNA fragment clusters are immobilized with the buffer solution, and sequentially send the dATP solution, the dCTP solution, the dGTP solution, and the dTTP solution to the part of the flowcell where the DNA fragment clusters are immobilized,
    wherein the controller is further programmed to sequence the DNA fragment clusters in parallel by processing the collected light from the lens when each of the dATP solution, the dCTP solution, the dGTP solution, and the dTTP solution are sequentially sent to the part of the flowcell where the DNA fragment clusters are immobilized, and
    wherein the dATP solution, the dCTP solution, the dGTP solution, and the dTTP solution are sequentially sent a plurality of times, and
    the DNA sequencing device further comprising:
    a driving unit on which the flowcell is fixed, and
    wherein the controller is further programmed to control the driving unit to drive the flowcell so that a head of each of the dATP solution, the dCTP solution, the dGTP solution, and the dTTP solution in the flowcell substantially corresponds to a light-detection field of the light-detection sensor.

2. The DNA sequencing device of claim 1,
    wherein the solution tanks are disposed on the flowcell.

3. The DNA sequencing device of claim 1,
    wherein the controller is further programmed to control the light-detection sensor to detect a change in fluorescence of the part of the flowcell where the DNA fragment clusters are immobilized before and after sending each of the dATP solution, the dCTP solution, the dGTP solution, and the dTTP solution.

4. The DNA sequencing device of claim 1,
    wherein the flowcell has two or more flow paths.

5. The DNA sequencing device of claim 1, wherein the flowcell has two or more flow paths.

6. The DNA sequencing device of claim 2,
    which has a power supply for applying a voltage between the containers, and
    which is characterized in that the solutions are sent by electrophoresis between the containers.

7. The DNA sequencing device of claim 6,
    which has two or more flow paths and a driving unit for driving the flowcell,
    wherein the flowcell is driven in a direction opposite to a solution-sending direction at a speed same as a solution-sending speed and then a light-detection field is moved to another flow path.

8. The DNA sequencing device of claim 1, further comprising:
    a second lens disposed between the first lens and the light-detection sensor.

9. The DNA sequencing device of claim 1,
    which is characterized in that the dATP solution contains non-modified dATP, the dCTP solution contains non-modified dCTP, the dGTP solution contains non-modified dGTP, and the dTTP solution contains non-modified dTTP.

10. The DNA sequencing device of claim 1,
    wherein the solution tanks further include a sixth solution tank containing a non-modified dATP solution, a seventh solution tank containing a non-modified dCTP solution, an eighth solution tank containing a non-modified dGTP solution, and a ninth solution tank containing a non-modified dTTP solution,
    wherein the controller is further programmed to send the non-modified dATP solution, the non-modified dCTP solution, the non-modified dGTP solution, and the non-modified dTTP solution to the flowcell.

11. The DNA sequencing device of claim 1,
    which is characterized in that the flowcell has two or more flow paths, the nucleic acid analysis device has a driving unit for driving the flowcell, the flowce comprises sample substrate and the nucleic acid analysis device repeats a process 1 for obtaining an image of fluorescence from the sample substrate surface surrounded by one of the flow paths, a process 2 for moving a light-detection field to the substrate surface surrounded by another flow path by the driving unit after the process 1, and a process 3 for obtaining an image of fluorescence from the substrate surface surrounded by the flow path.

12. The DNA sequencing device of claim 1, which further has an optical element which reflects a light emitted from the irradiation unit and transmits the fluorescence, the flowcell comprises sample substrate and which is characterized in that the light emitted from the irradiation unit is reflected by the optical element, then passes through the lens and irradiates the sample substrate surface.

13. The DNA sequencing device of claim 1, which is characterized in that the flowcell has a substrate and a light-blocking film, the light-blocking film has an opening of 500 nm or less, the substrate at the bottom of the opening is transparent, and the clusters are immobilized on the bottom of the opening.

14. The DNA sequencing device of claim 1, which further has two or more luminophores disposed in the clusters and which is characterized in that fluorophores attached to the bases absorb energy from the luminophores and emit fluorescence.

15. The DNA sequencing device of claim 1, wherein a light from the irradiation light source enters the flowcell from a surface opposite to a side of the flowcell at which the DNA fragment clusters are immobilized and a near field is generated at the side at which the DNA fragment clusters are immobilized.

16. The DNA sequencing device of claim 1, wherein the controller is further programmed to calculate an average derivative of a fluorescence intensity from the collected light when each of the dATP solution, the dCTP solution, the dGTP solution, and the dTTP solution are sequentially sent to the part of the flowcell where the DNA fragment clusters are immobilized.

* * * * *